(12) United States Patent
Aissaoui et al.

(10) Patent No.: US 8,236,964 B2
(45) Date of Patent: Aug. 7, 2012

(54) THIAZOLIDINE DERIVATIVES AS OREXIN RECEPTOR ANTAGONISTS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 300 days.

(21) Appl. No.: 12/593,095

(22) PCT Filed: Mar. 25, 2008

(86) PCT No.: PCT/IB2008/051110
§ 371 (c)(1),
(2), (4) Date: Sep. 25, 2009

(87) PCT Pub. No.: WO2008/117241
PCT Pub. Date: Oct. 2, 2008

(65) Prior Publication Data
US 2010/0113531 A1    May 6, 2010

(30) Foreign Application Priority Data

Mar. 26, 2007 (WO) ............... PCT/IB2007/051048
Feb. 21, 2008 (WO) ............... PCT/IB2008/050620

(51) Int. Cl.
*A61K 31/427* (2006.01)
*C07D 417/12* (2006.01)
*C07D 417/14* (2006.01)

(52) U.S. Cl. ...... 548/200; 544/105; 546/121; 546/269.7; 548/126; 548/154; 548/180; 548/181; 514/230.5; 514/300; 514/342; 514/362; 514/364; 514/365; 514/367

(58) Field of Classification Search ............... 548/200
See application file for complete search history.

(56) References Cited

U.S. PATENT DOCUMENTS

| | | |
|---|---|---|
| 7,994,336 B2 | 8/2011 | Aissaoui et al. |
| 2004/0192673 A1 | 9/2004 | Gaillard et al. |
| 2010/0016401 A1 | 1/2010 | Aissaoui et al. |
| 2010/0069418 A1 | 3/2010 | Aissaoui et al. |
| 2010/0168134 A1 | 7/2010 | Breslin et al. |
| 2010/0184808 A1 | 7/2010 | Aissaoui et al. |
| 2010/0197733 A1 | 8/2010 | Aissaoui et al. |
| 2010/0204285 A1 | 8/2010 | Aissaoui et al. |
| 2010/0222328 A1 | 9/2010 | Aissaoui et al. |
| 2010/0222600 A1 | 9/2010 | Aissaoui et al. |
| 2011/0009401 A1 | 1/2011 | Aissaoui et al. |
| 2011/0009461 A1 | 1/2011 | Aissaoui et al. |
| 2011/0039857 A1 | 2/2011 | Aissaoui et al. |
| 2011/0124636 A1 | 5/2011 | Aissaoui et al. |

FOREIGN PATENT DOCUMENTS

| | | |
|---|---|---|
| EP | 58906 A1 | 9/1982 |
| WO | WO 01/96302 | 12/2001 |
| WO | WO 02/44172 | 6/2002 |
| WO | WO 02/090355 | 11/2002 |
| WO | WO 03/002559 | 1/2003 |
| WO | WO 03/002561 | 1/2003 |
| WO | WO 03/032991 | 4/2003 |
| WO | WO 03/041711 | 5/2003 |
| WO | WO 03/051368 | 6/2003 |
| WO | WO 03/051873 | 6/2003 |
| WO | WO 2004/026866 | 4/2004 |
| WO | WO 2004/041791 | 5/2004 |
| WO | WO 2004/041807 | 5/2004 |
| WO | WO 2004/041816 | 5/2004 |
| WO | WO 2005/092890 | 10/2005 |
| WO | WO 2006/011042 | 2/2006 |
| WO | WO 2006/069155 | 6/2006 |
| WO | WO 2008/150364 | 12/2008 |

OTHER PUBLICATIONS

Voisin et al., "Orexins and their receptors: structural aspects and role in peripheral tissues," Cell Mol. Life Sci., 60:72-87 (2003).*
Hungs et al., "Hypocretin/orexin, sleep and narcolepsy," BioEssays 23(5): 397-408 (May 2001).*
Sakurai, T. et al., Orexin & Orexin Receptors: A Family of Hypothalamic Neuropeptides and GProtein-Couples Receptors that Regulate Feeding Behavior, Cell, Feb. 20, 1998, vol. 92, 573-585, Cell Press.
Berry, C.R., Cycloaddition Reactions of Thiazolium Azomethine Ylides: Application to Pyrrolo[2,1b]thiazoles, Organic Letters, 2007, vol. 9, No. 21, 4099-4102.
Cai, J., Antagonists of the Orexin Receptors, Expert Opinion on Therapeutic Patents, May 1, 2006, vol. 16, No. 5, 631-646, Informa Healthcare, GB.
Chemelli, R.M., Narcolepsy in orexin Knock Out Mice: Molecular Genetics of Sleep Regulation, Cell, Aug. 20, 1999, vol. 98, 437-451, Cell Press.

(Continued)

*Primary Examiner* — Laura L. Stockton
(74) *Attorney, Agent, or Firm* — Hoxie & Associates LLC

(57) ABSTRACT

The invention relates to novel thiazolidine derivatives of the formula (I) wherein A and $R^1$ are as described in the description and their use as medicaments, especially as orexin receptor antagonists.

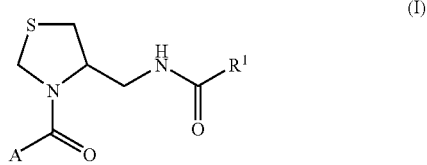

17 Claims, No Drawings

OTHER PUBLICATIONS

Chen, Q., et al., Methyl Fluorosulphonyldifluoroacetate; a New Trifluoromethylating Agent, Journal of Chemical Society, Chemical Communications, Jan. 27, 1989, vol. 11, 705-706,China.

Chen, Q., et al. An Improved and Practical Synthesis of 4-Fluorobenzaldehyde by Halogen-Exchange Fluorination Reaction, Journal of Fluorine Chemistry, 1989 vol. 44, 291-298, China.

Danheiser, R.L., Reactions of (Trialkylsilyl)vinylketenes with Lithium Ynolates: A New Benzannulatlon Strategy, Organic Letters, 2005, vol. 7, No. 18, 3905-3908.

Differding, E., N-Fluorobenzenesulfonimide: A Practical Reagent for Electrophilic Fluorinations, Synlett, Mar. 1991, vol. 1, 187-189, George Thieme Verlag KG, Germany.

Eissenstat, M.A., Aminoalkylindoles: Structure-Activity Relationships of Novel Cannabinoid Mimetics, Journal of Medicinal Chemistry, 1995, vol. 38, 3094-3105, American Chemical Society, Washington DC, USA.

Goldstein, S.W., et al., A Facile Synthesis of Methyl 2-Substituted-4-benzoxazolecarboxylates, Journal of Heterocyclic Chemistry, 1990, vol. 27, 335-336.

Gould, P.L., Salt Selection for Basic Drugs, International Journal of Pharmaceutics, 1986, vol. 33, 201-217.

Kawase, et al., The Syntheses of Benzofuran-carboxylic Acids and the Acetylation of Their Esters, Bulletin of the Chemical Society of Japan, 1967, vol. 40, No. 5, 1224-1231, Japan.

Kuroita, T., et al., Design and Synthesis of 6-Chloro-3, 4-dihydro-4-methyl-2H-1,4-benzoxazine-8-carboxamide Derivatives as Potent Serotonin-3 (5-HT$^3$) Receptor Antagonists, Chemical Pharmaceutical Bulletin, 1996 vol. 44, No. 4, 756-764.

Mohamadi, F., et al., Total Synthesis and Biological Properties of Novel Antineoplastic (Chloromethyl)furanoindolines: An Asymmetric Hydroboration Mediated Synthesis of the Alkylation Subunits, Journal of Medicinal Chemistry, 1994, vol. 37, 232-239.

Eicher, T., et al., The Chemistry of Heterocycles: Structures, Reactions, Synthesis, and Applications, 2$^{nd}$ Edition 2003, Wiley.

Torrado, A., et al., Novel selective and potent 5-HT reuptake inhibitors with 5-HT1D antagonist activity: chemistry and pharmacological evaluation of a series of thienopyran derivatives, Bioorganic and Medicinal Chemistry, 2004, vol. 12, 5277-5295, Elsevier.

Cai, J. et al., "Antagonists of the orexin receptors", Expert Opinion on Therapeutic Patents, Informa Healthcare, GB, May 1, 2006, vol. 16, No. 5, pp. 631-646.

Aissaoui et al; "N-Glycine-Sulfonamides as Potent Dual Orexin 1/Orexin 2 Receptor Antagonists"; Bioorganic & Medicinal Chemistry Letters, vol. 18, pp. 5729-5733, 2008.

Bergman et al; "Proline Bis-Amides as Potetn Dual Orexin Receptor Antagonists", Bioorganic & Medicinal Chemistry Letters, 2008, vol. 18, 1425-1430.

Bohm et al, "Scaffold Hopping"; Drug Disc. Today Tech, 2004, vol. 1, issue 3, pp. 217-224.

Boss et al; "Biomedical Application of Orexin/Hypocretin Receptor Ligands in Neuroscience"; Journal of Medicinal Chemistry, vol. 52, No. 4, pp. 891-903; 2009.

Boss et al; "Orexin Receptor Antagonism: A New Principle in Neuroscience"; CHIMIA; vol. 62, No. 12, pp. 974-979, 2008.

Gatfield et al; "Orexin Receptor Antagonists: A New Concept in CNS Disorders"; ChemMedChem, vol. 5, pp. 1197-1214, 2010.

Langmead et al; "Characterisation of the Binding of [3H]-SB-674042, a Novel Nonpeptide Antagonist, to the Human Orexin-1 Receptor"; British Journal of Pharmacology, vol. 141, pp. 340-346, 2004.

Remington, The Science and Practice of Pharmacy, 21st Edition, 2005, Table of Contents Only.

Roecker et al, "Orexin Receptor Antagonists: Medicinal Chemistry and Therapeutic Potential"; Current Topic Medicinal Chemistry, 2008, vol. 8, 977-987.

Sifferlen et al; "Novel Pyrazolo-Tetrahydropyridines as Potent Orexin Receptor Antagonists"; Bioorganic & Medicinal Chemistry Letters, vol. 20, pp. 1539-1542, 2010.

* cited by examiner

THIAZOLIDINE DERIVATIVES AS OREXIN RECEPTOR ANTAGONISTS

CROSS REFERENCE TO RELATED APPLICATIONS

This application is a United States Application under 35 U.S.C. 371 claiming benefit of PCT Application No. PCT/IB2008/051110, filed on Mar. 25, 2008, which claims the benefit of PCT Application No. PCT/IB2007/051048, filed on Mar. 26, 2007 and PCT Application No. PCT/IB2008/050620, filed on Feb. 21, 2008.

The present invention relates to novel thiazolidine derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451). Orexin receptors are found in the mammalian brain and may have numerous implications in pathologies as known from the literature.

The present invention provides thiazolidine derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/96302. Morpholine derivatives useful as orexin receptor antagonists are disclosed in WO02/44172. N-Aroyl cyclic amine derivatives useful as orexin receptor antagonists are disclosed in WO02/90355.

The present invention describes for the first time thiazolidine derivatives as orexin receptor antagonists.

i) A first aspect of the invention consists of a compound of the formula (I)

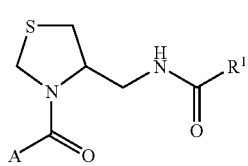

wherein
A represents

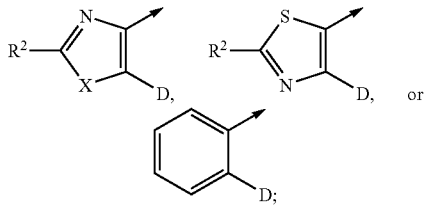

X represents O, or S;
$R^2$ represents $(C_{1-4})$alkyl;
D represents aryl, which is unsubstituted, mono-, di, or tri-substituted wherein the substituents are independently selected from the group consisting of $(C_{1-4})$alkyl, $(C_{1-4})$alkoxy, trifluoromethyl, and halogen;
$R^1$ represents aryl, wherein the aryl group is selected from the group consisting of a phenyl-, a naphthyl-, a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, a 3,4-dihydro-2H-benzo[1,4]oxazinyl-, and a 3-biphenyl group, wherein said groups are unsubstituted, mono-, di, or tri-substituted wherein the substituents are independently selected from the group consisting of $(C_{1-4})$alkyl, $(C_{1-4})$alkoxy, trifluoromethyl, halogen and nitro;
or $R^1$ represents heteroaryl, which is unsubstituted, mono-, di, or tri-substituted, wherein the substituents are independently selected from the group consisting of $(C_{1-4})$alkyl, $(C_{1-4})$alkoxy, halogen, hydroxy-$(C_{1-4})$alkyl, and trifluoromethyl.

The term "halogen" means fluorine, chlorine, or bromine, preferably fluorine or chlorine.

The term "$(C_{1-4})$alkyl" means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl and tert.-butyl. Preferred are methyl and ethyl. Most preferred is methyl.

The term "$(C_{1-4})$alkoxy" means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, isopropoxy, n-butoxy, isobutoxy, sec.-butoxy and tert.-butoxy. Preferred are methoxy and ethoxy. Most preferred is methoxy.

"D" representing "aryl" means unsubstituted, mono-, di-, or tri-substituted naphthyl or (preferably) phenyl (preferred mono- or di-substituted phenyl), wherein the substituents are independently selected from the group consisting of $(C_{1-4})$alkyl, $(C_{1-4})$alkoxy, trifluoromethyl, and halogen; most preferably from $(C_{1-4})$alkyl, $(C_{1-4})$alkoxy and halogen. Examples of "D" representing "aryl" are phenyl, 3-methylphenyl, 4-methylphenyl, 3,4-dimethylphenyl, 2-methoxyphenyl, 3-methoxyphenyl, 4-methoxyphenyl, 2-fluorophenyl, 3-fluorophenyl, 4-fluorophenyl, 3,4-difluorophenyl, 3,4-dichlorophenyl, 3-trifluoromethylphenyl and 4-trifluoromethylphenyl.

"$R^1$" representing "aryl" means a group selected from the group consisting of a phenyl, a naphthyl, a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, or a 3,4-dihydro-2H-benzo[1,4]oxazinyl-, and a 3-biphenyl-group. The above mentioned aryl group as used for "$R^1$" is unsubstituted, mono-, di-, or tri-substituted wherein the substituents are independently selected from the group consisting of $(C_{1-4})$alkyl, $(C_{1-4})$alkoxy, trifluoromethyl, halogen and nitro; preferably from $(C_{1-4})$alkyl, $(C_{1-4})$alkoxy, trifluoromethyl, and halogen; most preferably from $(C_{1-4})$alkyl, $(C_{1-4})$alkoxy and halogen. In one sub-embodiment, "$R^1$" representing "aryl" means a naphthyl- or (preferably) a phenyl group, which group is unsubstituted, mono-, di-, or tri-substituted (preferred: monosubstituted), wherein the substituents are independently selected from the group consisting of $(C_{1-4})$alkyl, $(C_{1-4})$alkoxy, trifluoromethyl, halogen and nitro; especially from $(C_{1-4})$alkyl, $(C_{1-4})$alkoxy, halogen, and trifluoromethyl (preferred: halogen). Additionally, in another sub-embodiment "$R^1$" representing "aryl" means a 2,3-dihydro-benzofuranyl-; a benzo[1,3]dioxolyl-; a 2,3-dihydro-benzo[1,4]dioxinyl-; a 4H-benzo[1,3]dioxinyl-, a 2H-chromenyl-, a chromanyl-, or a 3,4-dihydro-2H-benzo[1,4]oxazinyl group (especially a 2,3-dihydro-benzofuranyl-, a benzo[1,3]dioxolyl-, a 2,3-dihydro-benzo[1,4]dioxinyl-, or a 4H-benzo[1,3]dioxinyl group). Said aryl groups of this sub-embodiment are unsubstituted, mono-, di-, or tri-substituted (preferred unsubstituted, mono- or di-substituted) wherein the substituents are independently selected from the group consisting of $(C_{1-4})$alkyl, $(C_{1-4})$alkoxy, trifluoromethyl, and halogen; preferred from $(C_{1-4})$alkyl, $(C_{1-4})$alkoxy and halogen. In a preferred sub-embodiment, 2,3-dihydro-benzofuranyl-, benzo[1,3]dioxolyl-, 2,3-dihydro-benzo[1,4]dioxinyl-, 4H-benzo[1,3]dioxinyl-, 2H-chromenyl-, chromanyl-, and 3-biphenyl groups are preferably unsubstituted. 3,4-Dihydro-2H-benzo[1,4]oxazinyl groups are preferably unsubstituted or mono-substituted with $(C_{1-4})$alkyl (especially methyl). In another preferred sub-embodiment, a 2,3-dihydro-benzofuranyl group may also be disubstituted, wherein the substituents are independently selected from halogen and $(C_{1-4})$alkoxy.

Examples of $R^1$ representing "aryl" are naphthyl, 3-bromophenyl, 3-nitrophenyl, 3-biphenyl, 2,3-dihydro-benzofuran-4-yl, 2,3-dihydro-benzofuran-7-yl, 7-chloro-2-methoxy-2,3-dihydro-benzofuran-4-yl, 4H-benzo[1,3]dioxin-5-yl, 4H-benzo[1,3]dioxin-8-yl, benzo[1,3]dioxol-4-yl, 2,3-dihydro-benzo[1,4]dioxin-5-yl, chromen-5-yl, chroman-5-yl, chroman-8-yl, 3,4-dihydro-2H-benzo[1,4]oxazin-5-yl, 4-methyl-3,4-dihydro-2H-benzo[1,4]oxazine-5-yl, 3,4-dihydro-2H-benzo[1,4]oxazin-8-yl, and 4-methyl-3,4-dihydro-2H-benzo[1,4]oxazine-8-yl. Preferred are 2,3-dihydro-benzofuran-4-yl, 2,3-dihydro-benzofuran-7-yl, 7-chloro-2-methoxy-2,3-dihydro-benzofuran-4-yl, 2,3-dihydro-benzo[1,4]dioxin-5-yl, chroman-5-yl, chroman-8-yl, 3,4-dihydro-2H-benzo[1,4]oxazin-5-yl, 4-methyl-3,4-dihydro-2H-benzo[1,4]oxazine-5-yl, 3,4-dihydro-2H-benzo[1,4]oxazin-8-yl, and 4-methyl-3,4-dihydro-2H-benzo[1,4]oxazine-8-yl. In another embodiment, preferred examples of $R^1$ representing "aryl" are 2,3-dihydro-benzo[1,4]dioxinyl and 3-bromophenyl.

The term "heteroaryl" means a 5- to 10-membered monocyclic or bicyclic (preferred 8- to 9-membered bicyclic) aromatic ring containing 1, 2 or 3 heteroatoms, each independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl and imidazo[2,1-b]thiazolyl. In addition to the above list, further examples are benzoisothiazolyl, and pyrrolo[2,1-b]thiazolyl. Preferred examples are thienyl, thiazolyl, pyrazolyl, pyridyl, indolyl, benzofuranyl, indazolyl, benzoxazolyl, benzisoxazolyl, benzothiazolyl, benzoxadiazolyl, benzothiadiazolyl, imidazo[1,2-a]pyridyl, imidazo[2,1-b]thiazolyl, benzoisothiazolyl, and pyrrolo[2,1-b]thiazolyl. In another embodiment, preferred examples are benzisoxazolyl, benzoxadiazolyl, benzothiadiazolyl, imidazo[1,2-a]pyridyl, imidazo[2,1-b]thiazolyl, benzoisothiazolyl, and pyrrolo[2,1-b]thiazolyl. The above-mentioned heteroaryl groups are unsubstituted, mono-, di-, or tri-substituted (preferred unsubstituted, mono-, or di-substituted) wherein the substituents are independently selected from the group consisting of $(C_{1-4})$alkyl, $(C_{1-4})$alkoxy, halogen, hydroxy-$(C_{1-4})$alkyl, and trifluoromethyl; especially from $(C_{1-4})$alkyl, $(C_{1-4})$alkoxy, halogen, and trifluoromethyl; preferred from $(C_{1-4})$alkyl, halogen, and trifluoromethyl. In another embodiment, preferred examples of such heteroaryl groups are thienyl, pyridyl, indolyl, indazolyl, benzofuranyl, and imidazo[2,1-b]thiazolyl, which groups may be unsubstituted, mono-, di-, or tri-substituted (preferred unsubstituted, mono-, or di-substituted, most preferred unsubstituted, or mono-substituted) wherein the substituents are independently selected from the group consisting of $(C_{1-4})$alkyl, $(C_{1-4})$alkoxy, halogen, and trifluoromethyl (preferred $(C_{1-4})$alkyl, and halogen).

In particular, the above mentioned "heteroaryl" groups as used for the substituent "$R^1$" are preferably substituted as follows: thienyl groups are substituted with halogen; thiazolyl groups are di-substituted with $(C_{1-4})$alkyl; pyrazolyl groups are di-substituted with $(C_{1-4})$alkyl; pyridyl groups are mono-substituted with halogen; indolyl groups are mono-substituted with $(C_{1-4})$alkyl (especially methyl); indazolyl groups are unsubstituted or mono-substituted with $(C_{1-4})$alkyl (especially methyl); benzoxazolyl groups are unsubstituted, or mono-substituted with $(C_{1-4})$alkyl (especially methyl); benzothiazolyl groups are unsubstituted or mono-substituted with halogen; benzisoxazolyl, benzoxadiazolyl, benzothiadiazolyl, and benzoisothiazolyl groups are unsubstituted; imidazo[1,2-a]pyridyl are unsubstituted or mono-substituted with $(C_{1-4})$alkyl (especially methyl); pyrrolo[2,1-b]thiazolyl groups are unsubstituted or mono-substituted with $(C_{1-4})$alkyl (especially methyl); and imidazo[2,1-b]thiazolyl groups are mono-substituted with $(C_{1-4})$alkyl (especially methyl); benzofuranyl groups are preferably unsubstituted, mono-, or di-substituted wherein the substituents are independently selected from $(C_{1-4})$alkyl, halogen, hydroxy-$(C_{1-4})$alkyl, and trifluoromethyl, especially from $(C_{1-4})$alkyl, halogen, and trifluoromethyl. Examples of said benzofuranyl groups are benzofuran-4-yl, 7-chloro-benzofuran-4-yl, 7-fluoro-benzofuran-4-yl, 2-fluoro-benzofuran-4-yl, 3-methyl-benzofuran-4-yl, 2-methyl-benzofuran-4-yl, 2-hydroxymethyl-benzofuran-4-yl, 5-chloro-2-methyl-benzofuran-4-yl, 7-chloro-2-methyl-benzofuran-4-yl, 7-fluoro-2-methyl-benzofuran-4-yl, 6-chloro-2-methyl-benzofuran-4-yl, 6-fluoro-2-methyl-benzofuran-4-yl, 2,3-dimethyl-benzofuran-4-yl, 2-trifluoromethyl-benzofuran-4-yl, 7-trifluoromethyl-benzofuran-4-yl, 2-methyl-6-trifluoromethyl-benzofuran-4-yl, and 2-methyl-7-trifluoromethyl-benzofuran-4-yl.

ii) A further embodiment of the invention relates to thiazolidine derivatives of formula (I) according to embodiment i), wherein the stereogenic center at the thiazolidine ring is in (R)-configuration.

iii) A further embodiment of the invention relates to thiazolidine derivatives according to any one of embodiments i) or ii), wherein A represents

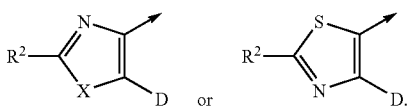

iv) A further embodiment of the invention relates to thiazolidine derivatives according to any one of embodiments i) to iii), wherein
A represents

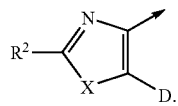

v) A further embodiment of the invention relates to thiazolidine derivatives according to any one of embodiments i) to iv), wherein
X represents S.

vi) A further embodiment of the invention relates to thiazolidine derivatives according to any one of embodiments i) to iv), wherein
X represents O.

vii) A further embodiment of the invention relates to thiazolidine derivatives according to any one of embodiments i) to vi), wherein
$R^2$ represents methyl.

viii) A further embodiment of the invention relates to thiazolidine derivatives according to embodiments i) or ii), wherein
A represents

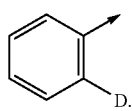

ix) A further embodiment of the invention relates to thiazolidine derivatives according to any one of embodiments i) to viii), wherein D represents unsubstituted, mono-, di-, or tri-substituted phenyl, wherein the substituents are independently selected from the group consisting of $(C_{1-4})$alkyl, $(C_{1-4})$alkoxy, trifluoromethyl, and halogen.

x) A further embodiment of the invention relates to thiazolidine derivatives according to any one of embodiments i) to ix), wherein
$R^1$ represents aryl, wherein the aryl group is selected from the group consisting of a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, and a 3,4-dihydro-2H-benzo[1,4]oxazinyl group, wherein said groups are unsubstituted, mono-, or di-substituted wherein the substituents are independently selected from the group consisting of $(C_{1-4})$alkyl, $(C_{1-4})$alkoxy and halogen;
or $R^1$ represents heteroaryl, which is unsubstituted, mono-, di, or tri-substituted, wherein the substituents are independently selected from the group consisting of $(C_{1-4})$alkyl, $(C_{1-4})$alkoxy, halogen, hydroxy-$(C_{1-4})$alkyl, and trifluoromethyl.

xi) A further embodiment of the invention relates to thiazolidine derivatives according to any one of embodiments i) to x), wherein $R^1$ represents heteroaryl, wherein said hetereroaryl is selected from the group consisting of thienyl, thiazolyl, pyrazolyl, pyridyl, indolyl, benzofuranyl, indazolyl, benzoxazolyl, benzisoxazolyl, benzothiazolyl, benzoxadiazolyl, benzothiadiazolyl, imidazo[1,2-a]pyridyl, imidazo[2,1-b]thiazolyl, benzoisothiazolyl, and pyrrolo[2,1-b]thiazolyl, wherein said groups are unsubstituted, mono-, di-, or tri-substituted (preferred unsubstituted, mono-, or di-substituted), wherein the substituents are independently selected from the group consisting of $(C_{1-4})$alkyl, $(C_{1-4})$alkoxy, halogen, hydroxy-$(C_{1-4})$alkyl, and trifluoromethyl.

xii) A further embodiment of the invention relates to thiazolidine derivatives according to any one of embodiments i) to x), wherein $R^1$ represents heteroaryl, wherein said hetereroaryl is selected from the group consisting of benzisoxazolyl, benzoxadiazolyl, benzothiadiazolyl, imidazo[1,2-a]pyridyl, imidazo[2,1-b]thiazolyl, benzoisothiazolyl, and pyrrolo[2,1-b]thiazolyl, wherein said groups are unsubstituted, mono-, or di-substituted wherein the substituents are independently selected from the group consisting of $(C_{1-4})$alkyl, $(C_{1-4})$alkoxy, halogen, and trifluoromethyl.

xiii) A further embodiment of the invention relates to thiazolidine derivatives according to any one of embodiments i) to xi), wherein, in case $R^1$ represents heteroaryl, it represents a group selected from

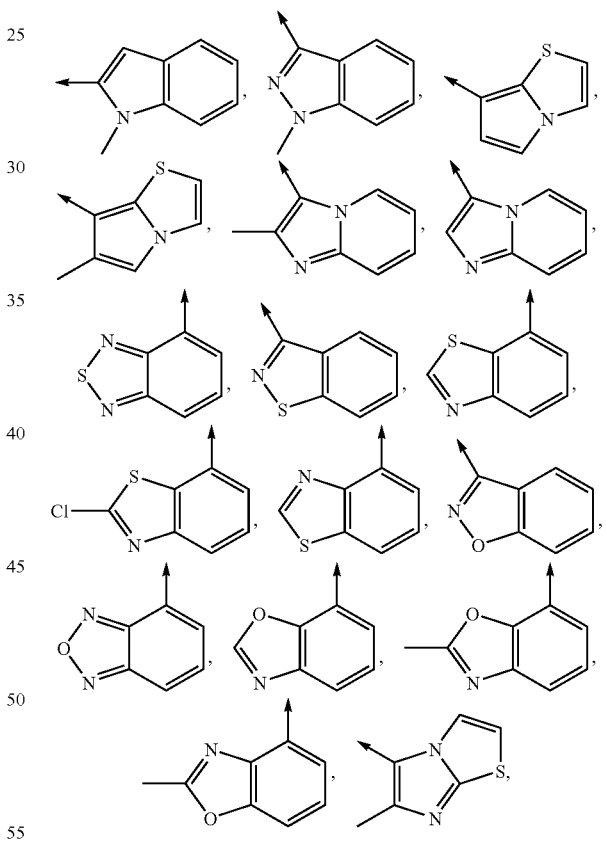

and benzofuranyl which is unsubstituted, mono, or di-substituted wherein the substituents are independently selected from $(C_{1-4})$alkyl, halogen, hydroxy-$(C_{1-4})$alkyl, and trifluoromethyl.

xiv) A further embodiment of the invention relates to thiazolidine derivatives according to any one of embodiments i) to xi), wherein $R^1$ represents heteroaryl, wherein said hetereroaryl is selected from the group consisting of thienyl, pyridyl, indolyl, benzofuranyl, indazolyl, and imidazo[2,1-b]thiazolyl, wherein said groups are unsubstituted, mono-, di-, or tri-substituted wherein the substituents are independently selected from the group consisting of $(C_{1-4})$alkyl, $(C_{1-4})$alkoxy, halogen, and trifluoromethyl.

xv) A further embodiment of the invention relates to thiazolidine derivatives according to any one of embodiments i) to ix), wherein $R^1$ represents a naphthyl- or a phenyl group (preferred) which is unsubstituted, mono-, di-, or tri-substituted (preferred: mono-substituted), wherein the substituents are independently selected from the group consisting of $(C_{1-4})$alkyl, $(C_{1-4})$alkoxy, trifluoromethyl, halogen and nitro (especially from $(C_{1-4})$alkyl, $(C_{1-4})$alkoxy, halogen, and trifluoromethyl (preferred: halogen)).

xvi) A further embodiment of the invention relates to thiazolidine derivatives according to any one of embodiments i) to x), wherein
$R^1$ represents aryl, wherein the aryl group is selected from the group consisting of a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, and a 3,4-dihydro-2H-benzo[1,4]oxazinyl group, wherein said groups are unsubstituted, mono-, or di-substituted wherein the substituents are independently selected from the group consisting of $(C_{1-4})$alkyl, $(C_{1-4})$alkoxy and halogen.

xvii) A further embodiment of the invention relates to thiazolidine derivatives according to any one of embodiments i) to x) or xvi), wherein, in case $R^1$ represents an aryl group, said aryl group is selected from the group consisting of a 2,3-dihydro-benzofuranyl-, a 2,3-dihydro-benzo[1,4]dioxinyl-, a chromanyl-, and a 3,4-dihydro-2H-benzo[1,4]oxazinyl group, wherein said groups are unsubstituted, mono-, or di-substituted wherein the substituents are independently selected from the group consisting of $(C_{1-4})$alkyl, $(C_{1-4})$alkoxy and halogen.

xviii) A further embodiment of the invention relates to thiazolidine derivatives according to any one of embodiments i) to x), or xvi), wherein, in case $R^1$ represents an aryl group, said aryl group is selected from the group consisting of a 2,3-dihydro-benzofuranyl-, a benzo[1,3]dioxolyl-, a 2,3-dihydro-benzo[1,4]dioxinyl-, or a 4H-benzo[1,3]dioxinyl group, wherein said groups are unsubstituted.

xix) A further embodiment of the invention relates to thiazolidine derivatives according to any one of embodiments i) to xi), wherein $R^1$ represents a group selected from

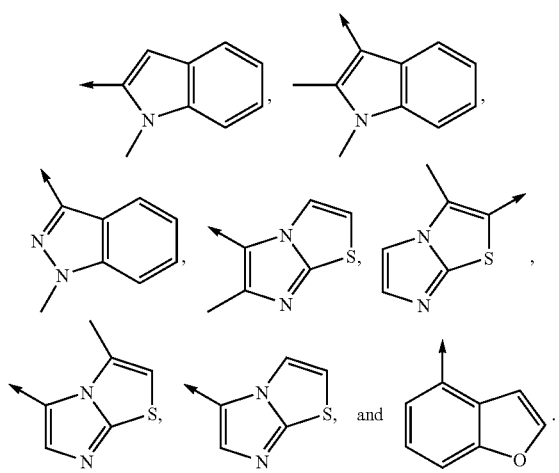

xx) A further embodiment of the invention relates to thiazolidine derivatives according to any one of embodiments i) to xi), wherein $R^1$ represents a group selected from

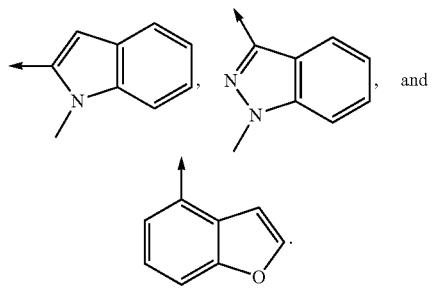

xxi) A further embodiment of the invention relates to thiazolidine derivatives according to any one of embodiments i) to xi), wherein $R^1$ represents a group selected from

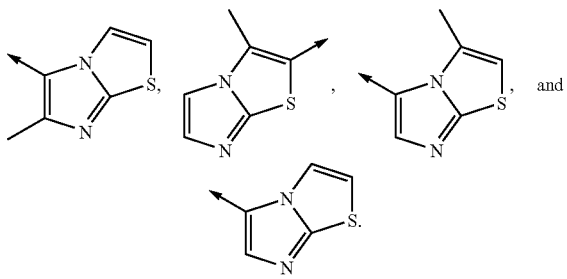

xxii) A further embodiment of the invention relates to thiazolidine derivatives according to any one of embodiments i) to xi) or xxi), wherein $R^1$ represents

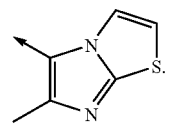

xxiii) A further embodiment of the invention relates to thiazolidine derivatives of formula (I) according to embodiments i) or ii) wherein
A represents

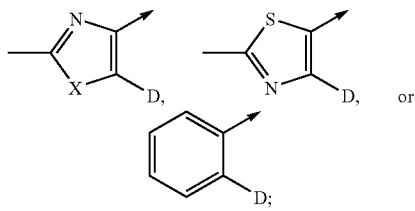

X represents S, or O;
D represents unsubstituted, mono-, or di-substituted phenyl, wherein the substituents are independently selected from the group consisting of $(C_{1-4})$alkyl, $(C_{1-4})$alkoxy, trifluoromethyl, and halogen; and
$R^1$ represents a group selected from 2,3-dihydro-benzofuran-4-yl, 2,3-dihydro-benzofuran-7-yl, 7-chloro-2-methoxy-2,3-dihydro-benzofuran-4-yl, 2,3-dihydro-benzo[1,4]dioxin-5-yl, chroman-5-yl, chroman-8-yl, 3,4-dihydro-2H-benzo[1,4]oxazin-5-yl, 4-methyl-3,4-dihydro-2H-benzo[1,4]oxazine-5-yl, 3,4-dihydro-2H-benzo[1,4]oxazin-8-yl, and 4-methyl-3,4-dihydro-2H-benzo[1,4]oxazine-8-yl;

or R¹ represents a group selected from

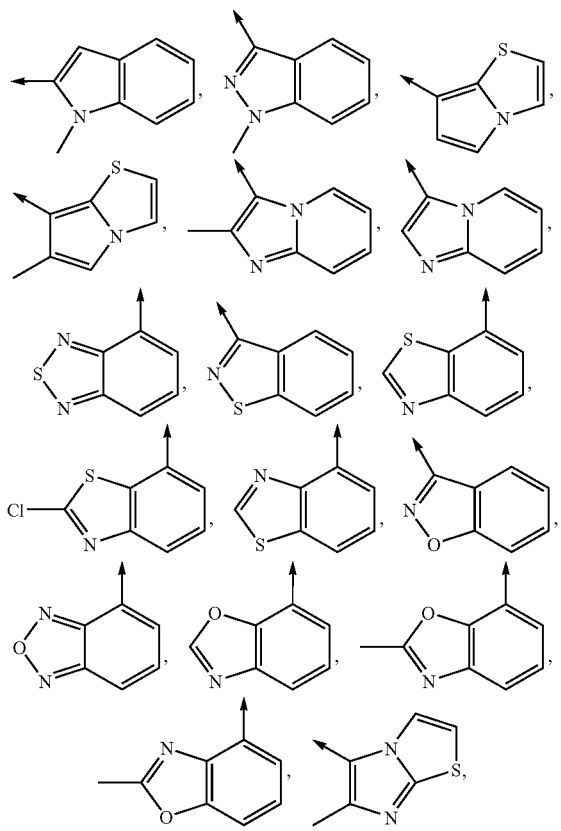

and benzofuranyl which is unsubstituted, mono, or di-substituted wherein the substituents are independently selected from (C$_{1-4}$)alkyl, halogen, hydroxy-(C$_{1-4}$)alkyl, and trifluoromethyl;
or R¹ represents phenyl which is mono-substituted with halogen or nitro, naphthyl, pyridyl which is mono-substituted with halogen, thienyl which is mono-substituted with halogen, thiazolyl which is disubstituted with (C$_{1-4}$)alkyl, or pyrazolyl which is disubstituted with (C$_{1-4}$)alkyl
(especially R¹ represents

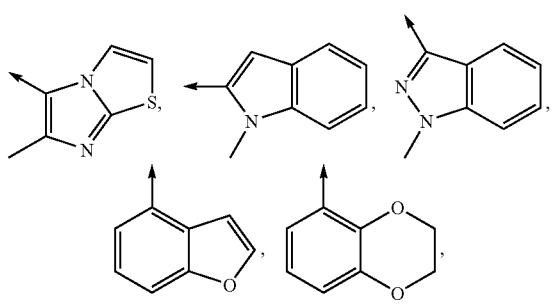

phenyl which is mono-substituted with halogen, pyridyl which is mono-substituted with halogen, or thienyl which is mono-substituted with halogen).

The compounds of formula (I) may contain one or more stereogenic or asymmetric centers, such as one or more asymmetric carbon atoms. Substituents at a double bond may be present in the Z- or E-configuration unless indicated otherwise. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to a compound of formula (I) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Examples of preferred compounds of formula (I) according to embodiment i) are selected from the group consisting of:
Benzofuran-4-carboxylic acid {(R)-3-[5-(4-fluoro-phenyl)-2-methyl-thiazole-4-carbonyl]-thiazolidin-4-ylmethyl}-amide;
Benzofuran-4-carboxylic acid {(R)-3-[5-(2-fluoro-phenyl)-2-methyl-thiazole-4-carbonyl]-thiazolidin-4-ylmethyl}-amide;
Benzofuran-4-carboxylic acid {(R)-3-[5-(3-methoxy-phenyl)-2-methyl-thiazole-4-carbonyl]-thiazolidin-4-ylmethyl}-amide;
Benzofuran-4-carboxylic acid {(R)-3-[2-methyl-5-(3-trifluoromethyl-phenyl)-thiazole-4-carbonyl]-thiazolidin-4-ylmethyl}-amide;
Benzofuran-4-carboxylic acid {(R)-3-[5-(3,4-difluoro-phenyl)-2-methyl-thiazole-4-carbonyl]-thiazolidin-4-ylmethyl}-amide;
Benzofuran-4-carboxylic acid {(R)-3-[5-(2-methoxy-phenyl)-2-methyl-thiazole-4-carbonyl]-thiazolidin-4-ylmethyl}-amide;
Benzofuran-4-carboxylic acid {(R)-3-[2-methyl-5-(3-trifluoromethyl-phenyl)-oxazole-4-carbonyl]-thiazolidin-4-ylmethyl}-amide;
Benzofuran-4-carboxylic acid [(R)-3-(2-methyl-5-p-tolyl-oxazole-4-carbonyl)-thiazolidin-4-ylmethyl]-amide;
Benzofuran-4-carboxylic acid {(R)-3-[5-(4-fluoro-phenyl)-2-methyl-oxazole-4-carbonyl]-thiazolidin-4-ylmethyl}-amide;
Benzofuran-4-carboxylic acid [(R)-3-(2-methyl-4-p-tolyl-thiazole-5-carbonyl)-thiazolidin-4-ylmethyl]-amide;
Benzofuran-4-carboxylic acid [(R)-3-(2-methyl-5-m-tolyl-oxazole-4-carbonyl)-thiazolidin-4-ylmethyl]-amide;
Benzofuran-4-carboxylic acid {(R)-3-[5-(3,4-dichloro-phenyl)-2-methyl-thiazole-4-carbonyl]-thiazolidin-4-ylmethyl}-amide;
Benzofuran-4-carboxylic acid {(R)-3-[5-(4-methoxy-phenyl)-2-methyl-oxazole-4-carbonyl]-thiazolidin-4-ylmethyl}-amide;
Benzofuran-4-carboxylic acid [(R)-3-(4'-methyl-biphenyl-2-carbonyl)-thiazolidin-4-ylmethyl]-amide;
Benzofuran-4-carboxylic acid [(R)-3-(3',4'-dimethyl-biphenyl-2-carbonyl)-thiazolidin-4-ylmethyl]-amide;
Benzofuran-4-carboxylic acid [(R)-3-(3'-methyl-biphenyl-2-carbonyl)-thiazolidin-4-ylmethyl]-amide;
Benzofuran-4-carboxylic acid [(R)-3-(3'-methoxy-biphenyl-2-carbonyl)-thiazolidin-4-ylmethyl]-amide;
Benzofuran-4-carboxylic acid [(R)-3-(4'-fluoro-biphenyl-2-carbonyl)-thiazolidin-4-ylmethyl]-amide;
Benzofuran-4-carboxylic acid [(R)-3-(4'-methoxy-biphenyl-2-carbonyl)-thiazolidin-4-ylmethyl]-amide;

2,3-Dihydro-benzo[1,4]dioxine-5-carboxylic acid {(R)-3-[5-(4-fluoro-phenyl)-2-methyl-thiazole-4-carbonyl]-thiazolidin-4-ylmethyl}-amide;

1-Methyl-1H-indazole-3-carboxylic acid {(R)-3-[5-(4-fluoro-phenyl)-2-methyl-thiazole-4-carbonyl]-thiazolidin-4-ylmethyl}-amide;

Benzofuran-4-carboxylic acid [(R)-3-(2-methyl-5-phenyl-thiazole-4-carbonyl)-thiazolidin-4-ylmethyl]-amide;

1-Methyl-1H-indazole-3-carboxylic acid [(R)-3-(2-methyl-5-phenyl-thiazole-4-carbonyl)-thiazolidin-4-ylmethyl]-amide;

1-Methyl-1H-indazole-3-carboxylic acid [(R)-3-(2-methyl-5-p-tolyl-thiazole-4-carbonyl)-thiazolidin-4-ylmethyl]-amide;

1-Methyl-1H-indazole-3-carboxylic acid {(R)-3-[2-methyl-5-(4-trifluoromethyl-phenyl)-thiazole-4-carbonyl]-thiazolidin-4-ylmethyl}-amide;

1-Methyl-1H-indazole-3-carboxylic acid {(R)-3-[5-(3-fluoro-phenyl)-2-methyl-thiazole-4-carbonyl]-thiazolidin-4-ylmethyl}-amide;

1-Methyl-1H-indazole-3-carboxylic acid {(R)-3-[5-(3,4-dimethyl-phenyl)-2-methyl-thiazole-4-carbonyl]-thiazolidin-4-ylmethyl}-amide;

1-Methyl-1H-indazole-3-carboxylic acid {(R)-3-[5-(2-fluoro-phenyl)-2-methyl-thiazole-4-carbonyl]-thiazolidin-4-ylmethyl}-amide;

1-Methyl-1H-indazole-3-carboxylic acid {(R)-3-[5-(3-methoxy-phenyl)-2-methyl-thiazole-4-carbonyl]-thiazolidin-4-ylmethyl}-amide;

1-Methyl-1H-indazole-3-carboxylic acid {(R)-3-[2-methyl-5-(3-trifluoromethyl-phenyl)-thiazole-4-carbonyl]-thiazolidin-4-ylmethyl}-amide;

1-Methyl-1H-indazole-3-carboxylic acid {(R)-3-[5-(3,4-difluoro-phenyl)-2-methyl-thiazole-4-carbonyl]-thiazolidin-4-ylmethyl}-amide;

Benzofuran-4-carboxylic acid [(R)-3-(2-methyl-5-p-tolyl-thiazole-4-carbonyl)-thiazolidin-4-ylmethyl]-amide;

1-Methyl-1H-indazole-3-carboxylic acid {(R)-3-[5-(2-methoxy-phenyl)-2-methyl-thiazole-4-carbonyl]-thiazolidin-4-ylmethyl}-amide;

1-Methyl-1H-indazole-3-carboxylic acid {(R)-3-[2-methyl-5-(3-trifluoromethyl-phenyl)-oxazole-4-carbonyl]-thiazolidin-4-ylmethyl}-amide;

1-Methyl-1H-indazole-3-carboxylic acid [(R)-3-(2-methyl-5-p-tolyl-oxazole-4-carbonyl)-thiazolidin-4-ylmethyl]-amide;

1-Methyl-1H-indazole-3-carboxylic acid {(R)-3-[5-(4-fluoro-phenyl)-2-methyl-oxazole-4-carbonyl]-thiazolidin-4-ylmethyl}-amide;

1-Methyl-1H-indazole-3-carboxylic acid [(R)-3-(2-methyl-4-p-tolyl-thiazole-5-carbonyl)-thiazolidin-4-ylmethyl]-amide;

1-Methyl-1H-indazole-3-carboxylic acid [(R)-3-(2-methyl-5-m-tolyl-oxazole-4-carbonyl)-thiazolidin-4-ylmethyl]-amide;

1-Methyl-1H-indazole-3-carboxylic acid {(R)-3-[5-(3,4-dichloro-phenyl)-2-methyl-thiazole-4-carbonyl]-thiazolidin-4-ylmethyl}-amide;

1-Methyl-1H-indazole-3-carboxylic acid {(R)-3-[5-(4-methoxy-phenyl)-2-methyl-oxazole-4-carbonyl]-thiazolidin-4-ylmethyl}-amide;

1-Methyl-1H-indazole-3-carboxylic acid [(R)-3-(4'-methyl-biphenyl-2-carbonyl)-thiazolidin-4-ylmethyl]-amide;

1-Methyl-1H-indazole-3-carboxylic acid [(R)-3-(3',4'-dimethyl-biphenyl-2-carbonyl)-thiazolidin-4-ylmethyl]-amide;

Benzofuran-4-carboxylic acid {(R)-3-[2-methyl-5-(4-trifluoromethyl-phenyl)-thiazole-4-carbonyl]-thiazolidin-4-ylmethyl}-amide;

1-Methyl-1H-indazole-3-carboxylic acid [(R)-3-(3'-methyl-biphenyl-2-carbonyl)-thiazolidin-4-ylmethyl]-amide;

1-Methyl-1H-indazole-3-carboxylic acid [(R)-3-(3'-methoxy-biphenyl-2-carbonyl)-thiazolidin-4-ylmethyl]-amide;

1-Methyl-1H-indazole-3-carboxylic acid [(R)-3-(4'-fluoro-biphenyl-2-carbonyl)-thiazolidin-4-ylmethyl]-amide;

1-Methyl-1H-indazole-3-carboxylic acid [(R)-3-(4'-methoxy-biphenyl-2-carbonyl)-thiazolidin-4-ylmethyl]-amide;

3-Bromo-N-{(R)-3-[5-(4-fluoro-phenyl)-2-methyl-thiazole-4-carbonyl]-thiazolidin-4-ylmethyl}-benzamide;

1-Methyl-1H-indole-2-carboxylic acid {(R)-3-[5-(4-fluoro-phenyl)-2-methyl-thiazole-4-carbonyl]-thiazolidin-4-ylmethyl}-amide;

4-Bromo-thiophene-2-carboxylic acid {(R)-3-[5-(4-fluoro-phenyl)-2-methyl-thiazole-4-carbonyl]-thiazolidin-4-ylmethyl}-amide;

6-Bromo-pyridine-2-carboxylic acid {(R)-3-[5-(4-fluoro-phenyl)-2-methyl-thiazole-4-carbonyl]-thiazolidin-4-ylmethyl}-amide;

2,3-Dihydro-benzo[1,4]dioxine-5-carboxylic acid [(R)-3-(biphenyl-2-carbonyl)-thiazolidin-4-ylmethyl]-amide;

Benzofuran-4-carboxylic acid [(R)-3-(biphenyl-2-carbonyl)-thiazolidin-4-ylmethyl]-amide;

Benzofuran-4-carboxylic acid {(R)-3-[5-(3-fluoro-phenyl)-2-methyl-thiazole-4-carbonyl]-thiazolidin-4-ylmethyl}-amide;

N-[(R)-3-(Biphenyl-2-carbonyl)-thiazolidin-4-ylmethyl]-3-bromo-benzamide;

1-Methyl-1H-indole-2-carboxylic acid [(R)-3-(biphenyl-2-carbonyl)-thiazolidin-4-ylmethyl]-amide;

1-Methyl-1H-indazole-3-carboxylic acid [(R)-3-(biphenyl-2-carbonyl)-thiazolidin-4-ylmethyl]-amide;

4-Bromo-thiophene-2-carboxylic acid [(R)-3-(biphenyl-2-carbonyl)-thiazolidin-4-ylmethyl]-amide;

6-Bromo-pyridine-2-carboxylic acid [(R)-3-(biphenyl-2-carbonyl)-thiazolidin-4-ylmethyl]-amide; and Benzofuran-4-carboxylic acid {(R)-3-[5-(3,4-dimethyl-phenyl)-2-methyl-thiazole-4-carbonyl]-thiazolidin-4-ylmethyl}-amide.

Further examples of preferred compounds of formula (I) according to embodiment i) are selected from the group consisting of:

Naphthalene-1-carboxylic acid {(R)-3-[5-(4-fluoro-phenyl)-2-methyl-thiazole-4-carbonyl]-thiazolidin-4-ylmethyl}-amide;

5-tert-Butyl-2-methyl-2H-pyrazole-3-carboxylic acid {(R)-3-[5-(4-fluoro-phenyl)-2-methyl-thiazole-4-carbonyl]-thiazolidin-4-ylmethyl}-amide;

2,3-Dihydro-benzofuran-7-carboxylic acid {(R)-3[5-(4-fluoro-phenyl)-2-methyl-thiazole-4-carbonyl]-thiazolidin-4-ylmethyl}-amide;

2,4-Dimethyl-thiazole-5-carboxylic acid {(R)-3-[5-(4-fluoro-phenyl)-2-methyl-thiazole-4-carbonyl]-thiazolidin-4-ylmethyl}-amide;

N-{(R)-3-[5-(4-fluoro-phenyl)-2-methyl-thiazole-4-carbonyl]-thiazolidin-4-ylmethyl}-3-nitro-benzamide; Benzo[b]thiophene-2-carboxylic acid {(R)-3-[5-(4-fluoro-phenyl)-2-methyl-thiazole-4-carbonyl]-thiazolidin-4-ylmethyl}-amide;

2-Methyl-benzofuran-4-carboxylic acid [(R)-3-(2-methyl-5-m-tolyl-thiazole-4-carbonyl)-thiazolidin-4-ylmethyl]-amide;

2-Methyl-benzooxazole-4-carboxylic acid [(R)-3-(2-methyl-5-m-tolyl-thiazole-4-carbonyl)-thiazolidin-4-ylmethyl]-amide;
Imidazo[1,2-a]pyridine-3-carboxylic acid [(R)-3-(2-methyl-5-m-tolyl-thiazole-4-carbonyl)-thiazolidin-4-ylmethyl]-amide;
2-Methyl-imidazo[1,2-a]pyridine-3-carboxylic acid [(R)-3-(2-methyl-5-m-tolyl-thiazole-4-carbonyl)-thiazolidin-4-ylmethyl]-amide;
2,3-Dimethyl-benzofuran-4-carboxylic acid [(R)-3-(2-methyl-5-m-tolyl-thiazole-4-carbonyl)-thiazolidin-4-ylmethyl]-amide;
3,4-Dihydro-2H-benzo[1,4]oxazine-5-carboxylic acid [(R)-3-(2-methyl-5-m-tolyl-thiazole-4-carbonyl)-thiazolidin-4-ylmethyl]-amide;
4-Methyl-3,4-Dihydro-2H-benzo[1,4]oxazine-5-carboxylic acid [(R)-3-(2-methyl-5-m-tolyl-thiazole-4-carbonyl)-thiazolidin-4-ylmethyl]-amide;
Chroman-5-carboxylic acid [(R)-3-(2-methyl-5-m-tolyl-thiazole-4-carbonyl)-thiazolidin-4-ylmethyl]-amide;
Chroman-8-carboxylic acid [(R)-3-(2-methyl-5-m-tolyl-thiazole-4-carbonyl)-thiazolidin-4-ylmethyl]-amide;
3,4-Dihydro-2H-benzo[1,4]oxazine-8-carboxylic acid [(R)-3-(2-methyl-5-m-tolyl-thiazole-4-carbonyl)-thiazolidin-4-ylmethyl]-amide;
4-Methyl-3,4-Dihydro-2H-benzo[1,4]oxazine-8-carboxylic acid [(R)-3-(2-methyl-5-m-tolyl-thiazole-4-carbonyl)-thiazolidin-4-ylmethyl]-amide;
Benzo[d]isoxazole-3-carboxylic acid [(R)-3-(2-methyl-5-m-tolyl-thiazole-4-carbonyl)-thiazolidin-4-ylmethyl]-amide;
Benzo[d]isothiazole-3-carboxylic acid [(R)-3-(2-methyl-5-m-tolyl-thiazole-4-carbonyl)-thiazolidin-4-ylmethyl]-amide;
1-Methyl-1H-indazole-3-carboxylic acid [(R)-3-(2-methyl-5-m-tolyl-thiazole-4-carbonyl)-thiazolidin-4-ylmethyl]-amide;
2,3-Dihydro-benzofuran-4-carboxylic acid [(R)-3-(2-methyl-5-m-tolyl-thiazole-4-carbonyl)-thiazolidin-4-ylmethyl]-amide;
2,3-Dihydro-benzo[1,4]dioxine-5-carboxylic acid [(R)-3-(2-methyl-5-m-tolyl-thiazole-4-carbonyl)-thiazolidin-4-ylmethyl]-amide;
2-Methyl-benzofuran-4-carboxylic acid {(R)-3-[5-(4-fluoro-phenyl)-2-methyl-thiazole-4-carbonyl]-thiazolidin-4-ylmethyl}-amide;
Imidazo[1,2-a]pyridine-3-carboxylic acid {(R)-3-[5-(4-fluoro-phenyl)-2-methyl-thiazole-4-carbonyl]-thiazolidin-4-ylmethyl}-amide;
2-Methyl-imidazo[1,2-a]pyridine-3-carboxylic acid {(R)-3-[5-(4-fluoro-phenyl)-2-methyl-thiazole-4-carbonyl]-thiazolidin-4-ylmethyl}-amide;
2,3-Dimethyl-benzofuran-4-carboxylic acid {(R)-3-[5-(4-fluoro-phenyl)-2-methyl-thiazole-4-carbonyl]-thiazolidin-4-ylmethyl}-amide;
3,4-Dihydro-2H-benzo[1,4]oxazine-5-carboxylic acid {(R)-3-[5-(4-fluoro-phenyl)-2-methyl-thiazole-4-carbonyl]-thiazolidin-4-ylmethyl}-amide;
4-Methyl-3,4-dihydro-2H-benzo[1,4]oxazine-5-carboxylic acid {(R)-3-[5-(4-fluoro-phenyl)-2-methyl-thiazole-4-carbonyl]-thiazolidin-4-ylmethyl}-amide;
Chroman-5-carboxylic acid {(R)-3-[5-(4-fluoro-phenyl)-2-methyl-thiazole-4-carbonyl]-thiazolidin-4-ylmethyl}-amide;
Chroman-8-carboxylic acid {(R)-3-[5-(4-fluoro-phenyl)-2-methyl-thiazole-4-carbonyl]-thiazolidin-4-ylmethyl}-amide;
3,4-Dihydro-2H-benzo[1,4]oxazine-8-carboxylic acid {(R)-3-[5-(4-fluoro-phenyl)-2-methyl-thiazole-4-carbonyl]-thiazolidin-4-ylmethyl}-amide;
4-Methyl-3,4-dihydro-2H-benzo[1,4]oxazine-8-carboxylic acid {(R)-3-[5-(4-fluoro-phenyl)-2-methyl-thiazole-4-carbonyl]-thiazolidin-4-ylmethyl}-amide;
2,3-Dihydro-benzofuran-4-carboxylic acid {(R)-3-[5-(4-fluoro-phenyl)-2-methyl-thiazole-4-carbonyl]-thiazolidin-4-ylmethyl}-amide;
Benzooxazole-7-carboxylic acid [(R)-3-(2-methyl-5-m-tolyl-thiazole-4-carbonyl)-thiazolidin-4-ylmethyl]-amide;
Benzooxazole-7-carboxylic acid {(R)-3-[5-(4-fluoro-phenyl)-2-methyl-thiazole-4-carbonyl]-thiazolidin-4-ylmethyl}-amide;
2-Methyl-benzooxazole-7-carboxylic acid [(R)-3-(2-methyl-5-m-tolyl-thiazole-4-carbonyl)-thiazolidin-4-ylmethyl]-amide;
2-Methyl-benzooxazole-7-carboxylic acid {(R)-3-[5-(4-fluoro-phenyl)-2-methyl-thiazole-4-carbonyl]-thiazolidin-4-ylmethyl}-amide;
Benzothiazole-7-carboxylic acid [(R)-3-(2-methyl-5-m-tolyl-thiazole-4-carbonyl)-thiazolidin-4-ylmethyl]-amide;
Benzothiazole-7-carboxylic acid {(R)-3-[5-(4-fluoro-phenyl)-2-methyl-thiazole-4-carbonyl]-thiazolidin-4-ylmethyl}-amide;
7-Chloro-benzofuran-4-carboxylic acid [(R)-3-(2-methyl-5-m-tolyl-thiazole-4-carbonyl)-thiazolidin-4-ylmethyl]-amide;
7-Chloro-benzofuran-4-carboxylic acid {(R)-3-[5-(4-fluoro-phenyl)-2-methyl-thiazole-4-carbonyl]-thiazolidin-4-ylmethyl}-amide;
7-Fluoro-benzofuran-4-carboxylic acid [(R)-3-(2-methyl-5-m-tolyl-thiazole-4-carbonyl)-thiazolidin-4-ylmethyl]-amide;
7-Fluoro-benzofuran-4-carboxylic acid {(R)-3-[5-(4-fluoro-phenyl)-2-methyl-thiazole-4-carbonyl]-thiazolidin-4-ylmethyl}-amide;
Pyrrolo[2,1-b]thiazole-7-carboxylic acid [(R)-3-(2-methyl-5-m-tolyl-thiazole-4-carbonyl)-thiazolidin-4-ylmethyl]-amide;
Pyrrolo[2,1-b]thiazole-7-carboxylic acid {(R)-3-[5-(4-fluoro-phenyl)-2-methyl-thiazole-4-carbonyl]-thiazolidin-4-ylmethyl}-amide;
6-Methyl-pyrrolo[2,1-b]thiazole-7-carboxylic acid [(R)-3-(2-methyl-5-m-tolyl-thiazole-4-carbonyl)-thiazolidin-4-ylmethyl]-amide;
6-Methyl-pyrrolo[2,1-b]thiazole-7-carboxylic acid {(R)-3-[5-(4-fluoro-phenyl)-2-methyl-thiazole-4-carbonyl]-thiazolidin-4-ylmethyl}-amide;
7-Chloro-2-methoxy-2,3-dihydro-benzofuran-4-carboxylic acid [(R)-3-(2-methyl-5-m-tolyl-thiazole-4-carbonyl)-thiazolidin-4-ylmethyl]-amide;
7-Chloro-2-methoxy-2,3-dihydro-benzofuran-4-carboxylic acid {(R)-3-[5-(4-fluoro-phenyl)-2-methyl-thiazole-4-carbonyl]-thiazolidin-4-ylmethyl}-amide;
2-Chloro-benzothiazole-4-carboxylic acid [(R)-3-(2-methyl-5-m-tolyl-thiazole-4-carbonyl)-thiazolidin-4-ylmethyl]-amide;
2-Chloro-benzothiazole-4-carboxylic acid {(R)-3-[5-(4-fluoro-phenyl)-2-methyl-thiazole-4-carbonyl]-thiazolidin-4-ylmethyl}-amide;
Benzothiazole-4-carboxylic acid [(R)-3-(2-methyl-5-m-tolyl-thiazole-4-carbonyl)-thiazolidin-4-ylmethyl]-amide;

Benzothiazole-4-carboxylic acid {(R)-3-[5-(4-fluoro-phenyl)-2-methyl-thiazole-4-carbonyl]-thiazolidin-4-ylmethyl}-amide;
Benzo[2,1,3]thiadiazole-4-carboxylic acid [(R)-3-(2-methyl-5-m-tolyl-thiazole-4-carbonyl)-thiazolidin-4-ylmethyl]-amide;
Benzo[2,1,3]thiadiazole-4-carboxylic acid {(R)-3-[5-(4-fluoro-phenyl)-2-methyl-thiazole-4-carbonyl]-thiazolidin-4-ylmethyl}-amide;
7-Trifluoromethyl-benzofuran-4-carboxylic acid [(R)-3-(2-methyl-5-m-tolyl-thiazole-4-carbonyl)-thiazolidin-4-ylmethyl]-amide;
7-Trifluoromethyl-benzofuran-4-carboxylic acid {(R)-3-[5-(4-fluoro-phenyl)-2-methyl-thiazole-4-carbonyl]-thiazolidin-4-ylmethyl}-amide;
3-Methyl-benzofuran-4-carboxylic acid [(R)-3-(2-methyl-5-m-tolyl-thiazole-4-carbonyl)-thiazolidin-4-ylmethyl]-amide;
3-Methyl-benzofuran-4-carboxylic acid {(R)-3-[5-(4-fluoro-phenyl)-2-methyl-thiazole-4-carbonyl]-thiazolidin-4-ylmethyl}-amide;
Benzo[2,1,3]oxadiazole-4-carboxylic acid [(R)-3-(2-methyl-5-m-tolyl-thiazole-4-carbonyl)-thiazolidin-4-ylmethyl]-amide;
Benzo[2,1,3]oxadiazole-4-carboxylic acid {(R)-3-[5-(4-fluoro-phenyl)-2-methyl-thiazole-4-carbonyl]-thiazolidin-4-ylmethyl}-amide;
2-Hydroxymethyl-benzofuran-4-carboxylic acid [(R)-3-(2-methyl-5-m-tolyl-thiazole-4-carbonyl)-thiazolidin-4-ylmethyl]-amide;
2-Hydroxymethyl-benzofuran-4-carboxylic acid {(R)-3-[5-(4-fluoro-phenyl)-2-methyl-thiazole-4-carbonyl]-thiazolidin-4-ylmethyl}-amide;
2-Methyl-benzofuran-4-carboxylic acid [(R)-3-(2-methyl-5-m-tolyl-thiazole-4-carbonyl)-thiazolidin-4-ylmethyl]-amide;
5-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide;
7-Chloro-2-methyl-benzofuran-4-carboxylic acid [(R)-3-(2-methyl-5-m-tolyl-thiazole-4-carbonyl)-thiazolidin-4-ylmethyl]-amide;
7-Fluoro-2-methyl-benzofuran-4-carboxylic acid [(R)-3-(2-methyl-5-m-tolyl-thiazole-4-carbonyl)-thiazolidin-4-ylmethyl]-amide;
2-Methyl-7-trifluoromethyl-benzofuran-4-carboxylic acid [(R)-3-(2-methyl-5-m-tolyl-thiazole-4-carbonyl)-thiazolidin-4-ylmethyl]-amide;
6-Chloro-2-methyl-benzofuran-4-carboxylic acid [(R)-3-(2-methyl-5-m-tolyl-thiazole-4-carbonyl)-thiazolidin-4-ylmethyl]-amide;
6-Fluoro-2-methyl-benzofuran-4-carboxylic acid [(R)-3-(2-methyl-5-m-tolyl-thiazole-4-carbonyl)-thiazolidin-4-ylmethyl]-amide;
2-Methyl-6-trifluoromethyl-benzofuran-4-carboxylic acid [(R)-3-(2-methyl-5-m-tolyl-thiazole-4-carbonyl)-thiazolidin-4-ylmethyl]-amide;
5-Chloro-2-methyl-benzofuran-4-carboxylic acid [(R)-3-(2-methyl-5-m-tolyl-thiazole-4-carbonyl)-thiazolidin-4-ylmethyl]-amide;
7-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide;
7-Fluoro-2-methyl-benzofuran-4-carboxylic acid {(R)-3-[5-(4-fluoro-phenyl)-2-methyl-thiazole-4-carbonyl]-thiazolidin-4-ylmethyl}-amide;
2-Methyl-7-trifluoromethyl-benzofuran-4-carboxylic acid {(R)-3-[5-(4-fluoro-phenyl)-2-methyl-thiazole-4-carbonyl]thiazolidin-4-ylmethyl}-amide;
6-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide;
6-Fluoro-2-methyl-benzofuran-4-carboxylic acid {(R)-3-[5-(4-fluoro-phenyl)-2-methyl-thiazole-4-carbonyl]-thiazolidin-4-ylmethyl}-amide;
2-Methyl-6-trifluoromethyl-benzofuran-4-carboxylic acid {(R)-3-[5-(4-fluoro-phenyl)-2-methyl-thiazole-4-carbonyl]-thiazolidin-4-ylmethyl}-amide; and
2-Trifluoromethyl-benzofuran-4-carboxylic acid [3-(2-methyl-5-m-tolyl-thiazole-4-carbonyl)-thiazolidin-4-ylmethyl]-amide.

Further examples of preferred compounds of formula (I) according to embodiment i) are selected from the group consisting of:

6-Methyl-imidazo[2,1-b]thiazole-5-carboxylic acid {(R)-3-[5-(4-fluoro-phenyl)-2-methyl-thiazole-4-carbonyl]-thiazolidin-4-ylmethyl}-amide;
6-Methyl-imidazo[2,1-b]thiazole-5-carboxylic acid [(R)-3-(2-methyl-5-phenyl-thiazole-4-carbonyl)-thiazolidin-4-ylmethyl]-amide;
6-Methyl-imidazo[2,1-b]thiazole-5-carboxylic acid [(R)-3-(2-methyl-5-p-tolyl-thiazole-4-carbonyl)-thiazolidin-4-ylmethyl]-amide;
6-Methyl-imidazo[2,1-b]thiazole-5-carboxylic acid {(R)-3-[2-methyl-5-(4-trifluoromethyl-phenyl)-thiazole-4-carbonyl]-thiazolidin-4-ylmethyl}-amide;
6-Methyl-imidazo[2,1-b]thiazole-5-carboxylic acid {(R)-3-[5-(3-fluoro-phenyl)-2-methyl-thiazole-4-carbonyl]thiazolidin-4-ylmethyl}-amide;
6-Methyl-imidazo[2,1-b]thiazole-5-carboxylic acid {(R)-3-[5-(3,4-dimethyl-phenyl)-2-methyl-thiazole-4-carbonyl]-thiazolidin-4-ylmethyl}-amide;
6-Methyl-imidazo[2,1-b]thiazole-5-carboxylic acid {(R)-3-[5-(2-fluoro-phenyl)-2-methyl-thiazole-4-carbonyl]-thiazolidin-4-ylmethyl}-amide;
6-Methyl-imidazo[2,1-b]thiazole-5-carboxylic acid {(R)-3-[5-(3-methoxy-phenyl)-2-methyl-thiazole-4-carbonyl]-thiazolidin-4-ylmethyl}-amide;
6-Methyl-imidazo[2,1-b]thiazole-5-carboxylic acid {(R)-3-[2-methyl-5-(3-trifluoromethyl-phenyl)-thiazole-4-carbonyl]-thiazolidin-4-ylmethyl}-amide;
6-Methyl-imidazo[2,1-b]thiazole-5-carboxylic acid {(R)-3-[5-(3,4-difluoro-phenyl)-2-methyl-thiazole-4-carbonyl]-thiazolidin-4-ylmethyl}-amide;
6-Methyl-imidazo[2,1-b]thiazole-5-carboxylic acid {(R)-3-[5-(2-methoxy-phenyl)-2-methyl-thiazole-4-carbonyl]-thiazolidin-4-ylmethyl}-amide;
6-Methyl-imidazo[2,1-b]thiazole-5-carboxylic acid {(R)-3-[2-methyl-5-(3-trifluoromethyl-phenyl)-oxazole-4-carbonyl]thiazolidin-4-ylmethyl}-amide;
6-Methyl-imidazo[2,1-b]thiazole-5-carboxylic acid [(R)-3-(2-methyl-5-p-tolyl-oxazole-4-carbonyl)-thiazolidin-4-ylmethyl]-amide;
6-Methyl-imidazo[2,1-b]thiazole-5-carboxylic acid {(R)-3-[5-(4-fluoro-phenyl)-2-methyl-oxazole-4-carbonyl]-thiazolidin-4-ylmethyl}-amide;
6-Methyl-imidazo[2,1-b]thiazole-5-carboxylic acid [(R)-3-(2-methyl-4-p-tolyl-thiazole-5-carbonyl)-thiazolidin-4-ylmethyl]-amide;
6-Methyl-imidazo[2,1-b]thiazole-5-carboxylic acid [(R)-3-(2-methyl-5-m-tolyl-oxazole-4-carbonyl)-thiazolidin-4-ylmethyl]-amide;

6-Methyl-imidazo[2,1-b]thiazole-5-carboxylic acid {(R)-3-[5-(3,4-dichloro-phenyl)-2-methyl-thiazole-4-carbonyl]-thiazolidin-4-ylmethyl}-amide;

6-Methyl-imidazo[2,1-b]thiazole-5-carboxylic acid {(R)-3-[5-(4-methoxy-phenyl)-2-methyl-oxazole-4-carbonyl]-thiazolidin-4-ylmethyl}-amide;

6-Methyl-imidazo[2,1-b]thiazole-5-carboxylic acid [(R)-3-(4'-methyl-biphenyl-2-carbonyl)-thiazolidin-4-ylmethyl]-amide;

6-Methyl-imidazo[2,1-b]thiazole-5-carboxylic acid [(R)-3-(3',4'-dimethyl-biphenyl-2-carbonyl)-thiazolidin-4-ylmethyl]-amide;

6-Methyl-imidazo[2,1-b]thiazole-5-carboxylic acid [(R)-3-(3'-methyl-biphenyl-2-carbonyl)-thiazolidin-4-ylmethyl]-amide;

6-Methyl-imidazo[2,1-b]thiazole-5-carboxylic acid [(R)-3-(3'-methoxy-biphenyl-2-carbonyl)-thiazolidin-4-ylmethyl]-amide;

6-Methyl-imidazo[2,1-b]thiazole-5-carboxylic acid [(R)-3-(4'-fluoro-biphenyl-2-carbonyl)-thiazolidin-4-ylmethyl]-amide;

6-Methyl-imidazo[2,1-b]thiazole-5-carboxylic acid [(R)-3-(4'-methoxy-biphenyl-2-carbonyl)-thiazolidin-4-ylmethyl]-amide; and 6-Methyl-imidazo[2,1-b]thiazole-5-carboxylic acid [(R)-3-(biphenyl-2-carbonyl)-thiazolidin-4-ylmethyl]-amide.

The compounds of formula (I) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I).

The compounds according to formula (I) may be used for the preparation of a medicament and are suitable for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

Compounds of formula (I) are particularly suitable for use in the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of formula (I) are particularly suitable for use in the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of formula (I) are particularly suitable for use in the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of formula (I) are particularly suitable for use in the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of formula (I) are particularly suitable for use in the treatment of diseases or disorders selected from the group consisting of psychoactive substance use and abuse that comprise all types of psychological or physical addictions and their related tolerance and dependence components.

Preparation of compounds of formula (I):

A further aspect of the invention is a process for the preparation of compounds of formula (I). Compounds according to formula (I) of the present invention can be prepared according to the general sequence of reactions outlined in the schemes below wherein A, D, X, $R^1$ and $R^2$ are as defined for formula (I). The compounds obtained may also be converted into pharmaceutically acceptable salts thereof in a manner known per se.

In general, all chemical transformations can be performed according to well-known standard methodologies as described in the literature or as described in the procedures below.

Scheme 1: Preparation of compounds of formula (I)

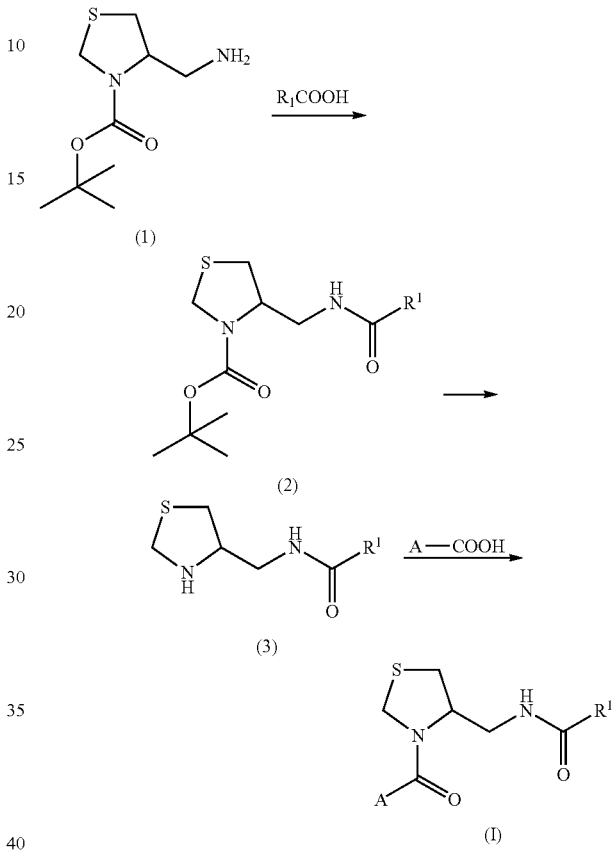

Thiazolidine derivatives of formula (I) may be prepared by reacting a thiazolidine derivative of structure (3) with an acid of the general formula A-COOH in a polar aprotic solvent such as DMF, THF, DCM at RT in the presence of a coupling reagent such as TBTU, EDC/HOAt, HATU in the presence of a base such as TEA, DIPEA, DMAP. Acids of the general formula A-COOH are commercially available or synthesized according to methods described below.

Thiazolidine derivates of structure (3) may be prepared by treatment of compounds of structure (2) with acids such as HCl in dioxane, TFA in DCM, neat TFA at RT. Compounds of structure (3) may be used as free base or salts thereof such as the hydrochloride salt.

A compound of structure (2) may be prepared by reacting 4-aminomethyl-thiazolidine-3-carboxylic acid tert-butyl ester of structure (1), which is commercially available, with an acid of the general formula $R^1$—COOH in a polar aprotic solvent such as DMF, THF, DCM at RT in the presence of a coupling reagent such as TBTU, EDC, HATU in presence or absence of additives such as HOBt, HOAt in the presence of a base such as TEA, DIPEA, DMAP. Acids of the general formula $R^1$COOH are commercially available, or synthesized according to methods described below.

Preparation of Carboxylic Acids A-COOH

Carboxylic acid derivatives A-COOH wherein A represents a thiazole-4-yl derivative are commercially available or can be synthesised according to scheme 2.

Scheme 2: Synthesis of carboxylic acids A—COOH wherein A represents a thiazole-4-yl derivative

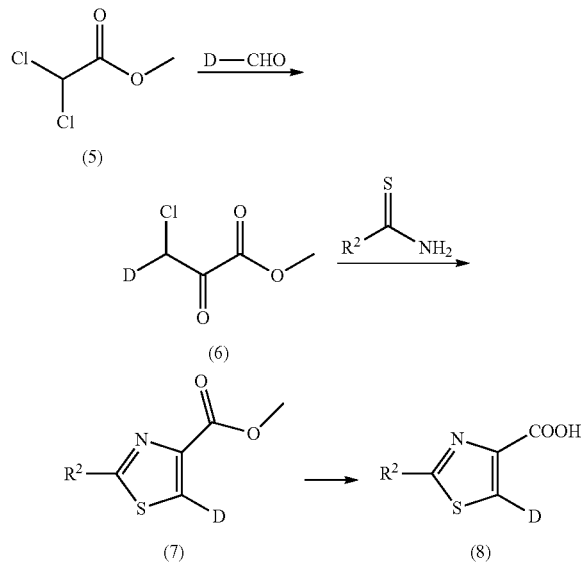

By reaction of methyl dichloroacetate (5) with an aldehyde of the formula D-CHO in the presence of a base such as KOtBu in an aprotic polar solvent such as THF at RT 3-chloro-2-oxo-propionic acid ester derivatives (6) are obtained. Compounds of structure (6) can be transformed by reaction with commercially available thioamides $R^2$—C(S)—$NH_2$ at RT in solvents such as MeCN to provide thiazol-4-carboxylic acid ester derivatives (7). Saponification of the ester function using methods known in the art such as treatment with a base such as sodium hydroxide in a solvent such as methanol provides the corresponding thiazol-4-carboxylic acid derivatives (8). Aldehydes of formula D-CHO are commercially available or well known in the art.

Carboxylic acid derivatives A-COOH wherein A represents a thiazole-5-yl derivative which are commercially available or synthesised according to scheme 3.

Scheme 3: Synthesis of carboxylic acids A—COOH wherein A represents a thiazole-5-yl derivative

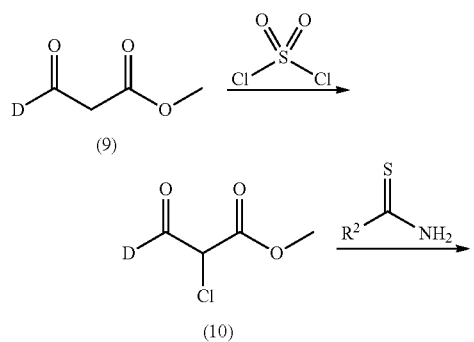

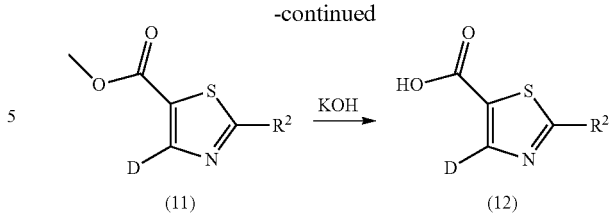

By refluxing a commercially available 3-oxo-propionic acid ester derivative (9) with $SO_2Cl_2$ in a solvent such as $CHCl_3$ the corresponding 2-chloro-3-oxo-propionic acid ester derivatives (10) can be obtained. Compounds of structure (10) can be transformed by reaction with commercially available thioamides $R^2$—C(S)—$NH_2$ at reflux temperature in solvents such as THF in presence of a base such as $NaHCO_3$ to the corresponding thiazol-5-carboxylic acid ester derivatives (11). Saponification of the ester function using methods known in the art such as treatment with a base such as KOH in a solvent such as ethanol provides the corresponding thiazol-5-carboxylic acid derivatives (12).

Carboxylic acid derivatives A-COOH wherein A represents a oxazole-4-yl derivative which are commercially available or synthesised according to scheme 4.

Scheme 4: Synthesis of carboxylic acids A—COOH wherein A represents an oxazole-4-yl derivative

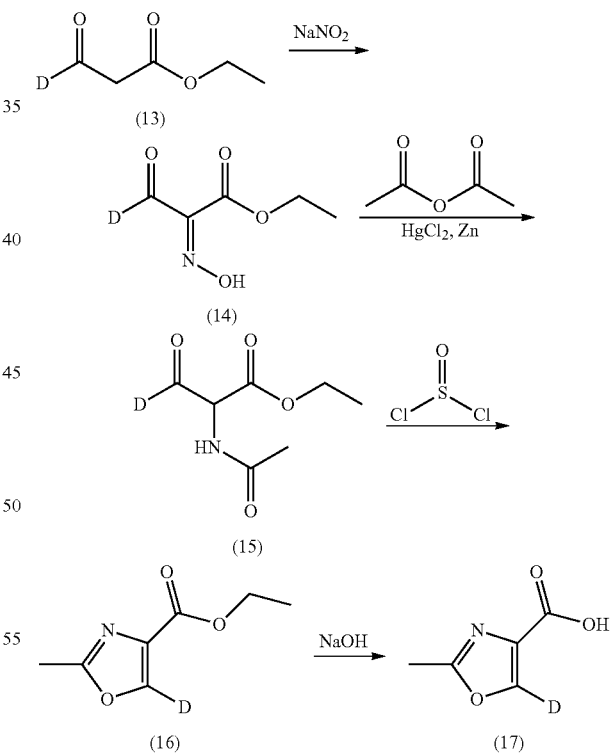

By reaction of a commercially available 3-oxo-propionic acid ester derivative (13) with an aqueous solution of sodium nitrite in presence of an acid such as glacial acetic acid the corresponding oxime derivative (14) can be obtained. The 2-acetamido-3-oxo-propionic acid ester derivative (15) can be synthesized from compounds of structure (14) using acetic anhydride in presence of an acid such as glacial acetic acid and catalytic amounts of metal chlorides such as mercury chloride and zinc powder. Cyclization to the corresponding oxazole-4 carboxylic acid ester derivative (16) can be achieved under dehydrating conditions such as thionyl chloride in chloroform. Saponification of the ester function using methods known in the art such as treatment with a base such as NaOH in solvent mixtures such as ethanol/water provides the corresponding oxazole-4 carboxylic acid derivative (17).

Carboxylic acid derivatives A-COOH wherein A represents a phenyl-2-yl derivative are commercially available or can be synthesised according to scheme 5.

Scheme 6: Synthesis of carboxylic acids $R^1$—COOH which represent an imidazo[2,1-b]thiazole-2-carboxylic acid derivative Pathway A

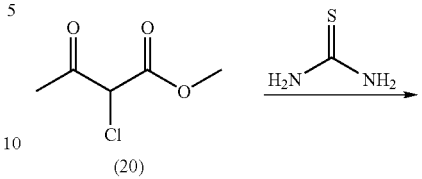

Scheme 5: Synthesis of carboxylic acids A—COOH wherein A represents a phenyl-2-yl derivative

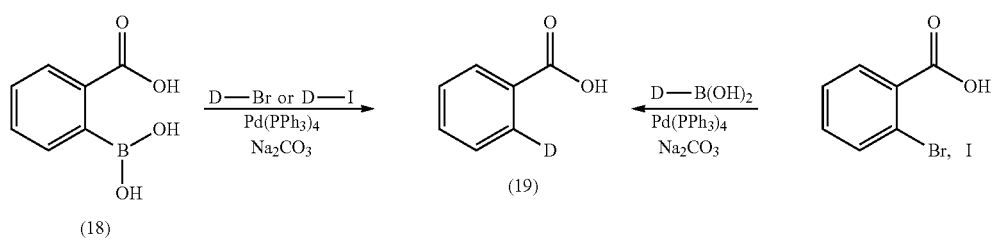

Reaction of commercially available (2-carboxyphenyl)-boronic acid derivatives (18) or esters thereof with commercially available aryl-bromides or aryl-iodides of formula D-Br or D-I in presence of a catalyst such as Pd(PPh$_3$)$_4$ and a base such as Na$_2$CO$_3$ under heating in a solvent such as toluene, dioxane, THF provides, after saponification, if needed, of the ester using well known methods, the corresponding phenyl-2-carboxylic acid derivatives (19). Alternatively, reaction of commercially available 2-bromo-, or 2-iodo-benzoic acid, or esters thereof, with commercially available boronic acid derivatives of formula D-B(OH)$_2$ using the conditions described before provides the corresponding phenyl-2-carboxylic acid derivatives (19).

Synthesis of Carboxylic Acids $R^1$—COOH

Carboxylic acids of formula $R^1$—COOH are commercially available or well known in the art (Lit. e.g. WO2001/96302; T. Eicher, S. Hauptmann "The chemistry of Heterocycles: Structure, Reactions, Syntheses, and Applications", 2nd Edition 2003, Wiley, ISBN 978-3-527-30720-3).

Carboxylic acid derivatives $R^1$—COOH which represent an imidazo[2,1-b]thiazole-2-carboxylic acid derivative are commercially available or can be synthesised according to scheme 6.

Pathway A: By reaction of 2-chloro-3-oxo-butyric acid methyl ester (20) with thiourea the amino-thiazole (21) can be obtained. Transformation to ester (22) can be accomplished with bromoacetaldehyde which can be generated in-situ from bromoacetaldehyde diethylacetal under acidic conditions. After saponification with bases such as sodium hydroxide the desired acid (23) can be obtained.

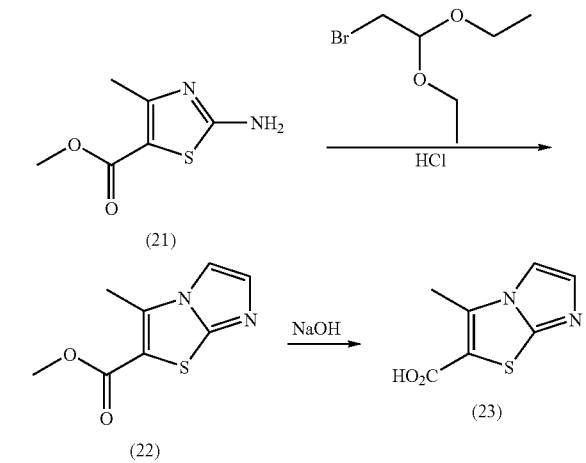

Pathway B

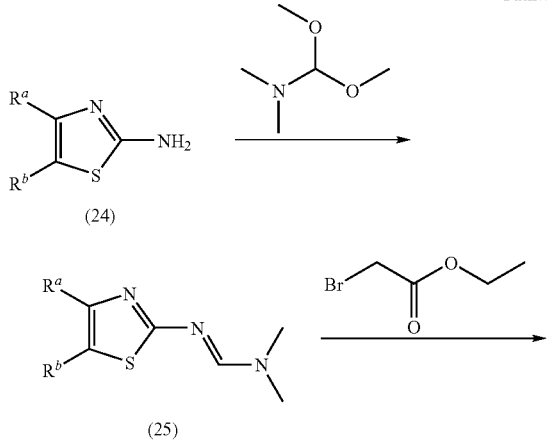

-continued

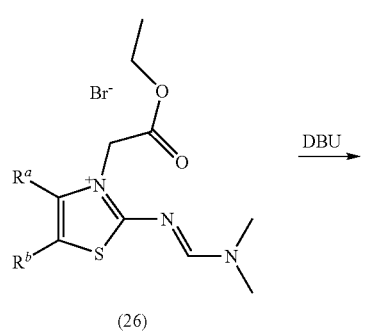

Pathway B: By heating a compound of structure (24) with N,N-dimethylformamide dimethylacetal in a solvent such as toluene formamidine derivatives (25) can be obtained. They can be alkylated with ethyl bromoacetate yielding the respective thiazolium bromide (26) which can be cyclised with strong bases such as DBU to the ester (27). Saponification of the ester function using methods known in the art such as treatment with a base such as NaOH in a solvent such as ethanol/water provides the corresponding imidazo[2,1-b]thiazole-2-carboxylic acid derivatives (28).

Carboxylic acid derivatives $R^1$—COOH which represent a pyrrolo[2,1-b]thiazole-7-carboxylic acid derivative can be synthesised according to scheme 7

By reaction of 2-methylsulfanylthiazole (29) with trimethylsilylmethyl trifluoromethanesulfonate followed by cyclisation of the resulting thiazolinium salt by reaction with ethyl propiolate in the presence of caesium fluoride, the pyrrolo[2,1-b]thiazole (30) can be obtained. Saponification of the ester function using methods known in the art such as treatment with a base such as NaOH in a solvent such as EtOH/water provides the corresponding pyrrolo[2,1-b]thiazole-7-carboxylic acid derivative (31) (Berry C. R. et al., *Organic Letters*, 2007, 9, 21, 4099-4102).

Scheme 7: Synthesis of carboxylic acids $R^1$—COOH which represent a pyrrolo [2,1-b]thiazole-7-carboxylic acid derivative

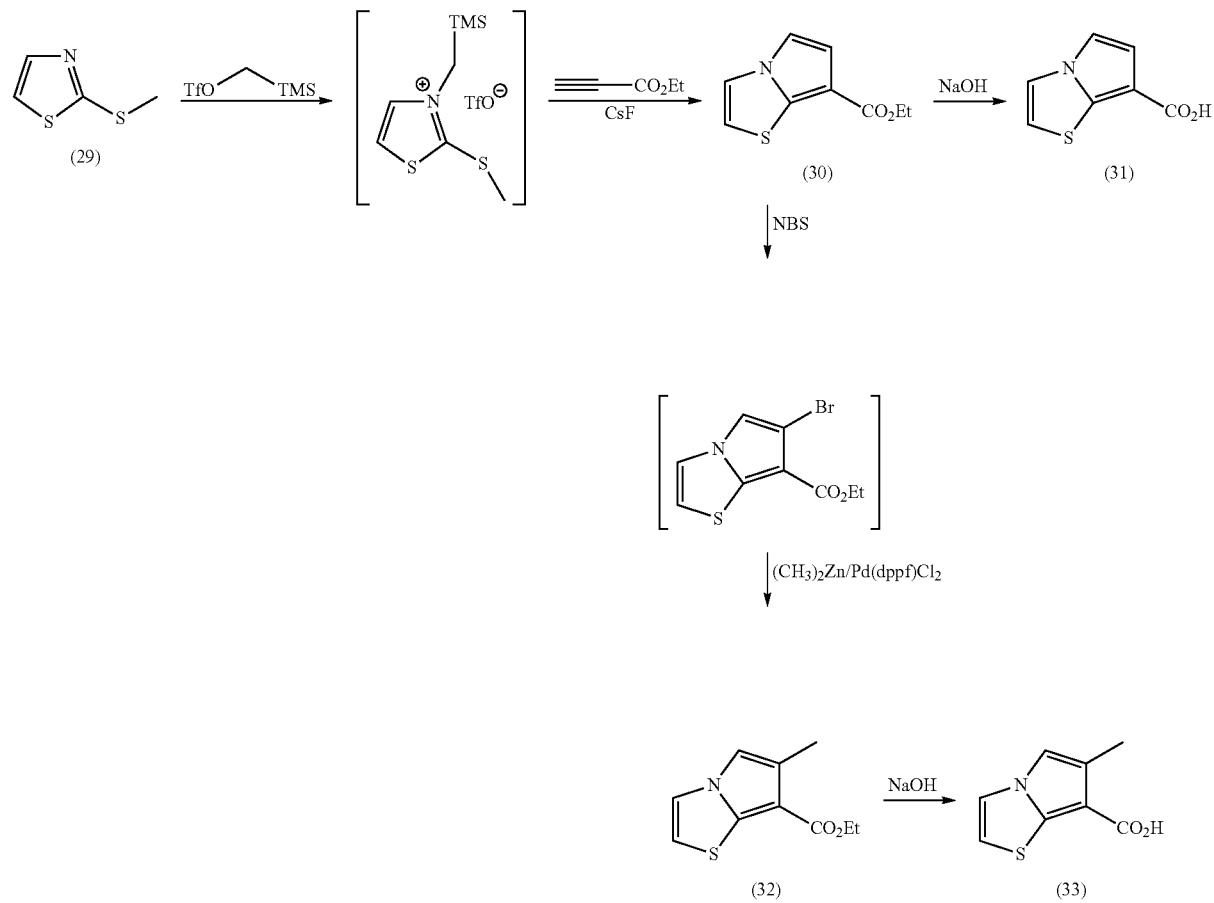

Bromination of (30) by reaction with NBS followed by methylation of the resulting crude ethyl 6-bromo-pyrrolo[2,1-b]thiazole-7-carboxylate by reaction with dimethylzinc in the presence of a palladium catalyst such as Pd(dppf)Cl₂ gave the ester (32). Saponification of the ester function using methods known in the art such as treatment with a base such as NaOH in a solvent such as EtOH/water provides the corresponding 6-methyl-pyrrolo[2,1-b]thiazole-7-carboxylic acid derivative (33).

Carboxylic acid derivatives R¹—COOH which represent a 3,4-dihydro-2H-benzo[1,4]oxazinyl- or 3-oxo-3,4-dihydro-2H-benzo[1,4]oxazinyl-carboxylic acid derivative can be synthesised according to the literature according to schemes 8 and 9.

Esterification of 3-hydroxy-anthranilic acid (34) with concentrated sulphuric acid in EtOH provides the corresponding ethyl ester (35). Cyclisation with acetyl chloride in presence of a base such as K₂CO₃ in a solvent such as DMF provides 3-oxo-3,4-dihydro-2H-benzo[1,4]oxazine derivatives (36). Compounds of structure (36) can optionally be alkylated with alkylating reagents such as methyl iodide in presence of a base such as K₂CO₃. Saponification with a base such as NaOH in a solvent such as EtOH/water leads to the corresponding acids (37) or (38). Reduction of compounds of structure (36) with NaBH₄ in the presence of BF₃-diethyl etherate leads to the corresponding 3,4-dihydro-2H-benzo[1,4]oxazine derivative which can optionally be alkylated and/or saponified as described before to provide the corresponding acids (40) or (41) (Kuroita T. et al, *Chemical Pharmaceutical Bulletin* 1996, 44, 4, 756-764).

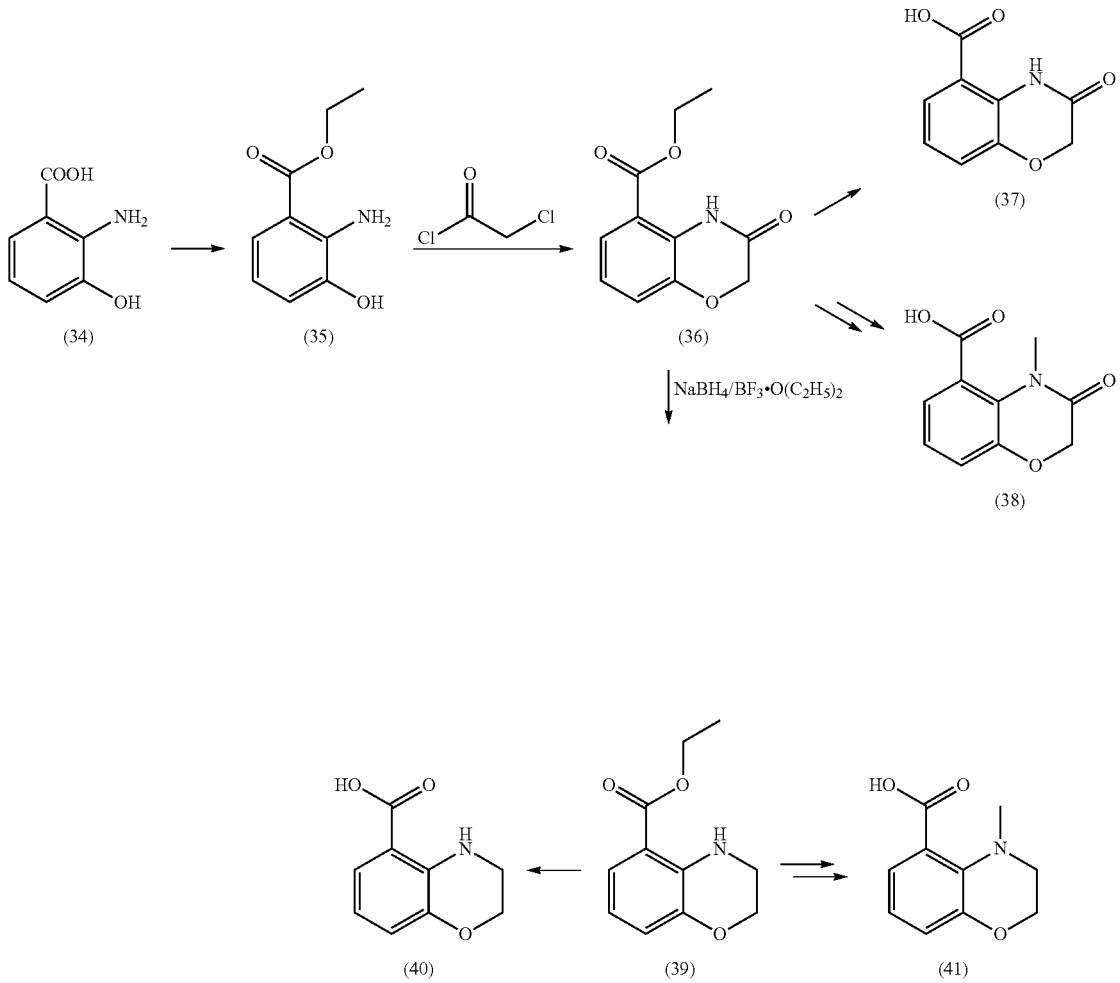

Scheme 8: Synthesis of carboxylic acids R¹—COOH which represent a 3,4-dihydro-2H-benzo[1,4]oxazinyl- or 3-oxo,4dihydro-2H-benzo[1,4]oxazinyl-carboxylic acid derivative Scheme 9: Synthesis of carboxylic acids $R^1$—COOH which represent a 3,4-dihydro-2H-benzo[1,4] oxazinyl-carboxylic acid derivative Scheme 10: Synthesis of carboxylic acids $R^1$—COOH which represent a benzooxazole-4-carboxylic acid derivative

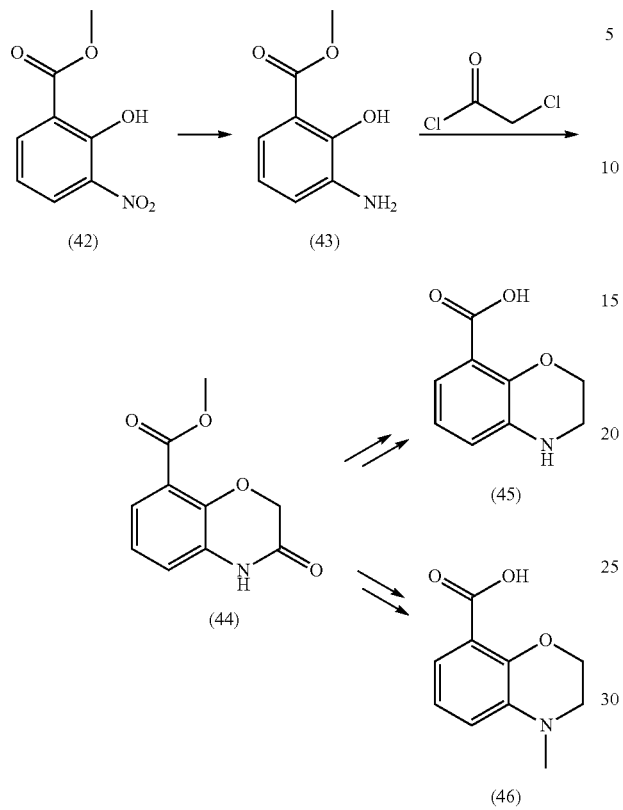

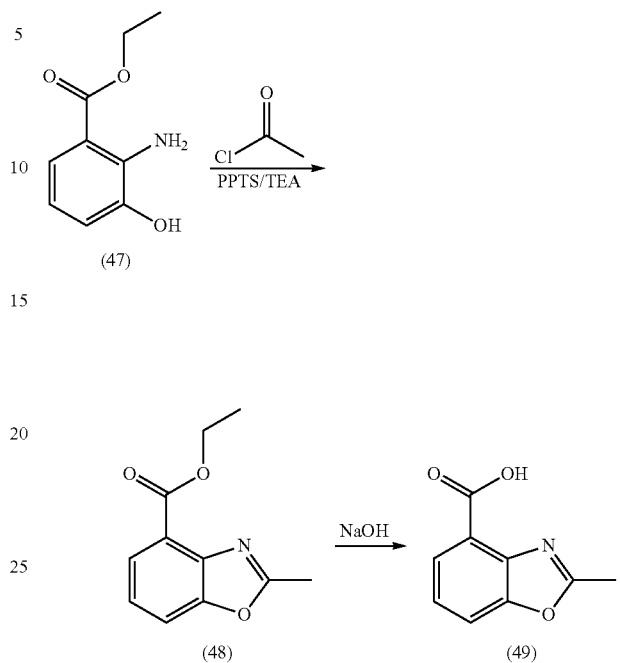

By cyclisation of ethyl 2-amino-3-hydroxybenzoate (47) with acetyl chloride in the presence of PPTS and TEA, the ester (48) can be obtained (Goldstein S. W. et al, *Journal of Heterocyclic Chemistry*, 1990, 27, 335-336). Saponification of the ester function using methods known in the art such as treatment with a base such as NaOH in a solvent such as EtOH/water provides the corresponding 2-methyl-benzooxazole-4-carboxylic acid derivative (49).

Hydrogenation of methyl 3-nitrosalicylate (42) in presence of a palladium catalyst provides the aniline derivative (43) which can be cyclized with chloroacetyl chloride as described before to the ester (44). Reduction of compounds of structure (44) with $NaBH_4$ in the presence of $BF_3$-diethyl etherate leads to the corresponding 3,4-dihydro-2H-benzo[1,4]oxazine derivative which can optionally be alkylated and/or saponified as described before to provide the corresponding acids (45) or (46) (Kuroita T. et al, *Chemical Pharmaceutical Bulletin* 1996, 44, 4, 756-764).

Carboxylic acid derivatives $R^1$—COOH which represent a benzooxazole-4-carboxylic acid derivative can be synthesised according to the literature according to schemes 10 and 11.

Scheme 11: Synthesis of carboxylic acids $R^1$—COOH which represent a bensooxazole-7-carboxylic acid derivative

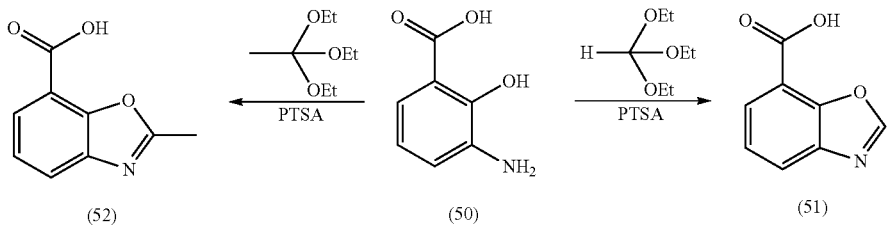

By cyclisation of 3-aminosalicylic acid (50) with triethyl orthoformate in the presence of PTSA, the benzooxazole-7-carboxylic acid (51) can be obtained (WO2006/069155). By cyclisation of 3-aminosalicylic acid (50) with triethyl orthoacetate in the presence of PTSA, the 2-methyl-benzooxazole-7-carboxylic acid (52) can be obtained (WO2006/069155)

Carboxylic acid derivatives $R^1$—COOH which represent a benzothiazole-7-carboxylic acid derivative can be synthesised according to the literature according to scheme 12.

Scheme 12: Synthesis of carboxylic acids R¹—COOH which represent a benzothiazole-7-carboxylic acid derivative

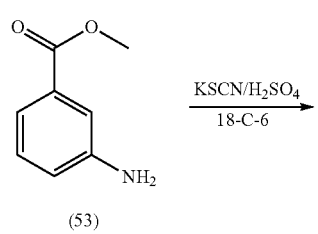

(53)

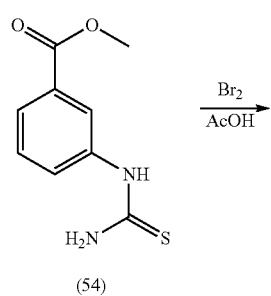

(54)

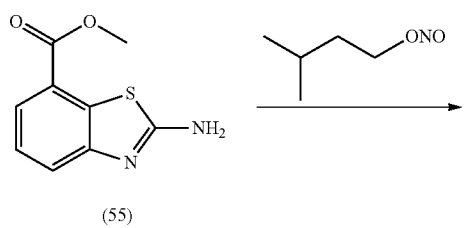

(55)

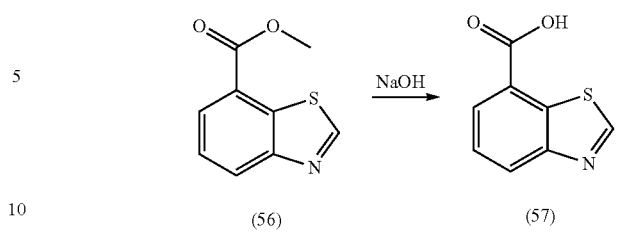

(56)    (57)

By reaction of methyl 3-aminobenzoate (53) with potassium thiocyanate in the presence of sulfuric acid and crown-ether 18-C-6, the thiourea (54) can be obtained. Cyclisation by reaction with bromine in acetic acid provides the 2-aminobenzothiazole derivative (55). Cleavage of the amino group by reaction with isoamyl nitrite furnishes the ester (56) (WO2005/092890). Saponification of the ester function using methods known in the art such as treatment with a base such as NaOH in a solvent such as MeOH/water provides the corresponding benzothiazole-7-carboxylic acid derivative (57).

Carboxylic acid derivatives R¹—COOH which represent a benzofuran-4-carboxylic acid derivative can be synthesised according to the literature according to schemes 13 and 14.

By reaction of methyl 3-hydroxybenzoate (58) with 3-chloro-2-butanone, the ester (59) can be obtained. Cyclisation with sulfuric acid provides the 2,3-dimethyl-benzofurane derivative (60) (Kawase Y. et al, *Bulletin of the Chemical Society of Japan,* 1967, 40, 5, 1224-1231). Saponification of the ester function using methods known in the art such as treatment with a base such as NaOH in a solvent such as MeOH/water provides the corresponding 2,3-dimethyl-benzofuran-4-carboxylic acid derivative (61). On the other hand, reaction of methyl 3-hydroxybenzoate (58) with crotyl bromide furnishes the ester (62) which after reaction in N,N-dimethylaniline provides the ester (63). Ozonolysis followed by reaction with PTSA gives the 3-methyl-benzofurane derivative (64) (Mohamadi F. et al, *Journal of Medicinal Chemistry,* 1994, 37, 232-239 and EP58906). Saponification of the ester function using methods known in the art such as treatment with a base such as NaOH in a solvent such as MeOH/water provides the corresponding 3-methylbenzofuran-4-carboxylic acid derivative (65).

Scheme 13: Synthesis of carboxylic acids R¹—COOH which represent a 2,3-dimethyl-benzofuran-4-carboxylic acid derivative

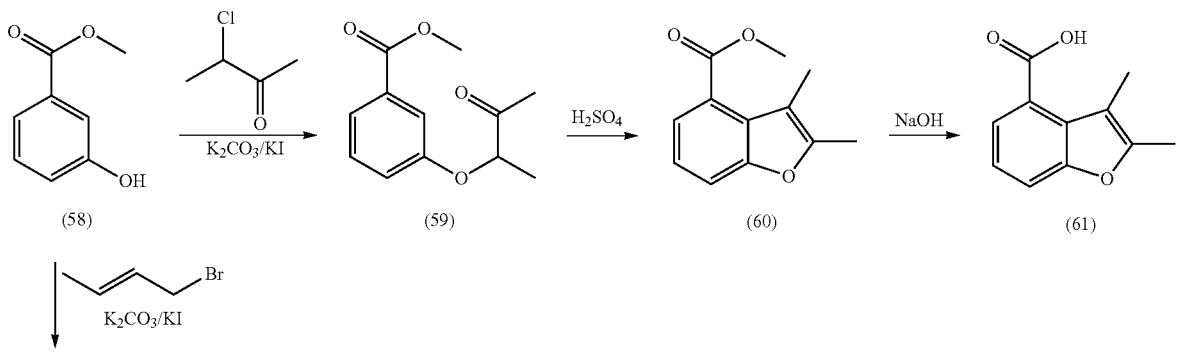

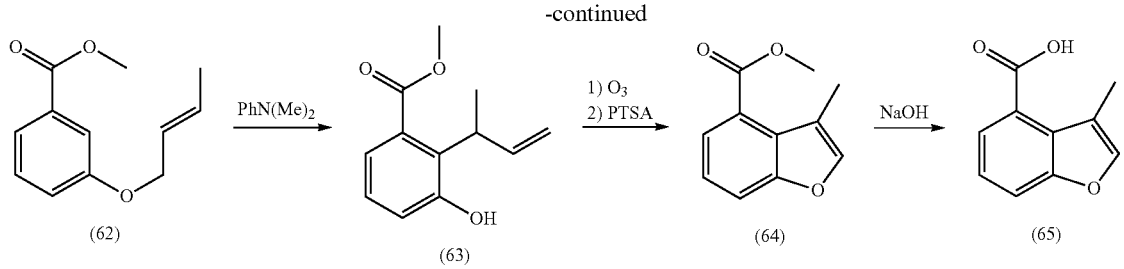

By cyclisation of 2-allyl-3-hydroxybenzaldehyde (66) with a palladium catalyst such as bis(acetonitrile)dichloropalladium in the presence of 1,4-benzoquinone and lithium chloride, the 2-methyl-benzofurane carbaldehyde (67) can be obtained (Danheiser R. L. et al, *Organic Letters,* 2005, 7, 18, 3905-3908). Oxidation of the aldehyde function with sodium chlorite in the presence of a scavenger such as 2-methyl-2-butene furnishes the corresponding 2-methylbenzofuran-4-carboxylic acid (68).

Scheme 14: Synthesis of carboxylic acids $R^1$—COOH which represent a 2-methylbenzofuran-4-carboxylic acid derivative

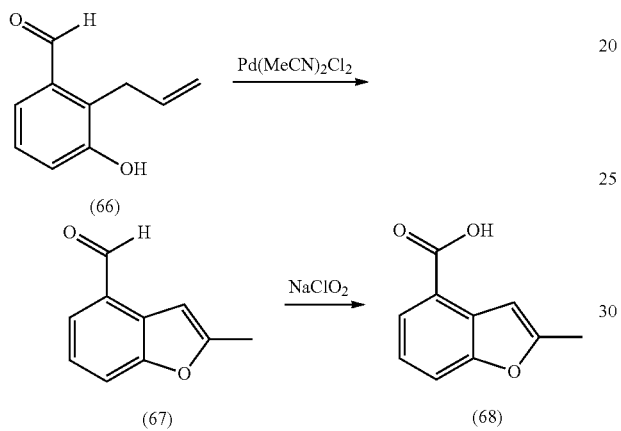

Carboxylic acid derivatives $R^1$—COOH which represent a benzofuran-4-carboxylic acid derivative and R represent Cl, F or $CF_3$ can be synthesised according to the literature according to scheme 15.

Scheme 15: Synthesis of carboxylic acids $R^1$—COOH which represent a substituted-benzofuran-4-carboxylic acid derivative

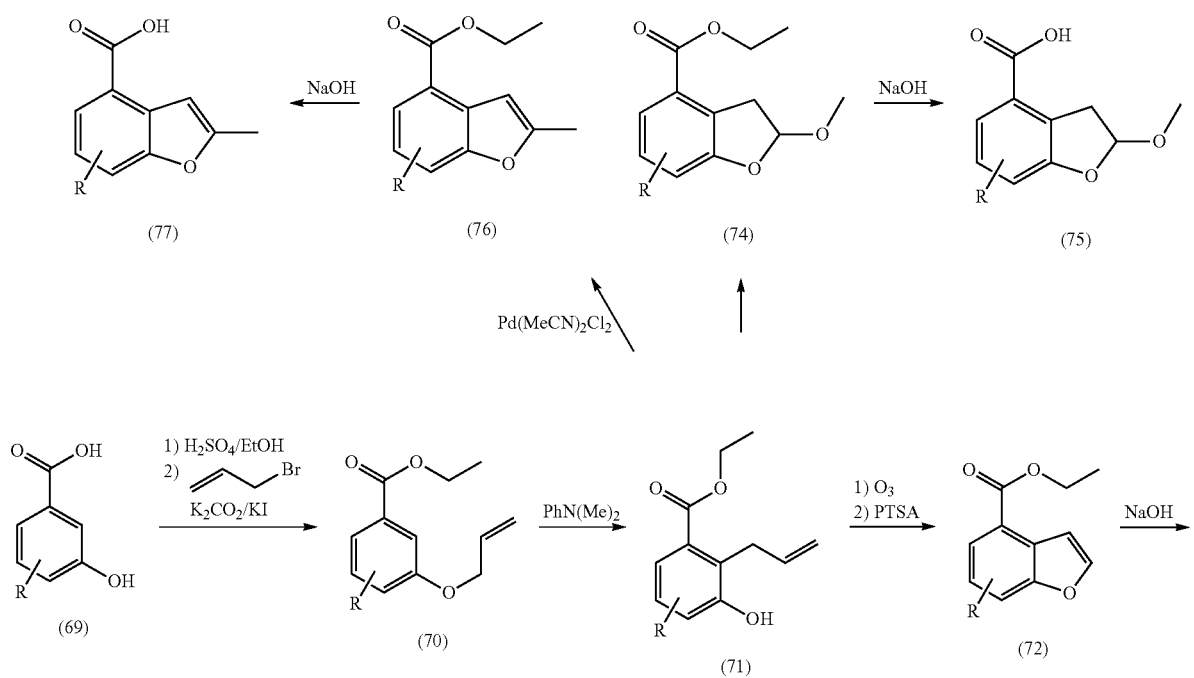

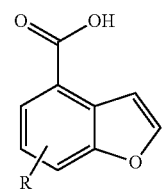

(73)

By esterification of phenol derivative (69) with EtOH in the presence of an acid such as sulfuric acid followed by alkylation by reaction with allyl bromide in the presence of a $K_2CO_3$ and KI, the alkyl-ether derivative (70) can be obtained. Claisen rearrangement by reaction with N,N-dimethylaniline furnishes the phenol derivative (71). Ozonolysis followed by reaction with PTSA provides the benzofurane derivative (72). On the other hand ozonolysis of (71) in the presence of MeOH furnishes the dihydro-benzofurane derivative (74). Saponification of the ester function of (72) and (74) using methods known in the art such as treatment with a base such as NaOH in a solvent such as EtOH/water provide the corresponding benzofuran-4-carboxylic acid derivatives (73) and (75). Furthermore, cyclisation of (71) with a palladium catalyst such as bis(acetonitrile)dichloropalladium in the presence of 1,4-benzoquinone and lithium chloride, the 2-methylbenzofurane derivative (76) can be obtained (Danheiser R. L. et al, *Organic Letters*, 2005, 7, 18, 3905-3908). Saponification of the ester function of (76) using methods known in the art such as treatment with a base such as NaOH in a solvent such as EtOH/water provide the corresponding 2-methyl-benzofuran-4-carboxylic acid derivatives (77).

Carboxylic acid derivatives $R^1$—COOH which represent a benzofuran-4-carboxylic acid derivative can be synthesised according to the literature according to scheme 16.

Scheme 16: Synthesis of carboxylic acids $R^1$—COOH which represent a 2-hydroxymethylbenzofuran-4-carboxylic acid derivative

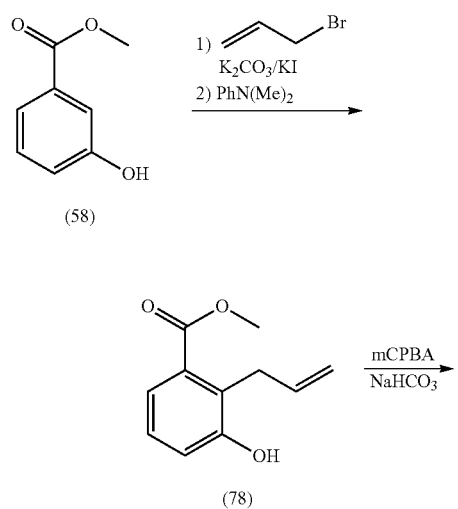

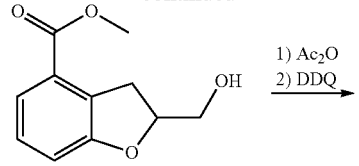

(79)

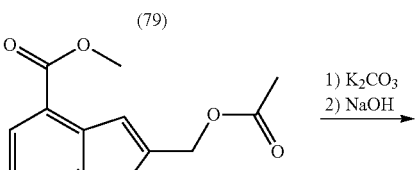

(80)

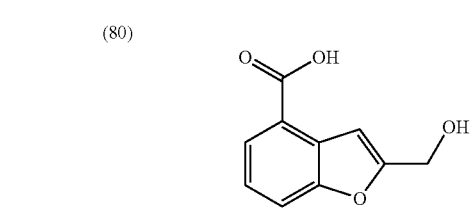

(81)

By alkylation of methyl 2-hydroxybenzoate (58) with allyl bromide in the presence of $K_2CO_3$ and KI followed by Claisen rearrangement by reaction with N,N-dimethylaniline the phenol derivative (78) can be obtained. Cyclisation by reaction with mCPBA in presence of a base such as $NaHCO_3$ furnishes the desired dihydro-benzofurane derivative (79). Acetylation by reaction with acetic anhydride followed by oxidation with DDQ provides the corresponding benzofurane derivative (80). Cleavage of the acetyl group by reaction with $K_2CO_3$ followed by saponification of the ester function using methods known in the art such as treatment with a base such as NaOH in a solvent such as MeOH/water provide the corresponding 2-hydroxymethylbenzofuran-4-carboxylic acid derivatives (81).

Carboxylic acid derivatives $R^1$—COOH which represent a 2-fluorobenzofuran-4-carboxylic acid derivative can be synthesised according to the literature according to scheme 17.

Specific electrophilic fluorination of benzofuran-4-carboxylic acid (82) (Eissenstat M. A. et al, *Journal of Medicinal Chemistry* 1995, 38, 16, 3094-3105) by reaction with tert-butyl lithium followed by reaction with NFSI (Torrado A. et al *Bioorganic Medicinal Chemistry* 2004, 12, 5277-5295 and Differling E. et al Synlett, 1991, 1, 187-189) provides the desired 2-fluorobenzofuran-4-carboxylic acid (83).

Scheme 17: Synthesis of carboxylic acids R¹—COOH which represent a 2-fluorobenzofuran-4-carboxylic acid derivative

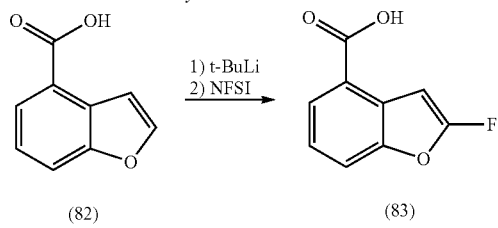

Compounds which contain a 2-trifluoromethylbenzofurane moiety can be synthesised according to the literature according to scheme 18.

the Boc-protecting group with TFA, acylation with A-CO₂H using classical amide coupling methodology (TBTU/DIPEA) and finally removal of the trifluoroacetyl-protecting group by reaction with sat. K₂CO₃. Trifluoromethylation of (87) with methyl (fluorosulfonyl)difluoroacetate in the presence of copper (I) iodide in a mixture of HMPA/DMF (Chen Q. et al *Journal of Chemical Society: Chemical Communications* 1989, 11, 705-706 and Chen Q. et al *Journal of Fluorine Chemistry.* 1991, 55, 3, 291-298) provides the 2-trifluoromethyl-benzofurane thiazolidine derivatives (88).

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk- Scheme 18: Synthesis of compounds containing a 2-trifluoromethyl-benzofurane moiety

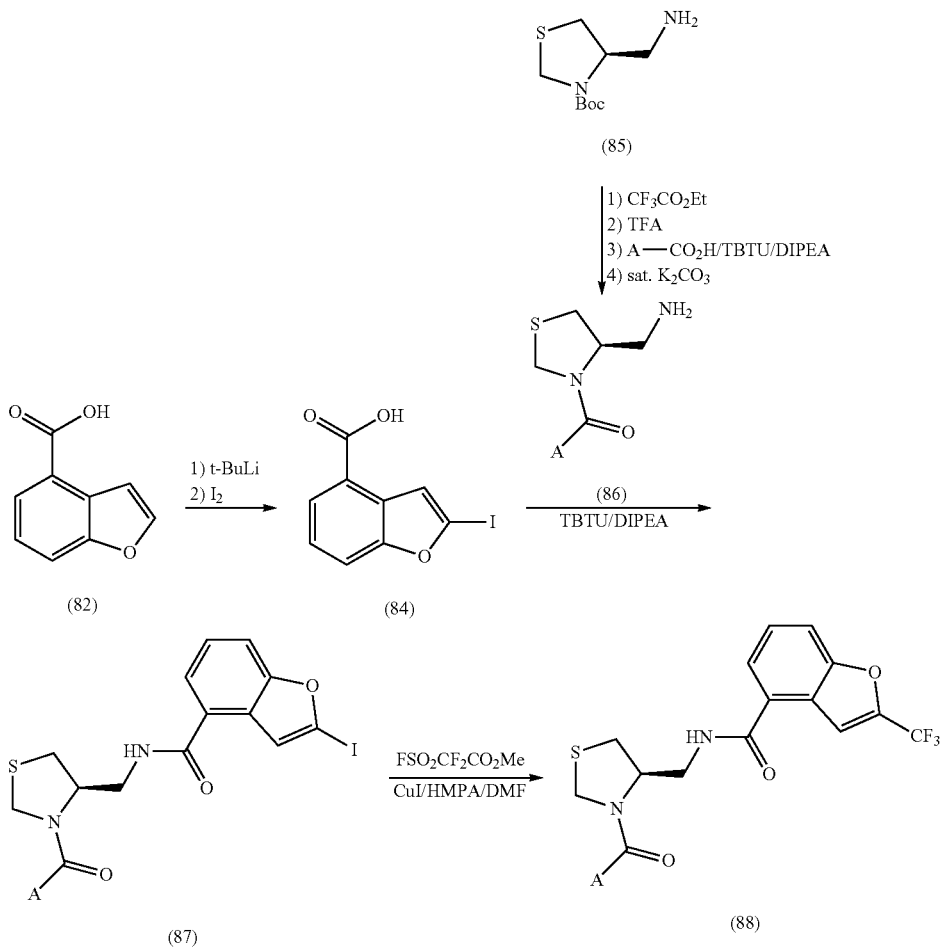

Specific electrophilic iodination of benzofuran-4-carboxylic acid (82) by reaction with tert-butyl lithium followed by reaction with iodine provides the desired 2-iodo-benzofuran-4-carboxylic acid (84). Amide coupling using classical methodology (i.e. TBTU/DIPEA) with n-acyl-thiazolidine (86) derivative furnishes bis-N-acyl-thiazolidine intermediate (87). The N-acyl-thiazolidine derivatives (86) can be prepared by trifluoroacetylation of commercially available (R)-4-Aminomethyl-thiazolidine-3-carboxylic acid tert-butyl ester (85) with ethyl trifluoroacetate followed by removal of O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (ethanol, in presence or absence of an amine such as TEA, diethylamine) and eluent B (hexane), at a flow rate of 0.8 to 150 mL/min.

EXPERIMENTAL SECTION

Abbreviations (as used herein and in the description above):

aq. aqueous
Boc tert-Butoxycarbonyl
BSA Bovine serum albumine
CHO Chinese hamster ovary
conc. Concentrated
d Day(s)
DBU 1,8-Diazabicyclo[5.4.0]undec-7-ene
DCM Dichloromethane
DDQ 2,3-Dichloro-5,6-dicyano-1,4-benzoquinone
DIPEA Diisopropylethylamine
DMAP 4-Dimethylaminopyridine
DMF N,N-Dimethylformamide
dppf diphenylphosphinoferrocene
EDC 1-Ethyl-3-(3-dimethylaminopropyl)-carbodiimide
eq Equivalent(s)
ES Electron spray
Et Ethyl
ether diethylether
EtOAc Ethyl acetate
FCS Foatal calf serum
FLIPR Fluorescent imaging plate reader
h Hour(s)
HATU (O-(7-azabenzotriazol-1-yl)-1,1,3,3-tetramethyl-uronium hexafluorphoshate
HBSS Hank's balanced salt solution
HCl Hydrochloric acid
HEPES 4-(2-hydroxyethyl)-piperazine-1-ethanesulfonic acid
HMPA Hexamethylphosphoramide
HOAt 1-hydroxy-7-azabenzotriazole
HOBt 1-hydroxy-benzotriazole
HPLC High performance liquid chromatography
KOtBu Potassium tert. butoxide
LC Liquid chromatography
M Molar(ity)
Me Methyl
MeCN Acetonitrile
mCPBA meta-chloroperoxybenzoic acid
MeOH Methanol
min Minute(s)
MS Mass spectroscopy
NBS N-bromosuccinimide
NFSI N-Fluorobenzenesulfonimide
prep. Preparative
PPTS Pyridinium 4-toluenesulfonate
PTSA p-Toluenesulfonic acid
RT Room temperature
sat Saturated
$t_R$ Retention time
TBTU O-(Benzotriazol-1-yl)-N,N,N',N'-tetramethyluronium tetrafluoroborate
TEA Triethylamine
TFA trifluoroacetic acid
THF Tetrahydrofuran I-Chemistry All temperatures are stated in ° C. Compounds are characterized by $^1$H-NMR (300 MHz: Varian Oxford or 400 MHz: Bruker Avance); chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, using two conditions:
basic: eluent A: MeCN, eluent B: conc. NH$_3$ in water (1.0 mL/L), 5% to 95% CH$_3$CN;
acidic: eluent A: MeCN, eluent B: TFA in water (0.4 mL/L), 5% to 95% CH$_3$CN), $t_R$ is given in min; by TLC (TLC-plates from Merck, Silica gel 60 F$_{254}$); or by melting point. Compounds are purified by column chromatography on silica gel or by preparative HPLC (column: X-terra RP18, 50×19 mm, 5 µm, gradient: 10-95% MeCN in water containing 0.5% of formic acid).

The following examples illustrate the preparation of pharmacologically active compounds of the invention but do not at all limit the scope thereof.

Preparation of Precursors and Intermediates

A.1 Synthesis of thiazole-carboxylic acid Derivatives
A.1.1 Synthesis of 3-chloro-2-oxo-propionic ester Derivatives (General Procedure)

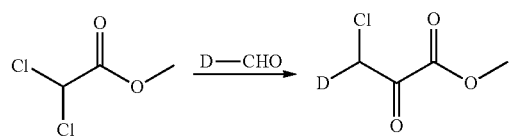

A solution of the respective benzaldehyde derivative D-CHO (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred over night and concentrated in vacuo. DCM and ice-cold water are added, the layers are separated and the aqueous layer is extracted twice with DCM. The combined organic layers are washed with ice-cold water and brine, dried over MgSO$_4$ and concentrated in vacuo to give the corresponding 3-chloro-2-oxo-propionic acid methyl ester derivative which is used without further purification.

3-Chloro-2-oxo-3-phenyl-propionic acid methyl ester
  prepared by reaction of benzaldehyde with methyl dichloroacetate.
3-Chloro-2-oxo-3-m-tolyl-propionic acid methyl ester
  prepared by reaction of 3-methyl-benzaldehyde with methyl dichloroacetate.
3-Chloro-2-oxo-3-p-tolyl-propionic acid methyl ester
  prepared by reaction of 4-methyl-benzaldehyde with methyl dichloroacetate.
3-Chloro-3-(3-fluoro-phenyl)-2-oxo-propionic acid methyl ester
  prepared by reaction of 3-fluoro-benzaldehyde with methyl dichloroacetate.
3-Chloro-3-(3,4-dichloro-phenyl)-2-oxo-propionic acid methyl ester
  prepared by reaction of 3,4-dichloro-benzaldehyde with methyl dichloroacetate.

3-Chloro-3-(3,4-difluoro-phenyl)-2-oxo-propionic acid methyl ester
prepared by reaction of 3,4-difluoro-benzaldehyde with methyl dichloroacetate.
3-Chloro-3-(3,4-dimethyl-phenyl)-2-oxo-propionic acid methyl ester
prepared by reaction of 3,4-dimethyl-benzaldehyde with methyl dichloroacetate.
3-Chloro-3-(2-fluoro-phenyl)-2-oxo-propionic acid methyl ester
prepared by reaction of 2-fluoro-benzaldehyde with methyl dichloroacetate.
3-Chloro-3-(4-methoxy-phenyl)-2-oxo-propionic acid methyl ester
prepared by reaction of 4-methoxy-benzaldehyde with methyl dichloroacetate.
3-Chloro-3-(3-methoxy-phenyl)-2-oxo-propionic acid methyl ester
prepared by reaction of 3-methoxy-benzaldehyde with methyl dichloroacetate.
3-Chloro-3-(2-methoxy-phenyl)-2-oxo-propionic acid methyl ester
prepared by reaction of 2-methoxy-benzaldehyde with methyl dichloroacetate.
3-Chloro-3-(4-fluoro-phenyl)-2-oxo-propionic acid methyl ester
prepared by reaction of 4-fluoro-benzaldehyde with methyl dichloroacetate.
3-Chloro-2-oxo-3-(3-trifluoromethyl-phenyl)-propionic acid methyl ester
prepared by reaction of 3-trifluoromethyl-benzaldehyde with methyl dichloro-acetate.
3-Chloro-2-oxo-3-(4-trifluoromethyl-phenyl)-propionic acid methyl ester
prepared by reaction of 4-trifluoromethyl-benzaldehyde with methyl dichloroacetate.

A.1.2 Synthesis of 2-methyl-thiazole-4-carboxylic acid methyl ester Derivatives (General Procedure)

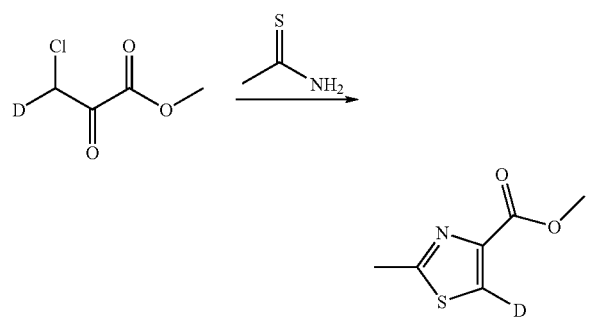

A solution of thioacetamide (132 mmol, 1.0 eq) in MeCN (250 mL) is added to a mixture of the respective 3-chloro-2-oxo-propionic acid methyl ester derivative (132 mmol, 1.0 eq) and molecular sieves (4 Å, 12 g) in MeCN (60 mL). After stirring for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the corresponding 2-methyl-thiazole-4-carboxylic acid methyl ester derivatives.

2-Methyl-5-m-tolyl-thiazole-4-carboxylic acid methyl ester
prepared by reaction of 3-chloro-2-oxo-3-m-tolyl-propionic acid methyl ester with thioacetamide. LC-MS: $t_R$=0.94 min; $[m+H]^+$=248.0.
2-Methyl-5-p-tolyl-thiazole-4-carboxylic acid methyl ester
prepared by reaction of 3-chloro-2-oxo-3-p-tolyl-propionic acid methyl ester with thioacetamide. LC-MS: $t_R$=0.93 min; $[m+H]^+$=248.02.
5-(3-Fluoro-phenyl)-2-methyl-thiazole-4-carboxylic acid methyl ester
prepared by reaction of 3-chloro-3-(3-fluoro-phenyl)-2-oxo-propionic acid methyl ester with thioacetamide. LC-MS: $t_R$=0.91 min; $[m+H]^+$=252.1.
5-(4-Fluoro-phenyl)-2-methyl-thiazole-4-carboxylic acid methyl ester
prepared by reaction of 3-chloro-3-(4-fluoro-phenyl)-2-oxo-propionic acid methyl ester with thioacetamide. $^1$H-NMR (CDCl$_3$): δ=2.75 (5, 3H); 3.84 (5, 3H); 7.10 (m, 2H); 7.47 (m, 2H).
5-(2-Fluoro-phenyl)-2-methyl-thiazole-4-carboxylic acid methyl ester
prepared by reaction of 3-chloro-3-(2-fluoro-phenyl)-2-oxo-propionic acid methyl ester with thioacetamide. LC-MS: $t_R$=0.90 min; $[m+H]^+$=251.99.
2-Methyl-5-(3-trifluoromethyl-phenyl)-thiazole-4-carboxylic acid methyl ester
prepared by reaction of 3-chloro-3-(3-trifluoromethyl-phenyl)-2-oxo-propionic acid methyl ester with thioacetamide. LC-MS: $t_R$=0.99 min; $[m+H]^+$=301.99.
2-Methyl-5-(4-trifluoromethyl-phenyl)-thiazole-4-carboxylic acid methyl ester
prepared by reaction of 3-chloro-3-(4-trifluoromethyl-phenyl)-2-oxo-propionic acid methyl ester with thioacetamide. LC-MS: $t_R$=0.99 min; $[m+H]^+$=301.99
2-Methyl-5-(3,4-dimethyl-phenyl)-thiazole-4-carboxylic acid methyl ester
prepared by reaction of 3-chloro-3-(3,4-dimethyl-phenyl)-2-oxo-propionic acid methyl ester with thioacetamide. LC-MS: $t_R$=0.96 min; $[M+H]^+$=262.34.
2-Methyl-5-(3,4-dichloro-phenyl)-thiazole-4-carboxylic acid methyl ester
prepared by reaction of 3-chloro-3-(3,4-dichloro-phenyl)-2-oxo-propionic acid methyl ester with thioacetamide. LC-MS: $t_R$=0.99 min; $[m+H]^+$=302.22.
2-Methyl-5-(3,4-difluoro-phenyl)-thiazole-4-carboxylic acid methyl ester
prepared by reaction of 3-chloro-3-(3,4-difluoro-phenyl)-2-oxo-propionic acid methyl ester with thioacetamide. LC-MS: $t_R$=0.92 min; $[m+H]^+$=270.29.
5-(4-Methoxy-phenyl)-2-methyl-thiazole-4-carboxylic acid methyl ester
prepared by reaction of 3-chloro-3-(4-methoxy-phenyl)-2-oxo-propionic acid methyl ester with thioacetamide. LC-MS: $t_R$=0.90 min; $[m+H]^+$=263.93.
5-(3-Methoxy-phenyl)-2-methyl-thiazole-4-carboxylic acid methyl ester
prepared by reaction of 3-chloro-3-(3-methoxy-phenyl)-2-oxo-propionic acid methyl ester with thioacetamide. LC-MS: $t_R$=0.90 min; $[m+H]^+$=263.87.

5-(2-Methoxy-phenyl)-2-methyl-thiazole-4-carboxylic acid methyl ester
prepared by reaction of 3-chloro-3-(2-methoxy-phenyl)-2-oxo-propionic acid methyl ester with thioacetamide. LC-MS: $t_R$=0.88 min; [m+H]$^+$=264.05.

5-Phenyl-2-methyl-thiazole-4-carboxylic acid methyl ester
prepared by reaction of 3-chloro-3-phenyl-2-oxo-propionic acid methyl ester with thioacetamide. LC-MS: $t_R$=0.88 min; [m+H]$^+$=234.23.

A.1.3 Synthesis of thiazole-4-carboxylic acid Derivatives (General Procedure)

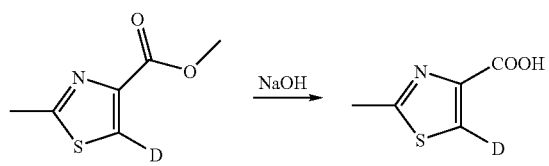

A solution of the respective thiazole-4-carboxylic acid methyl ester (96.2 mmol) in a mixture of THF (150 mL) and MeOH (50 mL) is treated with 1M aq. NaOH (192 mL). After stirring for 3 h a white suspension is formed and the organic volatiles are removed in vacuo. The remaining mixture is diluted with water (100 mL), cooled in an ice-bath and acidified (pH=3-4) by addition of 1M aq. HCl. The suspension is filtered and the residue is washed with cold water. After drying the corresponding 2-methyl-thiazole-4-carboxylic acid derivative is obtained.

2-Methyl-5-m-tolyl-thiazole-4-carboxylic acid
prepared by saponification of 2-methyl-5-m-tolyl-thiazole-4-carboxylic acid methyl ester. LC-MS: $t_R$=0.83 min; [m+H]$^+$=233.99.

2-Methyl-5-p-tolyl-thiazole-4-carboxylic acid
prepared by saponification of 2-methyl-5-p-tolyl-thiazole-4-carboxylic acid methyl ester. LC-MS: $t_R$=0.83 min; [m+H]$^+$=234.0.

5-(3-Fluoro-phenyl)-2-methyl-thiazole-4-carboxylic acid
prepared by saponification of 5-(3-fluoro-phenyl)-2-methyl-thiazole-4-carboxylic acid methyl ester. LC-MS: $t_R$=0.82 min; [m+H]$^+$=238.1.

5-(4-Fluoro-phenyl)-2-methyl-thiazole-4-carboxylic acid
prepared by saponification of 5-(4-fluoro-phenyl)-2-methyl-thiazole-4-carboxylic acid methyl ester. $^1$H-NMR (DMSO-d$_6$): δ=2.67 (s, 3H); 7.27 (m, 2H); 7.53 (m, 2H); 12.89 (br.s, 1H).

2-Methyl-5-(3-trifluoromethyl-phenyl)-thiazole-4-carboxylic acid
prepared by saponification of 2-methyl-5-(3-trifluoromethyl-phenyl)-thiazole-4-carboxylic acid methyl ester. LC-MS: $t_R$=0.88 min; [m+H]$^+$=287.99.

2-Methyl-5-(4-trifluoromethyl-phenyl)-thiazole-4-carboxylic acid
prepared by saponification of 2-methyl-5-(4-trifluoromethyl-phenyl)-thiazole-4-carboxylic acid methyl ester. LC-MS: $t_R$=0.90 min; [m+H]$^+$=287.99.

2-Methyl-5-(3,4-dimethyl-phenyl)-thiazole-4-carboxylic acid
prepared by saponification of 2-methyl-5-(3,4-dimethyl-phenyl)-thiazole-4-carboxylic acid methyl ester. LC-MS: $t_R$=0.97 min; [m+H]$^+$=382.38.

2-Methyl-5-(3,4-dichloro-phenyl)-thiazole-4-carboxylic acid
prepared by saponification of 2-methyl-5-(3,4-dichloro-phenyl)-thiazole-4-carboxylic acid methyl ester. LC-MS: $t_R$=0.88 min; [M+H]$^+$=288.22.

2-Methyl-5-(3,4-difluoro-phenyl)-thiazole-4-carboxylic acid
prepared by saponification of 2-methyl-5-(3,4-difluoro-phenyl)-thiazole-4-carboxylic acid methyl ester. LC-MS: $t_R$=0.82 min; [m+H]$^+$=256.25.

2-Methyl-5-(2-methoxy-phenyl)-thiazole-4-carboxylic acid
prepared by saponification of 2-methyl-5-(2-methoxy-phenyl)-thiazole-4-carboxylic acid methyl ester. LC-MS: $t_R$=0.78 min; [m+H]$^+$=249.98.

2-Methyl-5-(3-methoxy-phenyl)-thiazole-4-carboxylic acid
prepared by saponification of 2-methyl-5-(3-methoxy-phenyl)-thiazole-4-carboxylic acid methyl ester. LC-MS: $t_R$=0.80 min; [M+H]$^+$=250.04.

2-Methyl-5-(4-methoxy-phenyl)-thiazole-4-carboxylic acid
prepared by saponification of 2-methyl-5-(4-methoxy-phenyl)-thiazole-4-carboxylic acid methyl ester. LC-MS: $t_R$=0.80 min; [m+H]$^+$=250.04.

2-Methyl-5-phenyl-thiazole-4-carboxylic acid
prepared by saponification of 2-methyl-5-phenyl-thiazole-4-carboxylic acid methyl ester. LC-MS: $t_R$=0.78 min; [M+H]$^+$=220.01.

A.1.4 Synthesis of 2-methyl-4-p-tolyl-thiazole-5-carboxylic acid

A mixture of 4-methylbenzoyl acetate (5.52 mmol), sulfuryl chloride (5.52 mmol) in chloroform (3.3 ml) was held at reflux overnight. After cooling down to room temperature the organic phase was washed with water, dried over MgSO$_4$ and concentrated under reduced pressure. The crude product was dissolved in THF (12.0 ml) and thioacetamide (6.75 mmol) and solid NaHCO$_3$ (6.07 mmol) were added. The mixture was heated to reflux for 6 h and then it was filtered. The solvent was removed and the crude product purified by column chromatography using heptane/ethyl acetate as eluent system to provide 2-methyl-4-p-tolyl-thiazole-5-carboxylic acid methyl ester (2.67 mmol).

2-Methyl-4-p-tolyl-thiazole-5-carboxylic acid methyl ester (2.67 mmol) and solid KOH (5.35 mmol) were dissolved in ethanol (1.04 mL) and water (0.26 mL) and heated under reflux for 3 hours. After cooling, the solvent was evaporated under reduced pressure and ice water was added to the residue, followed by washing with hexane. The aqueous layer was acidified with 1N aq. HCl and the crystals thus precipitated were collected by filtration, washed with water and then dried to provide 2-methyl-4-p-tolyl-thiazole-5-carboxylic acid. LC-MS: $t_R$=0.83 min; [m+H]$^+$=234.02.

A.2 Synthesis of 2-methyl-oxazole-4-carboxylic acid Derivatives

A.2.1 Synthesis of 2-acetylamino-3-oxo-propionic acid methyl ester Derivatives (General Procedure)

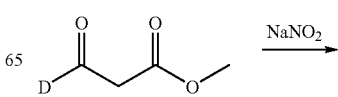

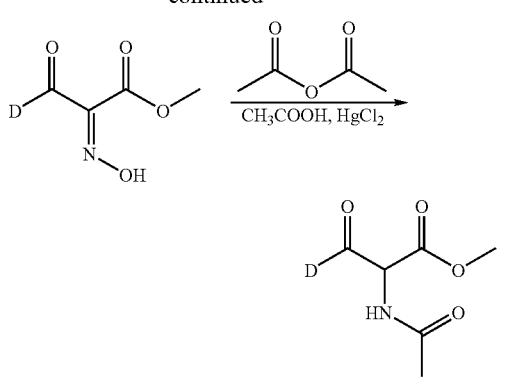

A solution of the respective 3-oxo-propionic acid methyl ester derivative (4.8 mmol, 1.0 eq.) in glacial acetic acid (1.9 mL) was cooled to 10° C. and at this temperature was added a solution of NaNO$_2$ (5.6 mmol, 1.16 eq.) in water (0.68 mL). After the addition was complete (15 min), the solution was allowed to warm to room temperature and stirred for 2 h. Then the solution was poured into water (10 mL) and after a few minutes crystals begun to appear. This suspension was cooled in an ice-bath and crystals were collected by filtration. The cake was washed several times with cold water and the water was removed by the azeotrope of toluene-water in vacuo to give 2-hydroxyimino-3-oxo-propionic acid methyl ester derivatives which were dissolved in a mixture of acetic anhydride (1.375 mL) and glacial acetic acid (1.8 mL). To this solution was added sodium acetate (0.296 mmol, 0.06 eq.) and HgCl$_2$ (0.01 mmol, 0.002 eq.). The mixture was refluxed for 1 h, then cooled to room temperature and filtered. The solid was rinsed with ether, the organic filtrate was recovered, washed 3 times with water and one time with 1M aq. K$_2$CO$_3$. The organic layer was dried over MgSO$_4$, filtered and concentrated. The crude products were purified by flash chromatography to afford the corresponding 2-acetylamino-3-oxo-propionic acid methyl ester derivatives.

2-Acetylamino-3-oxo-3-(3-trifluoromethyl-phenyl)-propionic acid methyl ester prepared according to general procedure A.2.1 from 3-oxo-(3-trifluoromethyl-phenyl)-propionic acid methyl ester.

2-Acetylamino-3-oxo-3-m-tolyl-propionic acid methyl ester prepared according to general procedure A.2.1 from 3-oxo-3-m-tolyl-propionic acid methyl ester.

2-Acetylamino-3-oxo-3-p-tolyl-propionic acid methyl ester prepared according to general procedure A.2.1 from 3-oxo-3-p-tolyl-propionic acid methyl ester.

2-Acetylamino-3-(4-fluoro-phenyl)-3-oxo-propionic acid methyl ester prepared according to general procedure A.2.1 from 3-oxo-3-(4-fluoro-phenyl)-propionic acid methyl ester.

2-Acetylamino-3-(4-methoxy-phenyl)-3-oxo-propionic acid methyl ester prepared according to general procedure A.2.1 from 3-oxo-3-(4-methoxy-phenyl)-propionic acid methyl ester.

A.2.2 Synthesis of 2-methyl-oxazole-4-carboxylic acid Derivatives (General Procedure)

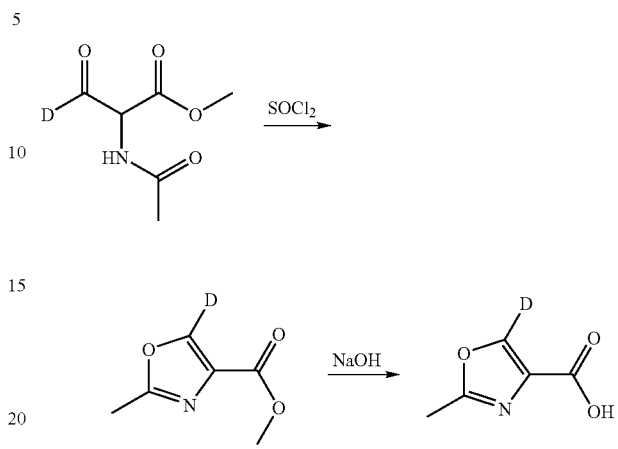

A solution of the respective 2-acetylamino-3-oxo-propionic acid methyl ester derivative (0.63 mmol, 1.0 eq.) in chloroform (0.4 mL) was cooled to 0° C. in an ice/NaCl bath. SOCl$_2$ (0.88 mmol, 1.4 eq.) was added to the stirred solution and the temperature was maintained at 0° C. for 30 minutes. Then the solution was stirred and refluxed for one hour. Another 0.25 eq. of SOCl$_2$ was added and the reaction mixture was refluxed for another hour.

The excess SOCl$_2$ was quenched with 1M aq. K$_2$CO$_3$. The aqueous layer was extracted twice with ether. The combined organic phases were washed once with water and dried over MgSO$_4$, filtered and concentrated yielding the corresponding 2-methyl-oxazole-4-carboxylic acid methyl ester derivative. The respective 2-methyl-oxazole-4-carboxylic acid methyl ester derivative was dissolved in a mixture of ethanol (0.7 ml) and 2N aq. NaOH (0.7 mL, 2.5 eq.). The mixture was stirred at RT for 2 hours.

The reaction mixture was washed once with ether and this organic layer was discarded. The aqueous layer was then acidified with conc. HCl and extracted twice with ether. Both organic layers were combined, dried over MgSO$_4$ and concentrated in vacuo to afford the corresponding 2-methyl-oxazole-4-carboxylic acid derivatives.

2-Methyl-5-m-tolyl-oxazole-4-carboxylic acid prepared according to general procedure A.2.2 from 2-acetylamino-3-oxo-3-m-tolyl-propionic acid methyl ester LC-MS: $t_R$=0.51 min; [M–H]$^+$=216.33.

2-Methyl-5-(3-trifluoromethyl-phenyl)-oxazole-4-carboxylic acid prepared according to general procedure A.2.2 from 2-acetylamino-3-oxo-3-(3-trifluoromethyl-phenyl)-propionic acid methyl ester. LC-MS: $t_R$=0.55 min; [M–H]$^+$=270.24.

2-Methyl-5-p-tolyl-oxazole-4-carboxylic acid prepared according to general procedure A.2.2 from 2-acetylamino-3-oxo-3-p-tolyl-propionic acid methyl ester. LC-MS: $t_R$=0.55 min; [M–H]$^+$=216.34.

5-(4-Fluoro-phenyl)-2-methyl-oxazole-4-carboxylic acid prepared according to general procedure A.2.2 from 2-acetylamino-3-(4-fluoro-phenyl)-3-oxo-propionic acid methyl ester. LC-MS: $t_R$=0.49 min; [M–H]$^+$=220.30.

5-(4-Methoxy-phenyl)-2-methyl-oxazole-4-carboxylic acid prepared according to general procedure A.2.2 from 2-acetylamino-3-(4-methoxy-phenyl)-3-oxo-propionic acid methyl ester. LC-MS: $t_R$=0.77 min; [M+H]$^+$=234.31.

5-(3-Methoxy-phenyl)-2-methyl-oxazole-4-carboxylic acid prepared according to general procedure A.2.2 from 2-acetylamino-3-(3-methoxy-phenyl)-3-oxo-propionic acid methyl ester. LC-MS: $t_R$=0.49 min; [M+H]$^+$=232.30.

A.3 Biphenyl-2-carboxylic acid derivatives

The following biphenyl-2-carboxylic acid derivatives are commercially available:
Biphenyl-2-carboxylic acid;
4'-Methyl-biphenyl-2-carboxylic acid;
3'-Methyl-biphenyl-2-carboxylic acid;
3',4'-Dimethyl-biphenyl-2-carboxylic acid;
4'-Methoxy-biphenyl-2-carboxylic acid;
3'-Methoxy-biphenyl-2-carboxylic acid;
4'-Fluoro-biphenyl-2-carboxylic acid.

A.4 Synthesis of 4-{[acyl-amino]-methyl}-thiazolidine derivatives

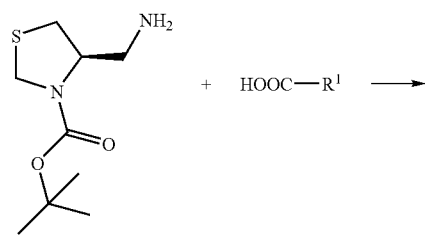

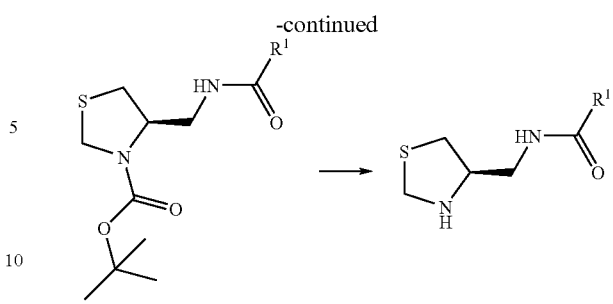

A.4.1 Synthesis of 4-{[acyl-amino]-methyl}-thiazolidine-3-carboxylic acid tert-butyl ester Derivatives (General Procedure)

To a solution of the respective carboxylic acid R$^1$COOH, wherein R$^1$ is as defined for formula (I), (4.6 mmol, 1.0 eq.), 4-aminomethyl-thiazolidine-3-carboxylic acid tert-butyl ester (4.6 mmol, 1.0 eq.) and DMAP (2.3 mmol, 1.0 eq.) in DCM (25 mL) was added under stirring solid EDC (4.7 mmol, 1.02 eq.). Stirring continued over night. Then sat. aq. NaHCO$_3$ solution (6 mL) was added to the reaction mixture and stirring continued for 30 min. The organic phase was separated, the solvent was stripped off yielding the crude corresponding 4-{[acyl-amino]-methyl}-thiazolidine-3-carboxylic acid tert-butyl ester derivative.

The following intermediates were synthesized according to general procedure A.4.1 from commercially available (R)-4-aminomethyl-thiazolidine-3-carboxylic acid tert-butyl ester and the respective carboxylic acid R$^1$COOH, which is commercially available or synthesized according to methods described above:

| Intermediate | Name | [M + H]$^+$ | $t_R$ |
|---|---|---|---|
| I1 | (R)-4-{[(Benzofuran-4-carbonyl)-amino]-methyl}-thiazolidine-3-carboxylic acid tert-butyl ester | 363.06 | 0.96 |
| I2 | (R)-4-{[(6-Methyl-imidazo[2,1-b]thiazole-5-carbonyl)-amino]-methyl}-thiazolidine-3-carboxylic acid tert-butyl ester | 383.03 | 0.81 |
| I3 | (R)-4-{[(1-Methyl-1H-indazole-3-carbonyl)-amino]-methyl}-thiazolidine-3-carboxylic acid tert-butyl ester | 377.07 | 0.97 |
| I4 | (R)-4-{[(2,3-Dihydro-benzo[1,4]dioxine-5-carbonyl)-amino]-methyl}-thiazolidine-3-carboxylic acid tert-butyl ester | 381.06 | 0.94 |
| I5 | (R)-4-[(3-Bromo-benzoylamino)-methyl]-thiazolidine-3-carboxylic acid tert-butyl ester | 402.81 | 1.00 |
| I6 | (R)-4-{[(1-Methyl-1H-indole-2-carbonyl)-amino]-methyl}-thiazolidine-3-carboxylic acid tert-butyl ester | 376.08 | 1.02 |
| I7 | (R)-4-{[(4-Bromo-thiophene-2-carbonyl)-amino]-methyl}-thiazolidine-3-carboxylic acid tert-butyl ester | 408.93 | 0.99 |
| I8 | (R)-4-{[(6-Bromo-pyridine-2-carbonyl)-amino]-methyl}-thiazolidine-3-carboxylic acid tert-butyl ester | 403.97 | 0.98 |

A.4.2 Synthesis of 4-{[acyl-amino]-methyl}-thiazolidine Derivatives

The respective 4-{[acyl-amino]-methyl}-thiazolidine-3-carboxylic acid tert-butyl ester derivative (0.15 mmol, 1.0 eq.) was dissolved in a mixture of dry MeOH (0.33 mL) and 4 M HCl in dioxane (0.75 mL, 20 eq.). After shaking for 2 h the solvent was evaporated and the residue treated with dry MeOH (1 mL) followed by evaporation and drying under vacuo for 14 h to provide the corresponding 4-{[acyl-amino]-methyl}-thiazolidine derivative hydrochloride.

PREPARATION OF EXAMPLES

General Procedure 1

The corresponding thiazole-carboxylic acid derivative (Intermediate according to method A.1), 2-methyl-oxazole-4-carboxylic acid derivative (Intermediate according to method A.2), or biphenyl-2-carboxylic acid derivative (Intermediate according to method A.3), respectively, (0.15 mmol, 1.0 eq.) was dissolved in a mixture of dry DMF (1.0 mL) and DIPEA (0.58 mmol, 3.9 eq.) under stirring. Solid HATU (0.15 mmol, 1.0 eq.) was added and stirring was allowed for 10 min. This solution was added to the respective crude 4-{[acyl-amino]-methyl}-thiazolidine derivative hydrochloride (Intermediate according to method A.4) and the mixture was stirred over night. The DMF was evaporated under vacuum and the crude product purified by prep. HPLC to provide the final compound.

The following Examples given in table 1 were synthesized according to the general procedure 1 given above:

TABLE 1

| Example | Name | $[M + H]^+$ | $t_R$ |
|---|---|---|---|
| 1 | Benzofuran-4-carboxylic acid {(R)-3-[5-(4-fluoro-phenyl)-2-methyl-thiazole-4-carbonyl]-thiazolidin-4-ylmethyl}-amide | 482.03 | 0.97 |
| 2 | 6-Methyl-imidazo[2,1-b]thiazole-5-carboxylic acid {(R)-3-[5-(4-fluoro-phenyl)-2-methyl-thiazole-4-carbonyl]-thiazolidin-4-ylmethyl}-amide | 502.09 | 0.83 |
| 3 | 2,3-Dihydro-benzo[1,4]dioxine-5-carboxylic acid {(R)-3-[5-(4-fluoro-phenyl)-2-methyl-thiazole-4-carbonyl]-thiazolidin-4-ylmethyl}-amide | 500.12 | 0.96 |
| 4 | 1-Methyl-1H-indazole-3-carboxylic acid {(R)-3-[5-(4-fluoro-phenyl)-2-methyl-thiazole-4-carbonyl]-thiazolidin-4-ylmethyl}-amide | 496.12 | 0.97 |
| 5 | Benzofuran-4-carboxylic acid [(R)-3-(2-methyl-5-phenyl-thiazole-4-carbonyl)-thiazolidin-4-ylmethyl]-amide | 464.13 | 0.96 |
| 6 | Benzofuran-4-carboxylic acid [(R)-3-(2-methyl-5-p-tolyl-thiazole-4-carbonyl)-thiazolidin-4-ylmethyl]-amide | 478.13 | 0.99 |
| 7 | Benzofuran-4-carboxylic acid {(R)-3-[2-methyl-5-(4-trifluoromethyl-phenyl)-thiazole-4-carbonyl]-thiazolidin-4-ylmethyl}-amide | 532.06 | 1.02 |
| 8 | Benzofuran-4-carboxylic acid {(R)-3-[5-(3-fluoro-phenyl)-2-methyl-thiazole-4-carbonyl]-thiazolidin-4-ylmethyl}-amide | 482.11 | 0.98 |
| 9 | Benzofuran-4-carboxylic acid {(R)-3-[5-(3,4-dimethyl-phenyl)-2-methyl-thiazole-4-carbonyl]-thiazolidin-4-ylmethyl}-amide | 492.14 | 1.02 |
| 10 | Benzofuran-4-carboxylic acid {(R)-3-[5-(2-fluoro-phenyl)-2-methyl-thiazole-4-carbonyl]-thiazolidin-4-ylmethyl}-amide | 482.10 | 0.98 |
| 11 | Benzofuran-4-carboxylic acid {(R)-3-[5-(3-methoxy-phenyl)-2-methyl-thiazole-4-carbonyl]-thiazolidin-4-ylmethyl}-amide | 494.12 | 0.97 |
| 12 | Benzofuran-4-carboxylic acid {(R)-3-[2-methyl-5-(3-trifluoromethyl-phenyl)-thiazole-4-carbonyl]-thiazolidin-4-ylmethyl}-amide | 532.07 | 1.03 |
| 13 | Benzofuran-4-carboxylic acid {(R)-3-[5-(3,4-difluoro-phenyl)-2-methyl-thiazole-4-carbonyl]-thiazolidin-4-ylmethyl}-amide | 500.11 | 0.99 |
| 14 | Benzofuran-4-carboxylic acid {(R)-3-[5-(2-methoxy-phenyl)-2-methyl-thiazole-4-carbonyl]-thiazolidin-4-ylmethyl}-amide | 494.11 | 0.97 |
| 15 | Benzofuran-4-carboxylic acid {(R)-3-[2-methyl-5-(3-trifluoromethyl-phenyl)-oxazole-4-carbonyl]-thiazolidin-4-ylmethyl}-amide | 516.10 | 1.01 |
| 16 | Benzofuran-4-carboxylic acid [(R)-3-(2-methyl-5-p-tolyl-oxazole-4-carbonyl)-thiazolidin-4-ylmethyl]-amide | 462.15 | 0.98 |
| 17 | Benzofuran-4-carboxylic acid {(R)-3-[5-(4-fluoro-phenyl)-2-methyl-oxazole-4-carbonyl]-thiazolidin-4-ylmethyl}-amide | 466.14 | 0.96 |
| 18 | Benzofuran-4-carboxylic acid [(R)-3-(2-methyl-4-p-tolyl-thiazole-5-carbonyl)-thiazolidin-4-ylmethyl]-amide | 478.14 | 0.98 |
| 19 | Benzofuran-4-carboxylic acid [(R)-3-(2-methyl-5-m-tolyl-oxazole-4-carbonyl)-thiazolidin-4-ylmethyl]-amide | 462.15 | 0.98 |

TABLE 1-continued

| Example | Name | [M + H]+ | t$_R$ |
|---|---|---|---|
| 20 | Benzofuran-4-carboxylic acid {(R)-3-[5-(3,4-dichloro-phenyl)-2-methyl-thiazole-4-carbonyl]-thiazolidin-4-ylmethyl}-amide | 532.02 | 1.04 |
| 21 | Benzofuran-4-carboxylic acid {(R)-3-[5-(4-methoxy-phenyl)-2-methyl-oxazole-4-carbonyl]-thiazolidin-4-ylmethyl}-amide | 478.15 | 0.96 |
| 22 | Benzofuran-4-carboxylic acid [(R)-3-(4'-methyl-biphenyl-2-carbonyl)-thiazolidin-4-ylmethyl]-amide | 457.17 | 1.03 |
| 23 | Benzofuran-4-carboxylic acid [(R)-3-(3',4'-dimethyl-biphenyl-2-carbonyl)-thiazolidin-4-ylmethyl]-amide | 471.18 | 1.05 |
| 24 | Benzofuran-4-carboxylic acid [(R)-3-(3'-methyl-biphenyl-2-carbonyl)-thiazolidin-4-ylmethyl]-amide | 457.17 | 1.03 |
| 25 | Benzofuran-4-carboxylic acid [(R)-3-(3'-methoxy-biphenyl-2-carbonyl)-thiazolidin-4-ylmethyl]-amide | 473.17 | 1.00 |
| 26 | Benzofuran-4-carboxylic acid [(R)-3-(4'-fluoro-biphenyl-2-carbonyl)-thiazolidin-4-ylmethyl]-amide | 461.14 | 1.01 |
| 27 | Benzofuran-4-carboxylic acid [(R)-3-(4'-methoxy-biphenyl-2-carbonyl)-thiazolidin-4-ylmethyl]-amide | 473.15 | 1.00 |
| 28 | 6-Methyl-imidazo[2,1-b]thiazole-5-carboxylic acid [(R)-3-(2-methyl-5-phenyl-thiazole-4-carbonyl)-thiazolidin-4-ylmethyl]-amide | 484.10 | 0.81 |
| 29 | 6-Methyl-imidazo[2,1-b]thiazole-5-carboxylic acid [(R)-3-(2-methyl-5-p-tolyl-thiazole-4-carbonyl)-thiazolidin-4-ylmethyl]-amide | 498.10 | 0.85 |
| 30 | 6-Methyl-imidazo[2,1-b]thiazole-5-carboxylic acid {(R)-3-[2-methyl-5-(4-trifluoromethyl-phenyl)-thiazole-4-carbonyl]-thiazolidin-4-ylmethyl}-amide | 552.06 | 0.91 |
| 31 | 6-Methyl-imidazo[2,1-b]thiazole-5-carboxylic acid {(R)-3-[5-(3-fluoro-phenyl)-2-methyl-thiazole-4-carbonyl]-thiazolidin-4-ylmethyl}-amide | 502.03 | 0.83 |
| 32 | 6-Methyl-imidazo[2,1-b]thiazole-5-carboxylic acid {(R)-3-[5-(3,4-dimethyl-phenyl)-2-methyl-thiazole-4-carbonyl]-thiazolidin-4-ylmethyl}-amide | 512.10 | 0.88 |
| 33 | 6-Methyl-imidazo[2,1-b]thiazole-5-carboxylic acid {(R)-3-[5-(2-fluoro-phenyl)-2-methyl-thiazole-4-carbonyl]-thiazolidin-4-ylmethyl}-amide | 502.03 | 0.83 |
| 34 | 6-Methyl-imidazo[2,1-b]thiazole-5-carboxylic acid {(R)-3-[5-(3-methoxy-phenyl)-2-methyl-thiazole-4-carbonyl]-thiazolidin-4-ylmethyl}-amide | 514.08 | 0.83 |
| 35 | 6-Methyl-imidazo[2,1-b]thiazole-5-carboxylic acid {(R)-3-[2-methyl-5-(3-trifluoromethyl-phenyl)-thiazole-4-carbonyl]-thiazolidin-4-ylmethyl}-amide | 552.06 | 0.90 |
| 36 | 6-Methyl-imidazo[2,1-b]thiazole-5-carboxylic acid {(R)-3-[5-(3,4-difluoro-phenyl)-2-methyl-thiazole-4-carbonyl]-thiazolidin-4-ylmethyl}-amide | 520.05 | 0.86 |
| 37 | 6-Methyl-imidazo[2,1-b]thiazole-5-carboxylic acid {(R)-3-[5-(2-methoxy-phenyl)-2-methyl-thiazole-4-carbonyl]-thiazolidin-4-ylmethyl}-amide | 514.10 | 0.83 |
| 38 | 6-Methyl-imidazo[2,1-b]thiazole-5-carboxylic acid {(R)-3-[2-methyl-5-(3-trifluoromethyl-phenyl)-oxazole-4-carbonyl]-thiazolidin-4-ylmethyl}-amide | 536.08 | 0.89 |
| 39 | 6-Methyl-imidazo[2,1-b]thiazole-5-carboxylic acid [(R)-3-(2-methyl-5-p-tolyl-oxazole-4-carbonyl)-thiazolidin-4-ylmethyl]-amide | 482.14 | 0.80 |
| 40 | 6-Methyl-imidazo[2,1-b]thiazole-5-carboxylic acid {(R)-3-[5-(4-fluoro-phenyl)-2-methyl-oxazole-4-carbonyl]-thiazolidin-4-ylmethyl}-amide | 486.11 | 0.80 |
| 41 | 6-Methyl-imidazo[2,1-b]thiazole-5-carboxylic acid [(R)-3-(2-methyl-4-p-tolyl-thiazole-5-carbonyl)-thiazolidin-4-ylmethyl]-amide | 498.13 | 0.83 |
| 42 | 6-Methyl-imidazo[2,1-b]thiazole-5-carboxylic acid [(R)-3-(2-methyl-5-m-tolyl-oxazole-4-carbonyl)-thiazolidin-4-ylmethyl]-amide | 482.14 | 0.81 |
| 43 | 6-Methyl-imidazo[2,1-b]thiazole-5-carboxylic acid {(R)-3-[5-(3,4-dichloro-phenyl)-2-methyl-thiazole-4-carbonyl]-thiazolidin-4-ylmethyl}-amide | 551.99 | 0.91 |
| 44 | 6-Methyl-imidazo[2,1-b]thiazole-5-carboxylic acid {(R)-3-[5-(4-methoxy-phenyl)-2-methyl-oxazole-4-carbonyl]-thiazolidin-4-ylmethyl}-amide | 498.11 | 0.78 |
| 45 | 6-Methyl-imidazo[2,1-b]thiazole-5-carboxylic acid [(R)-3-(4'-methyl-biphenyl-2-carbonyl)-thiazolidin-4-ylmethyl]-amide | 477.13 | 0.90 |
| 46 | 6-Methyl-imidazo[2,1-b]thiazole-5-carboxylic acid [(R)-3-(3',4'-dimethyl-biphenyl-2-carbonyl)-thiazolidin-4-ylmethyl]-amide | 491.16 | 0.93 |
| 47 | 6-Methyl-imidazo[2,1-b]thiazole-5-carboxylic acid [(R)-3-(3'-methyl-biphenyl-2-carbonyl)-thiazolidin-4-ylmethyl]-amide | 477.15 | 0.90 |

TABLE 1-continued

| Example | Name | [M + H]+ | $t_R$ |
|---|---|---|---|
| 48 | 6-Methyl-imidazo[2,1-b]thiazole-5-carboxylic acid [(R)-3-(3'-methoxy-biphenyl-2-carbonyl)-thiazolidin-4-ylmethyl]-amide | 493.13 | 0.87 |
| 49 | 6-Methyl-imidazo[2,1-b]thiazole-5-carboxylic acid [(R)-3-(4'-fluoro-biphenyl-2-carbonyl)-thiazolidin-4-ylmethyl]-amide | 481.12 | 0.88 |
| 50 | 6-Methyl-imidazo[2,1-b]thiazole-5-carboxylic acid [(R)-3-(4'-methoxy-biphenyl-2-carbonyl)-thiazolidin-4-ylmethyl]-amide | 493.13 | 0.87 |
| 51 | 1-Methyl-1H-indazole-3-carboxylic acid [(R)-3-(2-methyl-5-phenyl-thiazole-4-carbonyl)-thiazolidin-4-ylmethyl]-amide | 478.15 | 0.96 |
| 52 | 1-Methyl-1H-indazole-3-carboxylic acid [(R)-3-(2-methyl-5-p-tolyl-thiazole-4-carbonyl)-thiazolidin-4-ylmethyl]-amide | 492.15 | 0.99 |
| 53 | 1-Methyl-1H-indazole-3-carboxylic acid {(R)-3-[2-methyl-5-(4-trifluoromethyl-phenyl)-thiazole-4-carbonyl]-thiazolidin-4-ylmethyl}-amide | 546.11 | 1.02 |
| 54 | 1-Methyl-1H-indazole-3-carboxylic acid {(R)-3-[5-(3-fluoro-phenyl)-2-methyl-thiazole-4-carbonyl]-thiazolidin-4-ylmethyl}-amide | 496.11 | 0.97 |
| 55 | 1-Methyl-1H-indazole-3-carboxylic acid {(R)-3-[5-(3,4-dimethyl-phenyl)-2-methyl-thiazole-4-carbonyl]-thiazolidin-4-ylmethyl}-amide | 506.15 | 1.02 |
| 56 | 1-Methyl-1H-indazole-3-carboxylic acid {(R)-3-[5-(2-fluoro-phenyl)-2-methyl-thiazole-4-carbonyl]-thiazolidin-4-ylmethyl}-amide | 496.12 | 0.98 |
| 57 | 1-Methyl-1H-indazole-3-carboxylic acid {(R)-3-[5-(3-methoxy-phenyl)-2-methyl-thiazole-4-carbonyl]-thiazolidin-4-ylmethyl}-amide | 508.14 | 0.97 |
| 58 | 1-Methyl-1H-indazole-3-carboxylic acid {(R)-3-[2-methyl-5-(3-trifluoromethyl-phenyl)-thiazole-4-carbonyl]-thiazolidin-4-ylmethyl}-amide | 546.11 | 1.02 |
| 59 | 1-Methyl-1H-indazole-3-carboxylic acid {(R)-3-[5-(3,4-difluoro-phenyl)-2-methyl-thiazole-4-carbonyl]-thiazolidin-4-ylmethyl}-amide | 514.11 | 0.98 |
| 60 | 1-Methyl-1H-indazole-3-carboxylic acid {(R)-3-[5-(2-methoxy-phenyl)-2-methyl-thiazole-4-carbonyl]-thiazolidin-4-ylmethyl}-amide | 508.14 | 1.00 |
| 61 | 1-Methyl-1H-indazole-3-carboxylic acid {(R)-3-[2-methyl-5-(3-trifluoromethyl-phenyl)-oxazole-4-carbonyl]-thiazolidin-4-ylmethyl}-amide | 530.13 | 0.99 |
| 62 | 1-Methyl-1H-indazole-3-carboxylic acid [(R)-3-(2-methyl-5-p-tolyl-oxazole-4-carbonyl)-thiazolidin-4-ylmethyl]-amide | 476.19 | 0.96 |
| 63 | 1-Methyl-1H-indazole-3-carboxylic acid {(R)-3-[5-(4-fluoro-phenyl)-2-methyl-oxazole-4-carbonyl]-thiazolidin-4-ylmethyl}-amide | 480.17 | 0.93 |
| 64 | 1-Methyl-1H-indazole-3-carboxylic acid [(R)-3-(2-methyl-4-p-tolyl-thiazole-5-carbonyl)-thiazolidin-4-ylmethyl]-amide | 492.14 | 0.98 |
| 65 | 1-Methyl-1H-indazole-3-carboxylic acid [(R)-3-(2-methyl-5-m-tolyl-oxazole-4-carbonyl)-thiazolidin-4-ylmethyl]-amide | 476.18 | 0.96 |
| 66 | 1-Methyl-1H-indazole-3-carboxylic acid {(R)-3-[5-(3,4-dichloro-phenyl)-2-methyl-thiazole-4-carbonyl]-thiazolidin-4-ylmethyl}-amide | 546.03 | 1.03 |
| 67 | 1-Methyl-1H-indazole-3-carboxylic acid {(R)-3-[5-(4-methoxy-phenyl)-2-methyl-oxazole-4-carbonyl]-thiazolidin-4-ylmethyl}-amide | 492.16 | 0.93 |
| 68 | 1-Methyl-1H-indazole-3-carboxylic acid [(R)-3-(4'-methyl-biphenyl-2-carbonyl)-thiazolidin-4-ylmethyl]-amide | 471.19 | 1.03 |
| 69 | 1-Methyl-1H-indazole-3-carboxylic acid [(R)-3-(3',4'-dimethyl-biphenyl-2-carbonyl)-thiazolidin-4-ylmethyl]-amide | 485.2 | 1.05 |
| 70 | 1-Methyl-1H-indazole-3-carboxylic acid [(R)-3-(3'-methyl-biphenyl-2-carbonyl)-thiazolidin-4-ylmethyl]-amide | 471.20 | 1.03 |
| 71 | 1-Methyl-1H-indazole-3-carboxylic acid [(R)-3-(3'-methoxy-biphenyl-2-carbonyl)-thiazolidin-4-ylmethyl]-amide | 487.18 | 1.00 |
| 72 | 1-Methyl-1H-indazole-3-carboxylic acid [(R)-3-(4'-fluoro-biphenyl-2-carbonyl)-thiazolidin-4-ylmethyl]-amide | 475.17 | 1.01 |
| 73 | 1-Methyl-1H-indazole-3-carboxylic acid [(R)-3-(4'-methoxy-biphenyl-2-carbonyl)-thiazolidin-4-ylmethyl]-amide | 487.18 | 1.01 |

TABLE 1-continued

| Example | Name | [M + H]+ | $t_R$ |
|---|---|---|---|
| 74 | 3-Bromo-N-{(R)-3-[5-(4-fluoro-phenyl)-2-methyl-thiazole-4-carbonyl]-thiazolidin-4-ylmethyl}-benzamide | 519.99 | 1.00 |
| 75 | 1-Methyl-1H-indole-2-carboxylic acid {(R)-3-[5-(4-fluoro-phenyl)-2-methyl-thiazole-4-carbonyl]-thiazolidin-4-ylmethyl}-amide | 495.14 | 1.02 |
| 76 | 4-Bromo-thiophene-2-carboxylic acid {(R)-3-[5-(4-fluoro-phenyl)-2-methyl-thiazole-4-carbonyl]-thiazolidin-4-ylmethyl}-amide | 525.95 | 0.99 |
| 77 | 6-Bromo-pyridine-2-carboxylic acid {(R)-3-[5-(4-fluoro-phenyl)-2-methyl-thiazole-4-carbonyl]-thiazolidin-4-ylmethyl}-amide | 521.00 | 0.98 |
| 78 | 2,3-Dihydro-benzo[1,4]dioxine-5-carboxylic acid [(R)-3-(biphenyl-2-carbonyl)-thiazolidin-4-ylmethyl]-amide | 461.17 | 0.98 |
| 79 | Benzofuran-4-carboxylic acid [(R)-3-(biphenyl-2-carbonyl)-thiazolidin-4-ylmethyl]-amide | 443.06 | 1.00 |
| 80 | N-[(R)-3-(Biphenyl-2-carbonyl)-thiazolidin-4-ylmethyl]-3-bromo-benzamide | 481.06 | 1.02 |
| 81 | 1-Methyl-1H-indole-2-carboxylic acid [(R)-3-(biphenyl-2-carbonyl)-thiazolidin-4-ylmethyl]-amide | 456.19 | 1.04 |
| 82 | 6-Methyl-imidazo[2,1-b]thiazole-5-carboxylic acid [(R)-3-(biphenyl-2-carbonyl)-thiazolidin-4-ylmethyl]-amide | 463.15 | 0.87 |
| 83 | 1-Methyl-1H-indazole-3-carboxylic acid [(R)-3-(biphenyl-2-carbonyl)-thiazolidin-4-ylmethyl]-amide | 457.18 | 1.00 |
| 84 | 4-Bromo-thiophene-2-carboxylic acid [(R)-3-(biphenyl-2-carbonyl)-thiazolidin-4-ylmethyl]-amide | 487.01 | 1.02 |
| 85 | 6-Bromo-pyridine-2-carboxylic acid [(R)-3-(biphenyl-2-carbonyl)-thiazolidin-4-ylmethyl]-amide | 482.03 | 1.01 |

A.5 Synthesis of 3-acyl-(4-aminomethyl)-thiazolidine Derivatives

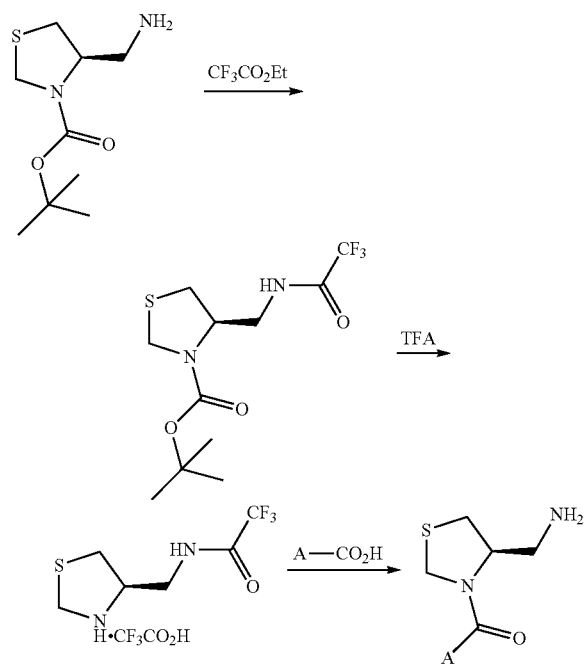

A.5.1 Synthesis of 4-[(2,2,2-trifluoro-acetylamino)-methyl]-thiazolidine-3-carboxylic acid tert-butyl ester To a solution of (R)-4-Aminomethyl-thiazolidine-3-carboxylic acid tert-butyl ester (19 mmol) in dry THF (56 mL) was added slowly ethyl trifluoroacetate (22.8 mmol, 1.2 eq)). The reaction mixture was stirred at rt for 20 h and concentrated to yield the crude title compound which was used for the next step without further purification. LC-MS: $t_R$=0.94 min; [m+H]+=315.04.

A.5.2 Synthesis of 2,2,2-trifluoro-N-thiazolidin-4-ylmethyl-acetamide (trifluoroacetic acid salt)

To a cold (0° C.) solution of 4-[(2,2,2-trifluoro-acetylamino)-methyl]-thiazolidine-3-carboxylic acid tert-butyl ester (19 mmol) in dry DCM (10 mL) was added dropwise TFA (133 mmol, 7 eq). The reaction mixture was stirred for 20 h and concentrated in vacuo to give the title compound. LC-MS: $t_R$=0.24 min; [m+H]+=214.99.

A.5.3 Synthesis of 3-acyl-(4-aminomethyl)-thiazolidine Derivatives (General Procedure)

A solution of the respective carboxylic acid A-COOH (4.6 mmol, 1 eq), TBTU (4.6 mmol, 1 eq), DIPEA (23 mmol, 5 eq) in dry DMF (15 mL) was stirred at rt for 30 min. Then, was added 2,2,2-trifluoro-N-thiazolidin-4-ylmethyl-acetamide (trifluoroacetic acid salt) (4.6 mmol, 1.0 eq.) in dry DMF (0.5 mL). Stirring was continued over night. The reaction mixture was partitioned between sat. aq. NaHCO$_3$ solution/EtOAc. The organic phase was washed with brine, dried (MgSO$_4$), filtered and concentrated to give the corresponding N-(thiazolidin-4-ylmethyl)-2,2,2-trifluoro-acetamide derivative which was used for the next step without further purification. To a solution of the above product (4.6 mmol) in dry MeOH (32 mL) was added sat. K$_2$CO$_3$ (32 mL). The reaction mixture was stirred at rt for 20 h. Diethyl ether was added, and the organic phase was washed with 25% HCl, 1N HCl. The aqueous phase was basified with 30% NaOH and extracted with DCM. The combined organic extracts were washed with brine, dried (MgSO$_4$), filtered and concentrated to give the corresponding 3-acyl-(4-aminomethyl)-thiazolidine derivative which was used for the next step without further purification.

The following intermediates were synthesized according to general procedure A.5.3 from commercially available (R)-4-aminomethyl-thiazolidine-3-carboxylic acid tert-butyl ester and the respective carboxylic acid A-COOH, which is commercially available or synthesized according to methods described above:

| Intermediate | Name | [M + H]⁺ | $t_R$ |
|---|---|---|---|
| I1 | (4-Aminomethyl-thiazolidin-3-yl)-(2-methyl-5-m-tolyl-thiazol-4-yl)-methanone | 334.11 | 0.73 |
| I2 | (4-Aminomethyl-thiazolidin-3-yl)-[5-(4-fluoro-phenyl)-2-methyl-thiazol-4-yl]-methanone | 337.99 | 0.72 |

Preparation of Examples

General Procedure 2

The corresponding acid R¹COOH (0.15 mmol, 1.0 eq.) was dissolved in a mixture of dry DMF (1.0 mL) and DIPEA (0.75 mmol, 5 eq.) under stirring. Solid TBTU (0.15 mmol, 1.0 eq.) was added and stirring was allowed for 15 min. Then was added a solution of the respective 3-acyl-(4-aminomethyl)-thiazolidine derivative (0.15 mmol, 1 eq) (Intermediate according to method A.5.3) in dry DMF (0.5 mL) and the mixture was stirred over night. The DMF was evaporated under vacuum and the crude product purified by prep. HPLC to provide the final compound.

The following Examples given in table 2 were synthesized according to the general procedure 2 given above:

TABLE 2

| Example | Name | [M + H]⁺ | $t_R$ |
|---|---|---|---|
| 86 | Naphthalene-1-carboxylic acid {(R)-3-[5-(4-fluoro-phenyl)-2-methyl-thiazole-4-carbonyl] thiazolidin-4-ylmethyl}-amide | 492.14 | 1.01 |
| 87 | 5-tert-Butyl-2-methyl-2H-pyrazole-3-carboxylic acid {(R)-3-[5-(4-fluoro-phenyl)-2-methyl-thiazole-4-carbonyl]-thiazolidin-4-ylmethyl}-amide | 502.17 | 0.99 |
| 88 | 2,3-Dihydro-benzofuran-7-carboxylic acid {(R)-3[5-(4-fluoro-phenyl)-2-methyl-thiazole-4-carbonyl]-thiazolidin-4-ylmethyl}-amide | 484.14 | 0.99 |
| 89 | 2,4-Dimethyl-thiazole-5-carboxylic acid {(R)-3-[5-(4-fluoro-phenyl)-2-methyl-thiazole-4-carbonyl]-thiazolidin-4-ylmethyl}-amide | 477.09 | 0.89 |
| 90 | N-{(R)-3-[5-(4-fluoro-phenyl)-2-methyl-thiazole-4-carbonyl]-thiazolidin-4-ylmethyl}-3-nitro-benzamide | 487.09 | 0.97 |
| 91 | Benzo[b]thiophene-2-carboxylic acid {(R)-3-[5-(4-fluoro-phenyl)-2-methyl-thiazole-4-carbonyl]-thiazolidin-4-ylmethyl}-amide | 498.01 | 1.01 |
| 92 | 2-Methyl-benzofuran-4-carboxylic acid [(R)-3-(2-methyl-5-m-tolyl-thiazole-4-carbonyl)-thiazolidin-4-ylmethyl]-amide | 492.11 | 1.02 |
| 93 | 2-Methyl-benzooxazole-4-carboxylic acid [(R)-3-(2-methyl-5-m-tolyl-thiazole-4-carbonyl)-thiazolidin-4-ylmethyl]-amide | 493.11 | 1 |
| 94 | Imidazo[1,2-a]pyridine-3-carboxylic acid [(R)-3-(2-methyl-5-m-tolyl-thiazole-4-carbonyl)-thiazolidin-4-ylmethyl]-amide | 478.13 | 0.78 |
| 95 | 2-Methyl-imidazo[1,2-a]pyridine-3-carboxylic acid [(R)-3-(2-methyl-5-m-tolyl-thiazole-4-carbonyl)-thiazolidin-4-ylmethyl]-amide | 492.12 | 0.78 |
| 96 | 2,3-Dimethyl-benzofuran-4-carboxylic acid [(R)-3-(2-methyl-5-m-tolyl-thiazole-4-carbonyl)-thiazolidin-4-ylmethyl]-amide | 506.03 | 1.04 |
| 97 | 3,4-Dihydro-2H-benzo[1,4]oxazine-5-carboxylic acid [(R)-3-(2-methyl-5-m-tolyl-thiazole-4-carbonyl)-thiazolidin-4-ylmethyl]-amide | 495.14 | 1 |
| 98 | 4-Methyl-3,4-Dihydro-2H-benzo[1,4]oxazine-5-carboxylic acid [(R)-3-(2-methyl-5-m-tolyl-thiazole-4-carbonyl)-thiazolidin-4-ylmethyl]-amide | 509.13 | 0.97 |
| 99 | Chroman-5-carboxylic acid [(R)-3-(2-methyl-5-m-tolyl-thiazole-4-carbonyl)-thiazolidin-4-ylmethyl]-amide | 494.12 | 0.99 |
| 100 | Chroman-8-carboxylic acid [(R)-3-(2-methyl-5-m-tolyl-thiazole-4-carbonyl)-thiazolidin-4-ylmethyl]-amide | 494.13 | 1.01 |
| 101 | 3,4-Dihydro-2H-benzo[1,4]oxazine-8-carboxylic acid [(R)-3-(2-methyl-5-m-tolyl-thiazole-4-carbonyl)-thiazolidin-4-ylmethyl]-amide | 495.12 | 0.92 |
| 102 | 4-Methyl-3,4-Dihydro-2H-benzo[1,4]oxazine-8-carboxylic acid [(R)-3-(2-methyl-5-m-tolyl-thiazole-4-carbonyl)-thiazolidin-4-ylmethyl]-amide | 509.13 | 0.99 |
| 103 | Benzo[d]isoxazole-3-carboxylic acid [(R)-3-(2-methyl-5-m-tolyl-thiazole-4-carbonyl)-thiazolidin-4-ylmethyl]-amide | 479.1 | 0.99 |
| 104 | Benzo[d]isothiazole-3-carboxylic acid [(R)-3-(2-methyl-5-m-tolyl-thiazole-4-carbonyl)-thiazolidin-4-ylmethyl]-amide | 495.06 | 1.04 |

TABLE 2-continued

| Example | Name | [M + H]⁺ | t_R |
|---|---|---|---|
| 105 | 1-Methyl-1H-indazole-3-carboxylic acid [(R)-3-(2-methyl-5-m-tolyl-thiazole-4-carbonyl)-thiazolidin-4-ylmethyl]-amide | 492.11 | 0.99 |
| 106 | 2,3-Dihydro-benzofuran-4-carboxylic acid [(R)-3-(2-methyl-5-m-tolyl-thiazole-4-carbonyl)-thiazolidin-4-ylmethyl]-amide | 480.12 | 0.98 |
| 107 | 2,3-Dihydro-benzo[1,4]dioxine-5-carboxylic acid [(R)-3-(2-methyl-5-m-tolyl-thiazole-4-carbonyl)-thiazolidin-4-ylmethyl]-amide | 496.1 | 0.97 |
| 108 | 2-Methyl-benzofuran-4-carboxylic acid {(R)-3-[5-(4-fluoro-phenyl)-2-methyl-thiazole-4-carbonyl]-thiazolidin-4-ylmethyl}-amide | 496.09 | 1 |
| 109 | Imidazo[1,2-a]pyridine-3-carboxylic acid {(R)-3-[5-(4-fluoro-phenyl)-2-methyl-thiazole-4-carbonyl]-thiazolidin-4-ylmethyl}-amide | 482.04 | 0.76 |
| 110 | 2-Methyl-imidazo[1,2-a]pyridine-3-carboxylic acid {(R)-3-[5-(4-fluoro-phenyl)-2-methyl-thiazole-4-carbonyl]-thiazolidin-4-ylmethyl}-amide | 496.09 | 0.75 |
| 111 | 2,3-Dimethyl-benzofuran-4-carboxylic acid {(R)-3-[5-(4-fluoro-phenyl)-2-methyl-thiazole-4-carbonyl]-thiazolidin-4-ylmethyl}-amide | 510.1 | 1.02 |
| 112 | 3,4-Dihydro-2H-benzo[1,4]oxazine-5-carboxylic acid {(R)-3-[5-(4-fluoro-phenyl)-2-methyl-thiazole-4-carbonyl]-thiazolidin-4-ylmethyl}-amide | 499.02 | 0.98 |
| 113 | 4-Methyl-3,4-dihydro-2H-benzo[1,4]oxazine-5-carboxylic acid {(R)-3-[5-(4-fluoro-phenyl)-2-methyl-thiazole-4-carbonyl]-thiazolidin-4-ylmethyl}-amide | 513.1 | 0.94 |
| 114 | Chroman-5-carboxylic acid {(R)-3-[5-(4-fluoro-phenyl)-2-methyl-thiazole-4-carbonyl]-thiazolidin-4-ylmethyl}-amide | 498.05 | 0.97 |
| 115 | Chroman-8-carboxylic acid {(R)-3-[5-(4-fluoro-phenyl)-2-methyl-thiazole-4-carbonyl]-thiazolidin-4-ylmethyl}-amide | 498.02 | 0.98 |
| 116 | 3,4-Dihydro-2H-benzo[1,4]oxazine-8-carboxylic acid {(R)-3-[5-(4-fluoro-phenyl)-2-methyl-thiazole-4-carbonyl]-thiazolidin-4-ylmethyl}-amide | 499.01 | 0.89 |
| 117 | 4-Methyl-3,4-dihydro-2H-benzo[1,4]oxazine-8-carboxylic acid {(R)-3-[5-(4-fluoro-phenyl)-2-methyl-thiazole-4-carbonyl]-thiazolidin-4-ylmethyl}-amide | 513.12 | 0.96 |
| 118 | 2,3-Dihydro-benzofuran-4-carboxylic acid {(R)-3-[5-(4-fluoro-phenyl)-2-methyl-thiazole-4-carbonyl]-thiazolidin-4-ylmethyl}-amide | 484.09 | 0.96 |
| 119 | Benzooxazole-7-carboxylic acid [(R)-3-(2-methyl-5-m-tolyl-thiazole-4-carbonyl)-thiazolidin-4-ylmethyl]-amide | 479.11 | 0.92 |
| 120 | Benzooxazole-7-carboxylic acid {(R)-3-[5-(4-fluoro-phenyl)-2-methyl-thiazole-4-carbonyl]-thiazolidin-4-ylmethyl}-amide | 482.98 | 0.89 |
| 121 | 2-Methyl-benzooxazole-7-carboxylic acid [(R)-3-(2-methyl-5-m-tolyl-thiazole-4-carbonyl)-thiazolidin-4-ylmethyl]-amide | 493.11 | 0.94 |
| 122 | 2-Methyl-benzooxazole-7-carboxylic acid {(R)-3-[5-(4-fluoro-phenyl)-2-methyl-thiazole-4-carbonyl]-thiazolidin-4-ylmethyl}-amide | 497.08 | 0.97 |
| 123 | Benzothiazole-7-carboxylic acid [(R)-3-(2-methyl-5-m-tolyl-thiazole-4-carbonyl)-thiazolidin-4-ylmethyl]-amide | 495.07 | 0.97 |
| 124 | Benzothiazole-7-carboxylic acid {(R)-3-[5-(4-fluoro-phenyl)-2-methyl-thiazole-4-carbonyl]-thiazolidin-4-ylmethyl}-amide | 498.06 | 0.95 |
| 125 | 7-Chloro-benzofuran-4-carboxylic acid [(R)-3-(2-methyl-5-m-tolyl-thiazole-4-carbonyl)-thiazolidin-4-ylmethyl]-amide | 512.06 | 1.04 |
| 126 | 7-Chloro-benzofuran-4-carboxylic acid {(R)-3-[5-(4-fluoro-phenyl)-2-methyl-thiazole-4-carbonyl]-thiazolidin-4-ylmethyl}-amide | 516.02 | 1.01 |
| 127 | 7-Fluoro-benzofuran-4-carboxylic acid [(R)-3-(2-methyl-5-m-tolyl-thiazole-4-carbonyl)-thiazolidin-4-ylmethyl]-amide | 496.08 | 1.01 |
| 128 | 7-Fluoro-benzofuran-4-carboxylic acid {(R)-3-[5-(4-fluoro-phenyl)-2-methyl-thiazole-4-carbonyl]-thiazolidin-4-ylmethyl}-amide | 500.06 | 0.99 |
| 129 | Pyrrolo[2,1-b]thiazole-7-carboxylic acid [(R)-3-(2-methyl-5-m-tolyl-thiazole-4-carbonyl)-thiazolidin-4-ylmethyl]-amide | 483.08 | 0.94 |
| 130 | Pyrrolo[2,1-b]thiazole-7-carboxylic acid {(R)-3-[5-(4-fluoro-phenyl)-2-methyl-thiazole-4-carbonyl]-thiazolidin-4-ylmethyl}-amide | 487.04 | 0.91 |

TABLE 2-continued

| Example | Name | [M + H]⁺ | $t_R$ |
|---|---|---|---|
| 131 | 6-Methyl-pyrrolo[2,1-b]thiazole-7-carboxylic acid [(R)-3-(2-methyl-5-m-tolyl-thiazole-4-carbonyl)-thiazolidin-4-ylmethyl]-amide | 497.07 | 0.96 |
| 132 | 6-Methyl-pyrrolo[2,1-b]thiazole-7-carboxylic acid {(R)-3-[5-(4-fluoro-phenyl)-2-methyl-thiazole-4-carbonyl]-thiazolidin-4-ylmethyl}-amide | 501.06 | 0.94 |
| 133 | 7-Chloro-2-methoxy-2,3-dihydro-benzofuran-4-carboxylic acid [(R)-3-(2-methyl-5-m-tolyl-thiazole-4-carbonyl)-thiazolidin-4-ylmethyl]-amide | 544.06 | 1.01 |
| 134 | 7-Chloro-2-methoxy-2,3-dihydro-benzofuran-4-carboxylic acid {(R)-3-[5-(4-fluoro-phenyl)-2-methyl-thiazole-4-carbonyl]-thiazolidin-4-ylmethyl}-amide | 548.05 | 1.04 |
| 135 | 2-Chloro-benzothiazole-4-carboxylic acid [(R)-3-(2-methyl-5-m-tolyl-thiazole-4-carbonyl)-thiazolidin-4-ylmethyl]-amide | 529.03 | 1.04 |
| 136 | 2-Chloro-benzothiazole-4-carboxylic acid {(R)-3-[5-(4-fluoro-phenyl)-2-methyl-thiazole-4-carbonyl]-thiazolidin-4-ylmethyl}-amide | 532.99 | 1.02 |
| 137 | Benzothiazole-4-carboxylic acid [(R)-3-(2-methyl-5-m-tolyl-thiazole-4-carbonyl)-thiazolidin-4-ylmethyl]-amide | 494.93 | 0.9 |
| 138 | Benzothiazole-4-carboxylic acid {(R)-3-[5-(4-fluoro-phenyl)-2-methyl-thiazole-4-carbonyl]-thiazolidin-4-ylmethyl}-amide | 499.07 | 0.88 |
| 139 | Benzo[1,2,5]thiadiazole-4-carboxylic acid [(R)-3-(2-methyl-5-m-tolyl-thiazole-4-carbonyl)-thiazolidin-4-ylmethyl]-amide | 496.12 | 1.01 |
| 140 | Benzo[1,2,5]thiadiazole-4-carboxylic acid {(R)-3-[5-(4-fluoro-phenyl)-2-methyl-thiazole-4-carbonyl]-thiazolidin-4-ylmethyl}-amide | 500.1 | 0.99 |
| 141 | 7-Trifluoromethyl-benzofuran-4-carboxylic acid [(R)-3-(2-methyl-5-m-tolyl-thiazole-4-carbonyl)-thiazolidin-4-ylmethyl]-amide | 546.08 | 1.07 |
| 142 | 7-Trifluoromethyl-benzofuran-4-carboxylic acid {(R)-3-[5-(4-fluoro-phenyl)-2-methyl-thiazole-4-carbonyl]-thiazolidin-4-ylmethyl}-amide | 550.15 | 1.04 |
| 143 | 3-Methyl-benzofuran-4-carboxylic acid [(R)-3-(2-methyl-5-m-tolyl-thiazole-4-carbonyl)-thiazolidin-4-ylmethyl]-amide | 492.17 | 1.02 |
| 144 | 3-Methyl-benzofuran-4-carboxylic acid {(R)-3-[5-(4-fluoro-phenyl)-2-methyl-thiazole-4-carbonyl]-thiazolidin-4-ylmethyl}-amide | 496.14 | 1 |
| 145 | Benzo[2,1,3]oxadiazole-4-carboxylic acid [(R)-3-(2-methyl-5-m-tolyl-thiazole-4-carbonyl)-thiazolidin-4-ylmethyl]-amide | 480.11 | 0.98 |
| 146 | Benzo[2,1,3]oxadiazole-4-carboxylic acid {(R)-3-[5-(4-fluoro-phenyl)-2-methyl-thiazole-4-carbonyl]-thiazolidin-4-ylmethyl}-amide | 484.12 | 0.89 |
| 147 | 2-Hydroxymethyl-benzofuran-4-carboxylic acid [(R)-3-(2-methyl-5-m-tolyl-thiazole-4-carbonyl)-thiazolidin-4-ylmethyl]-amide | 508.17 | 0.91 |
| 148 | 2-Hydroxymethyl-benzofuran-4-carboxylic acid {(R)-3-[5-(4-fluoro-phenyl)-2-methyl-thiazole-4-carbonyl]-thiazolidin-4-ylmethyl}-amide | 512.17 | 0.89 |
| 149 | 2-Fluoro-benzofuran-4-carboxylic acid [(R)-3-(2-methyl-5-m-tolyl-thiazole-4-carbonyl)-thiazolidin-4-ylmethyl]-amide | 496.14 | 1.03 |
| 150 | 5-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide | 526.11 | 1.05 |
| 151 | 7-Chloro-2-methyl-benzofuran-4-carboxylic acid [(R)-3-(2-methyl-5-m-tolyl-thiazole-4-carbonyl)-thiazolidin-4-ylmethyl]-amide | 526.14 | 1.07 |
| 152 | 7-Fluoro-2-methyl-benzofuran-4-carboxylic acid [(R)-3-(2-methyl-5-m-tolyl-thiazole-4-carbonyl)-thiazolidin-4-ylmethyl]-amide | 510.12 | 1.05 |
| 153 | 2-Methyl-7-trifluoromethyl-benzofuran-4-carboxylic acid [(R)-3-(2-methyl-5-m-tolyl-thiazole-4-carbonyl)-thiazolidin-4-ylmethyl]-amide | 560.23 | 1.09 |
| 154 | 6-Chloro-2-methyl-benzofuran-4-carboxylic acid [(R)-3-(2-methyl-5-m-tolyl-thiazole-4-carbonyl)-thiazolidin-4-ylmethyl]-amide | 526.12 | 1.08 |
| 155 | 6-Fluoro-2-methyl-benzofuran-4-carboxylic acid [(R)-3-(2-methyl-5-m-tolyl-thiazole-4-carbonyl)-thiazolidin-4-ylmethyl]-amide | 510.14 | 1.06 |
| 156 | 2-Methyl-6-trifluoromethyl-benzofuran-4-carboxylic acid [(R)-3-(2-methyl-5-m-tolyl-thiazole-4-carbonyl)-thiazolidin-4-ylmethyl]-amide | 560.23 | 1.1 |

TABLE 2-continued

| Example | Name | [M + H]+ | $t_R$ |
|---|---|---|---|
| 157 | 5-Chloro-2-methyl-benzofuran-4-carboxylic acid [(R)-3-(2-methyl-5-m-tolyl-thiazole-4-carbonyl)-thiazolidin-4-ylmethyl]-amide | 530.18 | 1.08 |
| 158 | 7-Chloro-2-methyl-benzofuran-4-carboxylic acid {(R)-3-5-(4-fluoro-phenyl)-2-methyl-thiazole-4-carbonyl]-thiazolidin-4-ylmethyl}-amide | 530.18 | 1.08 |
| 159 | 7-Fluoro-2-methyl-benzofuran-4-carboxylic acid {(R)-3-5-(4-fluoro-phenyl)-2-methyl-thiazole-4-carbonyl]-thiazolidin-4-ylmethyl}-amide | 514.19 | 1.06 |
| 160 | 2-Methyl-7-trifluoromethyl-benzofuran-4-carboxylic acid {(R)-3-[5-(4-fluoro-phenyl)-2-methyl-thiazole-4-carbonyl]-thiazolidin-4-ylmethyl}-amide | 564.22 | 1.1 |
| 161 | 6-Chloro-2-methyl-benzofuran-4-carboxylic acid {(R)-3-5-(4-fluoro-phenyl)-2-methyl-thiazole-4-carbonyl]-thiazolidin-4-ylmethyl}-amide | 530.18 | 1.09 |
| 162 | 6-Fluoro-2-methyl-benzofuran-4-carboxylic acid {(R)-3-5-(4-fluoro-phenyl)-2-methyl-thiazole-4-carbonyl]-thiazolidin-4-ylmethyl}-amide | 514.18 | 1.07 |
| 163 | 2-Methyl-6-trifluoromethyl-benzofuran-4-carboxylic acid {(R)-3-[5-(4-fluoro-phenyl)-2-methyl-thiazole-4-carbonyl]-thiazolidin-4-ylmethyl}-amide | 564.21 | 1.08 |

Example 164

2-Trifluoromethyl-benzofuran-4-carboxylic acid [3-(2-methyl-5-m-tolyl-thiazole-4-carbonyl)-thiazolidin-4-ylmethyl]-amide a) 2-Iodo-benzofuran-4-carboxylic acid
To a cold (−78° C.) solution of benzofuran-4-carboxylic acid (100 mg) in dry diethyl ether (1.2 mL), was added dropwise tert-butyl lithium (1.7 M in pentane, 0.8 mL, 2.2 eq). The reaction mixture was stirred at −78° C. for 30 min. under nitrogen, then a solution of iodine (172.2 mg, 1.2 eq) in ether (1.9 mL) was added dropwise. The reaction was stirred at −78° C. for 30 min. and allowed to warm to rt. The reaction mixture was partitioned between sat. NH$_4$Cl and diethyl ether, the aqueous phase was extracted once again with diethyl ether. The combined organic extracts were washed with sat. sodium thiosulfate, water, dried (Na$_2$SO$_4$), filtered and concentrated to yield a crude brown solid. FC (DCM/MeOH: 99/1 to 97/3) afforded the title compound as a pink solid (40 mg, 23%). LC-MS: $t_R$=0.89 min; [m+H]$^+$=288.99.

b) 2-Iodo-benzofuran-4-carboxylic acid [3-(2-methyl-5-m-tolyl-thiazole-4-carbonyl)-thiazolidin-4-ylmethyl]-amide
A solution of 2-iodo-benzofuran-4-carboxylic acid (29.5 mg), TBTU (34 mg 1 eq), DIPEA (0.087 mL, 5 eq) in dry DMF (0.325 mL) was stirred at rt for 15 min. Then, was added (4-Aminomethyl-thiazolidin-3-yl)-(2-methyl-5-m-tolyl-thiazol-4-yl)-methanone (34 mg, 1.0 eq.) in dry DMF (0.325 mL). Stirring was continued over night. The reaction mixture was partitioned between sat. aq. NaHCO$_3$ solution/EtOAc. The organic phase was washed with brine, dried (MgSO$_4$), filtered and concentrated to give 2-iodo-benzofuran-4-carboxylic acid [3-(2-methyl-5-m-tolyl-thiazole-4-carbonyl)-thiazolidin-4-ylmethyl]-amide (57 mg, 93%) which was used for the next step without further purification. LC-MS: $t_R$=0.89 min; [m+H]$^+$=288.99.

c) 2-Trifluoromethyl-benzofuran-4-carboxylic acid [3-(2-methyl-5-m-tolyl-thiazole-4-carbonyl)-thiazolidin-4-ylmethyl]-amide
A mixture of 2-iodo-benzofuran-4-carboxylic acid [3-(2-methyl-5-m-tolyl-thiazole-4-carbonyl)-thiazolidin-4-ylmethyl]-amide (57 mg), copper (I) iodide (91 mg, 5 eq), methyl 2,2-difluoro-2-(fluorosulfonyl)acetate (0.08 mL, 6.5 eq), HMPA (0.17 mL, 10 eq) in dry DMF (2.5 mL) was stirred at 80° C. for 16 hours under nitrogen. After cooling to rt, the reaction mixture was partitioned between water and EtOAc, the organic phase was washed again with water, dried (MgSO$_4$), filtered and concentrated in vacuo to yield a crude yellow-orange oil. FC (AlO$_3$, EtOAc/n-heptane: 7/3) gave the title compound (4.2 mg, 8%) as a white solid. LC-MS: $t_R$=1.08 min; [m+H]$^+$=546.22.

II-Biological Assays

In Vitro Assay
The orexin receptor antagonistic activity of the compounds of formula (I) is determined in accordance with the following experimental method.
Experimental Method:
Intracellular Calcium Measurements:
Chinese hamster ovary (CHO) cells expressing the human orexin-1 receptor and the human orexin-2 receptor, respectively, are grown in culture medium (Ham F-12 with L-Glutamine) containing 300 μg/ml G418, 100 U/ml penicillin, 100 μg/ml streptomycin and 10% inactivated fetal calf serum (FCS). The cells are seeded at 80,000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% CO$_2$.

Human orexin-A as an agonist is prepared as 1 mM stock solution in methanol:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 μl of loading medium (HBSS containing 1% FCS, 2 mM HEPES, 5 mM probenecid (Sigma) and 3 μM of the fluorescent calcium indicator fluo-3 AM (1 mM stock solution in DMSO with 10% pluronic acid) (Molecular Probes) is added to each well.

The 96-well plates are incubated for 60 min at 37° C. in 5% CO$_2$. The loading solution is then aspirated and cells are washed 3 times with 200 μl HBSS containing 2.5 mM probenecid, 0.1% BSA, 2 mM HEPES. 100 μl of that same buffer is left in each well.

Within the Fluorescent Imaging Plate Reader (FLIPR, Molecular Devices), antagonists are added to the plate in a volume of 50 μl, incubated for 20 min and finally 100 μl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. Antagonistic activities of compounds are in the nanomolar range below 1000 nM with respect to the $OX_1$ and/or the $OX_2$ receptor. Antagonistic activities ($IC_{50}$ values) of 162 exemplified compounds are in the range of 0.9-7245 nM with an average of 181 nM with respect to the OX1 receptor. $IC_{50}$ values of 164 exemplified compounds are in the range of 0.7-1285 nM with an average of 96 nM with respect to the $OX_2$ receptor. Antagonistic activities of selected compounds are displayed in Table 2.

TABLE 2

| Compound of Example | $OX_1$ $IC_{50}$ (nM) | $OX_2$ $IC_{50}$ (nM) |
| --- | --- | --- |
| 4 | 3 | 8 |
| 11 | 1 | 1 |
| 31 | 6 | 7 |
| 38 | 59 | 80 |
| 41 | 7 | 11 |
| 79 | 23 | 9 |
| 83 | 6 | 6 |
| 91 | 5946 | 22 |
| 110 | 99 | 804 |
| 112 | 6 | 17 |
| 119 | 2 | 3 |
| 127 | 2 | 1 |
| 132 | 5 | 6 |
| 133 | 8 | 3 |
| 141 | 10 | 4 |
| 147 | 9 | 10 |

The invention claimed is:
1. A compound of formula (I)

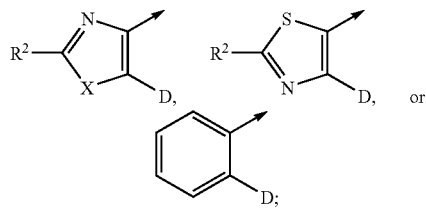

Formula (I)

wherein
A represents

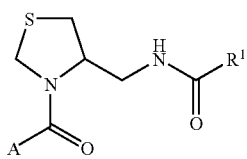

X represents O, or S;
$R^2$ represents $(C_{1-4})$alkyl;
D represents aryl, which is unsubstituted, mono-, di, or tri-substituted wherein the substituents are independently selected from the group consisting of $(C_{1-4})$alkyl, $(C_{1-4})$alkoxy, trifluoromethyl, and halogen;
$R^1$ represents aryl, wherein the aryl group is selected from the group consisting of a phenyl-, a naphthyl-, a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, a 3,4-dihydro-2H-benzo[1,4]oxazinyl-, and a 3-biphenyl group, wherein said groups are unsubstituted, mono-, di, or tri-substituted wherein the substituents are independently selected from the group consisting of $(C_{1-4})$alkyl, $(C_{1-4})$alkoxy, trifluoromethyl, halogen and nitro;
or $R^1$ represents heteroaryl, which is unsubstituted, mono-, di, or tri-substituted, wherein the substituents are independently selected from the group consisting of $(C_{1-4})$alkyl, $(C_{1-4})$alkoxy, halogen, hydroxy-$(C_{1-4})$alkyl, and trifluoromethyl;
in a free or a pharmaceutically acceptable salt form.
2. A compound according to claim 1, wherein the stereogenic center at the thiazolidine ring is in (R)-configuration.
3. A compound according to claim 1, wherein A represents

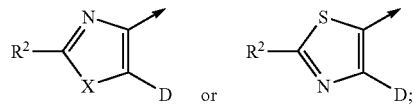

in a free or a pharmaceutically acceptable salt form.
4. A compound according to claim 1, wherein X represents S;
in a free or a pharmaceutically acceptable salt form.
5. A compound according to claim 1, wherein A represents

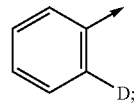

in a free or a pharmaceutically acceptable salt form.
6. A compound according to claim 1, wherein D represents unsubstituted, mono-, di-, or tri-substituted phenyl, wherein the substituents are independently selected from the group consisting of $(C_{1-4})$alkyl, $(C_{1-4})$alkoxy, trifluoromethyl, and halogen;
in a free or a pharmaceutically acceptable salt form.
7. A compound according to claim 1, wherein
$R^1$ represents aryl, wherein the aryl group is selected from the group consisting of a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, and a 3,4-dihydro-2H-benzo[1,4]oxazinyl group, wherein said groups are unsubstituted, mono-, or di-substituted wherein the substituents are independently selected from the group consisting of $(C_{1-4})$alkyl, $(C_{1-4})$alkoxy and halogen;
or $R^1$ represents heteroaryl, which is unsubstituted, mono-, di, or tri-substituted, wherein the substituents are independently selected from the group consisting of $(C_{1-4})$alkyl, $(C_{1-4})$alkoxy, halogen, hydroxy-$(C_{1-4})$alkyl, and trifluoromethyl;
in a free or a pharmaceutically acceptable salt form.
8. A compound according to claim 1, wherein
$R^1$ represents heteroaryl, wherein said hetereroaryl is selected from the group consisting of thienyl, thiazolyl, pyrazolyl, pyridyl, indolyl, benzofuranyl, indazolyl, benzoxazolyl, benzisoxazolyl, benzothiazolyl, benzoxadiazolyl, benzothiadiazolyl, imidazo[1,2-a]pyridyl, imidazo[2,1-b]thiazolyl, benzoisothiazolyl, and pyrrolo[2,1-b]thiazolyl, wherein said groups are unsubstituted, mono-, di-, or tri-substituted, wherein the substituents are independently selected from the group consisting of ($C_{1-4}$)alkyl, ($C_{1-4}$)alkoxy, halogen, hydroxy-($C_{1-4}$)alkyl, and trifluoromethyl;

in a free or a pharmaceutically acceptable salt form.

9. A compound according to claim 1, wherein $R^1$ represents aryl, wherein the aryl group is selected from the group consisting of a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, and a 3,4-dihydro-2H-benzo[1,4]oxazinyl group, wherein said groups are unsubstituted, mono-, or di-substituted wherein the substituents are independently selected from the group consisting of ($C_{1-4}$)alkyl, ($C_{1-4}$)alkoxy and halogen;

in a free or a pharmaceutically acceptable salt form.

10. A compound according to claim 1 selected from the group consisting of: Benzofuran-4-carboxylic acid {(R)-3-[5-(4-fluoro-phenyl)-2-methyl-thiazole-4-carbonyl]-thiazolidin-4-ylmethyl}-amide;

Benzofuran-4-carboxylic acid {(R)-3-[5-(2-fluoro-phenyl)-2-methyl-thiazole-4-carbonyl]-thiazolidin-4-ylmethyl}-amide;

Benzofuran-4-carboxylic acid {(R)-3-[5-(3-methoxy-phenyl)-2-methyl-thiazole-4-carbonyl]-thiazolidin-4-ylmethyl}-amide;

Benzofuran-4-carboxylic acid {(R)-3-[2-methyl-5-(3-trifluoromethyl-phenyl)-thiazole-4-carbonyl]-thiazolidin-4-ylmethyl}-amide;

Benzofuran-4-carboxylic acid {(R)-3-[5-(3,4-difluoro-phenyl)-2-methyl-thiazole-4-carbonyl]-thiazolidin-4-ylmethyl}-amide;

Benzofuran-4-carboxylic acid {(R)-3-[5-(2-methoxy-phenyl)-2-methyl-thiazole-4-carbonyl]-thiazolidin-4-ylmethyl}-amide;

Benzofuran-4-carboxylic acid {(R)-3-[2-methyl-5-(3-trifluoromethyl-phenyl)-oxazole-4-carbonyl]-thiazolidin-4-ylmethyl}-amide;

Benzofuran-4-carboxylic acid [(R)-3-(2-methyl-5-p-tolyl-oxazole-4-carbonyl)-thiazolidin-4-ylmethyl]-amide;

Benzofuran-4-carboxylic acid {(R)-3-[5-(4-fluoro-phenyl)-2-methyl-oxazole-4-carbonyl]-thiazolidin-4-ylmethyl}-amide;

Benzofuran-4-carboxylic acid [(R)-3-(2-methyl-4-p-tolyl-thiazole-5-carbonyl)-thiazolidin-4-ylmethyl]-amide;

Benzofuran-4-carboxylic acid [(R)-3-(2-methyl-5-m-tolyl-oxazole-4-carbonyl)-thiazolidin-4-ylmethyl]-amide;

Benzofuran-4-carboxylic acid [(R)-3-[5-(3,4-dichloro-phenyl)-2-methyl-thiazole-4-carbonyl]-thiazolidin-4-ylmethyl]-amide;

Benzofuran-4-carboxylic acid {(R)-3-[5-(4-methoxy-phenyl)-2-methyl-oxazole-4-carbonyl]-thiazolidin-4-ylmethyl}-amide;

Benzofuran-4-carboxylic acid [(R)-3-(4'-methyl-biphenyl-2-carbonyl)-thiazolidin-4-ylmethyl]-amide;

Benzofuran-4-carboxylic acid [(R)-3-(3',4'-dimethyl-biphenyl-2-carbonyl)-thiazolidin-4-ylmethyl]-amide;

Benzofuran-4-carboxylic acid [(R)-3-(3'-methyl-biphenyl-2-carbonyl)-thiazolidin-4-ylmethyl]-amide;

Benzofuran-4-carboxylic acid [(R)-3-(3'-methoxy-biphenyl-2-carbonyl)-thiazolidin-4-ylmethyl]-amide;

Benzofuran-4-carboxylic acid [(R)-3-(4'-fluoro-biphenyl-2-carbonyl)-thiazolidin-4-ylmethyl]-amide;

Benzofuran-4-carboxylic acid [(R)-3-(4'-methoxy-biphenyl-2-carbonyl)-thiazolidin-4-ylmethyl]-amide;

2,3-Dihydro-benzo[1,4]dioxine-5-carboxylic acid {(R)-3-[5-(4-fluoro-phenyl)-2-methyl-thiazole-4-carbonyl]-thiazolidin-4-ylmethyl}-amide;

1-Methyl-1H-indazole-3-carboxylic acid {(R)-3-[5-(4-fluoro-phenyl)-2-methyl-thiazole-4-carbonyl]-thiazolidin-4-ylmethyl}-amide;

Benzofuran-4-carboxylic acid [(R)-3-(2-methyl-5-phenyl-thiazole-4-carbonyl)-thiazolidin-4-ylmethyl]-amide;

1-Methyl-1H-indazole-3-carboxylic acid [(R)-3-(2-methyl-5-phenyl-thiazole-4-carbonyl)-thiazolidin-4-ylmethyl]-amide;

1-Methyl-1H-indazole-3-carboxylic acid [(R)-3-(2-methyl-5-p-tolyl-thiazole-4-carbonyl)-thiazolidin-4-ylmethyl]-amide;

1-Methyl-1H-indazole-3-carboxylic acid {(R)-3-[2-methyl-5-(4-trifluoromethyl-phenyl)-thiazole-4-carbonyl]-thiazolidin-4-ylmethyl}-amide;

1-Methyl-1H-indazole-3-carboxylic acid {(R)-3-[5-(3-fluoro-phenyl)-2-methyl-thiazole-4-carbonyl]-thiazolidin-4-ylmethyl}-amide;

1-Methyl-1H-indazole-3-carboxylic acid {(R)-3-[5-(3,4-dimethyl-phenyl)-2-methyl-thiazole-4-carbonyl]-thiazolidin-4-ylmethyl}-amide;

1-Methyl-1H-indazole-3-carboxylic acid {(R)-3-[(2-fluoro-phenyl)-2-methyl-thiazole-4-carbonyl]-thiazolidin-4-ylmethyl}-amide;

1-Methyl-1H-indazole-3-carboxylic acid {(R)-3-[5-(3-methoxy-phenyl)-2-methyl-thiazole-4-carbonyl]-thiazolidin-4-ylmethyl}-amide;

1-Methyl-1H-indazole-3-carboxylic acid {(R)-3-[2-methyl-5-(3-trifluoromethyl-phenyl)-thiazole-4-carbonyl]-thiazolidin-4-ylmethyl}-amide;

1-Methyl-1H-indazole-3-carboxylic acid {(R)-3-[5-(3,4-difluoro-phenyl)-2-methyl-thiazole-4-carbonyl]-thiazolidin-4-ylmethyl}-amide;

Benzofuran-4-carboxylic acid [(R)-3-(2-methyl-5-p-tolyl-thiazole-4-carbonyl)-thiazolidin-4-ylmethyl]-amide;

1-Methyl-1H-indazole-3-carboxylic acid {(R)-3-[5-(2-methoxy-phenyl)-2-methyl-thiazole-4-carbonyl]-thiazolidin-4-ylmethyl}-amide;

1-Methyl-1H-indazole-3-carboxylic acid {(R)-3-[2-methyl-5-(3-trifluoromethyl-phenyl)-oxazole-4-carbonyl]-thiazolidin-4-ylmethyl}-amide;

1-Methyl-1H-indazole-3-carboxylic acid [(R)-3-(2-methyl-5-p-tolyl-oxazole-4-carbonyl)-thiazolidin-4-ylmethyl]-amide;

1-Methyl-1H-indazole-3-carboxylic acid {(R)-3-(4-fluoro-phenyl)-2-methyl-oxazole-4-carbonyl]-thiazolidin-4-ylmethyl}-amide;

1-Methyl-1H-indazole-3-carboxylic acid [(R)-3-(2-methyl-4-p-tolyl-thiazole-5-carbonyl)-thiazolidin-4-ylmethyl]-amide;

1-Methyl-1H-indazole-3-carboxylic acid [(R)-3-(2-methyl-5-m-tolyl-oxazole-4-carbonyl)-thiazolidin-4-ylmethyl]-amide;

1-Methyl-1H-indazole-3-carboxylic acid {(R)-3-[5-(3,4-dichloro-phenyl)-2-methyl-thiazole-4-carbonyl]-thiazolidin-4-ylmethyl}-amide;

1-Methyl-1H-indazole-3-carboxylic acid {(R)-3-[5-(4-methoxy-phenyl)-2-methyl-oxazole-4-carbonyl]-thiazolidin-4-ylmethyl}-amide;

1-Methyl-1H-indazole-3-carboxylic acid [(R)-3-(4'-methyl-biphenyl-2-carbonyl)-thiazolidin-4-ylmethyl]-amide;
1-Methyl-1H-indazole-3-carboxylic acid [(R)-3-(3',4'-dimethyl-biphenyl-2-carbonyl)-thiazolidin-4-ylmethyl]-amide;
Benzofuran-4-carboxylic acid {(R)-3-[2-methyl-5-(4-trifluoromethyl-phenyl)-thiazole-4-carbonyl]-thiazolidin-4-ylmethyl}-amide;
1-Methyl-1H-indazole-3-carboxylic acid [(R)-3-(3'-methyl-biphenyl-2-carbonyl)-thiazolidin-4-ylmethyl]-amide;
1-Methyl-1H-indazole-3-carboxylic acid [(R)-3-(3'-methoxy-biphenyl-2-carbonyl)-thiazolidin-4-ylmethyl]-amide;
1-Methyl-1H-indazole-3-carboxylic acid [(R)-3-(4'-fluoro-biphenyl-2-carbonyl)-thiazolidin-4-ylmethyl]-amide;
1-Methyl-1H-indazole-3-carboxylic acid [(R)-3-(4'-methoxy-biphenyl-2-carbonyl)-thiazolidin-4-ylmethyl]-amide;
3-Bromo-N-{(R)-3-[5-(4-fluoro-phenyl)-2-methyl-thiazole-4-carbonyl]-thiazolidin-4-ylmethyl}-benzamide;
1-Methyl-1H-indole-2-carboxylic acid {(R)-3-[5-(4-fluoro-phenyl)-2-methyl-thiazole-4-carbonyl]-thiazolidin-4-ylmethyl}-amide;
4-Bromo-thiophene-2-carboxylic acid {(R)-3-[5-(4-fluoro-phenyl)-2-methyl-thiazole-4-carbonyl]-thiazolidin-4-ylmethyl}-amide;
6-Bromo-pyridine-2-carboxylic acid {(R)-3-[5-(4-fluoro-phenyl)-2-methyl-thiazole-4-carbonyl]-thiazolidin-4-ylmethyl}-amide;
2,3-Dihydro-benzo[1,4]dioxine-5-carboxylic acid [(R)-3-(biphenyl-2-carbonyl)-thiazolidin-4-ylmethyl]-amide;
Benzofuran-4-carboxylic acid [(R)-3-(biphenyl-2-carbonyl)-thiazolidin-4-ylmethyl]-amide;
Benzofuran-4-carboxylic acid {(R)-3-[5-(3-fluoro-phenyl)-2-methyl-thiazole-4-carbonyl]-thiazolidin-4-ylmethyl}-amide;
N—[(R)-3-(Biphenyl-2-carbonyl)-thiazolidin-4-ylmethyl]-3-bromo-benzamide;
1-Methyl-1H-indole-2-carboxylic acid [(R)-3-(biphenyl-2-carbonyl)-thiazolidin-4-ylmethyl]-amide;
1-Methyl-1H-indazole-3-carboxylic acid [(R)-3-(biphenyl-2-carbonyl)-thiazolidin-4-ylmethyl]-amide;
4-Bromo-thiophene-2-carboxylic acid [(R)-3-(biphenyl-2-carbonyl)-thiazolidin-4-ylmethyl]-amide;
6-Bromo-pyridine-2-carboxylic acid [(R)-3-(biphenyl-2-carbonyl)-thiazolidin-4-ylmethyl]-amide;
Benzofuran-4-carboxylic acid {(R)-3-[5-(3,4-dimethyl-phenyl)-2-methyl-thiazole-4-carbonyl]-thiazolidin-4-ylmethyl}-amide;
Naphthalene-1-carboxylic acid {(R)-3-[5-(4-fluoro-phenyl)-2-methyl-thiazole-4-carbonyl]-thiazolidin-4-ylmethyl}-amide;
5-tert-Butyl-2-methyl-2H-pyrazole-3-carboxylic acid {(R)-3-[5-(4-fluoro-phenyl)-2-methyl-thiazole-4-carbonyl]-thiazolidin-4-ylmethyl}-amide;
2,3-Dihydro-benzofuran-7-carboxylic acid {(R)-3-[5-(4-fluoro-phenyl)-2-methyl-thiazole-4-carbonyl]-thiazolidin-4-ylmethyl}-amide;
2,4-Dimethyl-thiazole-5-carboxylic acid {(R)-3-[5-(4-fluoro-phenyl)-2-methyl-thiazole-4-carbonyl]-thiazolidin-4-ylmethyl}-amide;
N-{(R)-3-[5-(4-fluoro-phenyl)-2-methyl-thiazole-4-carbonyl]-thiazolidin-4-ylmethyl}-3-nitro-benzamide;
Benzo[b]thiophene-2-carboxylic acid {(R)-3-[5-(4-fluoro-phenyl)-2-methyl-thiazole-4-carbonyl]-thiazolidin-4-ylmethyl}-amide;
2-Methyl-benzofuran-4-carboxylic acid [(R)-3-(2-methyl-5-m-tolyl-thiazole-4-carbonyl)-thiazolidin-4-ylmethyl]-amide;
2-Methyl-benzooxazole-4-carboxylic acid [(R)-3-(2-methyl-5-m-tolyl-thiazole-4-carbonyl)-thiazolidin-4-ylmethyl]-amide;
Imidazo[1,2-a]pyridine-3-carboxylic acid [(R)-3-(2-methyl-5-m-tolyl-thiazole-4-carbonyl)-thiazolidin-4-ylmethyl]-amide;
2-Methyl-imidazo[1,2-a]pyridine-3-carboxylic acid [(R)-3-(2-methyl-5-m-tolyl-thiazole-4-carbonyl)-thiazolidin-4-ylmethyl]-amide;
2,3-Dimethyl-benzofuran-4-carboxylic acid [(R)-3-(2-methyl-5-m-tolyl-thiazole-4-carbonyl)-thiazolidin-4-ylmethyl]-amide;
3,4-Dihydro-2H-benzo[1,4]oxazine-5-carboxylic acid [(R)-3-(2-methyl-5-m-tolyl-thiazole-4-carbonyl)-thiazolidin-4-ylmethyl]-amide;
4-Methyl-3,4-Dihydro-2H-benzo[1,4]oxazine-5-carboxylic acid [(R)-3-(2-methyl-5-m-tolyl-thiazole-4-carbonyl)-thiazolidin-4-ylmethyl]-amide;
Chroman-5-carboxylic acid [(R)-3-(2-methyl-5-m-tolyl-thiazole-4-carbonyl)-thiazolidin-4-ylmethyl]-amide;
Chroman-8-carboxylic acid [(R)-3-(2-methyl-5-m-tolyl-thiazole-4-carbonyl)-thiazolidin-4-ylmethyl]-amide;
3,4-Dihydro-2H-benzo[1,4]oxazine-8-carboxylic acid [(R)-3-(2-methyl-5-m-tolyl-thiazole-4-carbonyl)-thiazolidin-4-ylmethyl]-amide;
4-Methyl-3,4-Dihydro-2H-benzo[1,4]oxazine-8-carboxylic acid [(R)-3-(2-methyl-5-m-tolyl-thiazole-4-carbonyl)-thiazolidin-4-ylmethyl]-amide;
Benzo[d]isoxazole-3-carboxylic acid [(R)-3-(2-methyl-5-m-tolyl-thiazole-4-carbonyl)-thiazolidin-4-ylmethyl]-amide;
Benzo[d]isothiazole-3-carboxylic acid [(R)-3-(2-methyl-5-m-tolyl-thiazole-4-carbonyl)-thiazolidin-4-ylmethyl]-amide;
1-Methyl-1H-indazole-3-carboxylic acid [(R)-3-(2-methyl-5-m-tolyl-thiazole-4-carbonyl)-thiazolidin-4-ylmethyl]-amide;
2,3-Dihydro-benzofuran-4-carboxylic acid [(R)-3-(2-methyl-5-m-tolyl-thiazole-4-carbonyl)-thiazolidin-4-ylmethyl]-amide;
2,3-Dihydro-benzo[1,4]dioxine-5-carboxylic acid [(R)-3-(2-methyl-5-m-tolyl-thiazole-4-carbonyl)-thiazolidin-4-ylmethyl]-amide;
2-Methyl-benzofuran-4-carboxylic acid {(R)-3-[5-(4-fluoro-phenyl)-2-methyl-thiazole-4-carbonyl]-thiazolidin-4-ylmethyl}-amide;
Imidazo[1,2-a]pyridine-3-carboxylic acid {(R)-3-[5-(4-fluoro-phenyl)-2-methyl-thiazole-4-carbonyl]-thiazolidin-4-ylmethyl}-amide;
2-Methyl-imidazo[1,2-a]pyridine-3-carboxylic acid {(R)-3-[5-(4-fluoro-phenyl)-2-methyl-thiazole-4-carbonyl]-thiazolidin-4-ylmethyl}-amide;
2,3-Dimethyl-benzofuran-4-carboxylic acid {(R)-3-[5-(4-fluoro-phenyl)-2-methyl-thiazole-4-carbonyl]-thiazolidin-4-ylmethyl}-amide;
3,4-Dihydro-2H-benzo[1,4]oxazine-5-carboxylic acid {(R)-3-[5-(4-fluoro-phenyl)-2-methyl-thiazole-4-carbonyl]-thiazolidin-4-ylmethyl}-amide;
4-Methyl-3,4-dihydro-2H-benzo[1,4]oxazine-5-carboxylic acid {(R)-3-[5-(4-fluoro-phenyl)-2-methyl-thiazole-4-carbonyl]-thiazolidin-4-ylmethyl}-amide;

Chroman-5-carboxylic acid {(R)-3-[5-(4-fluoro-phenyl)-2-methyl-thiazole-4-carbonyl]-thiazolidin-4-ylmethyl}-amide;
Chroman-8-carboxylic acid {(R)-3-[5-(4-fluoro-phenyl)-2-methyl-thiazole-4-carbonyl]-thiazolidin-4-ylmethyl}-amide;
3,4-Dihydro-2H-benzo[1,4]oxazine-8-carboxylic acid {(R)-3-[5-(4-fluoro-phenyl)-2-methyl-thiazole-4-carbonyl]-thiazolidin-4-ylmethyl}-amide;
4-Methyl-3,4-dihydro-2H-benzo[1,4]oxazine-8-carboxylic acid {(R)-3-[5-(4-fluoro-phenyl)-2-methyl-thiazole-4-carbonyl]-thiazolidin-4-ylmethyl}-amide;
2,3-Dihydro-benzofuran-4-carboxylic acid {(R)-3-[5-(4-fluoro-phenyl)-2-methyl-thiazole-4-carbonyl]-thiazolidin-4-ylmethyl}-amide;
Benzooxazole-7-carboxylic acid [(R)-3-(2-methyl-5-m-tolyl-thiazole-4-carbonyl)-thiazolidin-4-ylmethyl]-amide;
Benzooxazole-7-carboxylic acid {(R)-3-[5-(4-fluoro-phenyl)-2-methyl-thiazole-4-carbonyl]-thiazolidin-4-ylmethyl}-amide;
2-Methyl-benzooxazole-7-carboxylic acid [(R)-3-(2-methyl-5-m-tolyl-thiazole-4-carbonyl)-thiazolidin-4-ylmethyl]-amide;
2-Methyl-benzooxazole-7-carboxylic acid {(R)-3-[5-(4-fluoro-phenyl)-2-methyl-thiazole-4-carbonyl]-thiazolidin-4-ylmethyl}-amide;
Benzothiazole-7-carboxylic acid [(R)-3-(2-methyl-5-m-tolyl-thiazole-4-carbonyl)-thiazolidin-4-ylmethyl]-amide;
Benzothiazole-7-carboxylic acid {(R)-3-[5-(4-fluoro-phenyl)-2-methyl-thiazole-4-carbonyl]-thiazolidin-4-ylmethyl}-amide;
7-Chloro-benzofuran-4-carboxylic acid [(R)-3-(2-methyl-5-m-tolyl-thiazole-4-carbonyl)-thiazolidin-4-ylmethyl]-amide;
7-Chloro-benzofuran-4-carboxylic acid {(R)-3-[5-(4-fluoro-phenyl)-2-methyl-thiazole-4-carbonyl]-thiazolidin-4-ylmethyl}-amide;
7-Fluoro-benzofuran-4-carboxylic acid [(R)-3-(2-methyl-5-m-tolyl-thiazole-4-carbonyl)-thiazolidin-4-ylmethyl]-amide;
7-Fluoro-benzofuran-4-carboxylic acid {(R)-3-[5-(4-fluoro-phenyl)-2-methyl-thiazole-4-carbonyl]-thiazolidin-4-ylmethyl}-amide;
Pyrrolo[2,1-b]thiazole-7-carboxylic acid [(R)-3-(2-methyl-5-m-tolyl-thiazole-4-carbonyl)-thiazolidin-4-ylmethyl]-amide;
Pyrrolo[2,1-b]thiazole-7-carboxylic acid {(R)-3-[5-(4-fluoro-phenyl)-2-methyl-thiazole-4-carbonyl]-thiazolidin-4-ylmethyl}-amide;
6-Methyl-pyrrolo[2,1-b]thiazole-7-carboxylic acid [(R)-3-(2-methyl-5-m-tolyl-thiazole-4-carbonyl)-thiazolidin-4-ylmethyl]-amide;
6-Methyl-pyrrolo[2,1-b]thiazole-7-carboxylic acid {(R)-3-[5-(4-fluoro-phenyl)-2-methyl-thiazole-4-carbonyl]-thiazolidin-4-ylmethyl}-amide;
7-Chloro-2-methoxy-2,3-dihydro-benzofuran-4-carboxylic acid [(R)-3-(2-methyl-5-m-tolyl-thiazole-4-carbonyl)-thiazolidin-4-ylmethyl]-amide;
7-Chloro-2-methoxy-2,3-dihydro-benzofuran-4-carboxylic acid {(R)-3-[5-(4-fluoro-phenyl)-2-methyl-thiazole-4-carbonyl]-thiazolidin-4-ylmethyl}-amide;
2-Chloro-benzothiazole-4-carboxylic acid [(R)-3-(2-methyl-5-m-tolyl-thiazole-4-carbonyl)-thiazolidin-4-ylmethyl]-amide;
2-Chloro-benzothiazole-4-carboxylic acid {(R)-3-[5-(4-fluoro-phenyl)-2-methyl-thiazole-4-carbonyl]-thiazolidin-4-ylmethyl}-amide;
Benzothiazole-4-carboxylic acid [(R)-3-(2-methyl-5-m-tolyl-thiazole-4-carbonyl)-thiazolidin-4-ylmethyl]-amide;
Benzothiazole-4-carboxylic acid {(R)-3-[5-(4-fluoro-phenyl)-2-methyl-thiazole-4-carbonyl]-thiazolidin-4-ylmethyl}-amide;
Benzo[2,1,3]thiadiazole-4-carboxylic acid [(R)-3-(2-methyl-5-m-tolyl-thiazole-4-carbonyl)-thiazolidin-4-ylmethyl]-amide;
Benzo[2,1,3]thiadiazole-4-carboxylic acid {(R)-3-[5-(4-fluoro-phenyl)-2-methyl-thiazole-4-carbonyl]-thiazolidin-4-ylmethyl}-amide;
7-Trifluoromethyl-benzofuran-4-carboxylic acid [(R)-3-(2-methyl-5-m-tolyl-thiazole-4-carbonyl)-thiazolidin-4-ylmethyl]-amide;
7-Trifluoromethyl-benzofuran-4-carboxylic acid {(R)-3-[5-(4-fluoro-phenyl)-2-methyl-thiazole-4-carbonyl]-thiazolidin-4-ylmethyl}-amide;
3-Methyl-benzofuran-4-carboxylic acid [(R)-3-(2-methyl-5-m-tolyl-thiazole-4-carbonyl)-thiazolidin-4-ylmethyl]-amide;
3-Methyl-benzofuran-4-carboxylic acid {(R)-3-[5-(4-fluoro-phenyl)-2-methyl-thiazole-4-carbonyl]-thiazolidin-4-ylmethyl}-amide;
Benzo[2,1,3]oxadiazole-4-carboxylic acid [(R)-3-(2-methyl-5-m-tolyl-thiazole-4-carbonyl)-thiazolidin-4-ylmethyl]-amide;
Benzo[2,1,3]oxadiazole-4-carboxylic acid {(R)-3-[5-(4-fluoro-phenyl)-2-methyl-thiazole-4-carbonyl]-thiazolidin-4-ylmethyl}-amide;
2-Hydroxymethyl-benzofuran-4-carboxylic acid [(R)-3-(2-methyl-5-m-tolyl-thiazole-4-carbonyl)-thiazolidin-4-ylmethyl]-amide;
2-Hydroxymethyl-benzofuran-4-carboxylic acid {(R)-3-[5-(4-fluoro-phenyl)-2-methyl-thiazole-4-carbonyl]-thiazolidin-4-ylmethyl}-amide;
2-Methyl-benzofuran-4-carboxylic acid [(R)-3-(2-methyl-5-m-tolyl-thiazole-4-carbonyl)-thiazolidin-4-ylmethyl]-amide;
5-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide;
7-Chloro-2-methyl-benzofuran-4-carboxylic acid [(R)-3-(2-methyl-5-m-tolyl-thiazole-4-carbonyl)-thiazolidin-4-ylmethyl]-amide;
7-Fluoro-2-methyl-benzofuran-4-carboxylic acid [(R)-3-(2-methyl-5-m-tolyl-thiazole-4-carbonyl)-thiazolidin-4-ylmethyl]-amide;
2-Methyl-7-trifluoromethyl-benzofuran-4-carboxylic acid [(R)-3-(2-methyl-5-m-tolyl-thiazole-4-carbonyl)-thiazolidin-4-ylmethyl]-amide;
6-Chloro-2-methyl-benzofuran-4-carboxylic acid [(R)-3-(2-methyl-5-m-tolyl-thiazole-4-carbonyl)-thiazolidin-4-ylmethyl]-amide;
6-Fluoro-2-methyl-benzofuran-4-carboxylic acid [(R)-3-(2-methyl-5-m-tolyl-thiazole-4-carbonyl)-thiazolidin-4-ylmethyl]-amide;
2-Methyl-6-trifluoromethyl-benzofuran-4-carboxylic acid [(R)-3-(2-methyl-5-m-tolyl-thiazole-4-carbonyl)-thiazolidin-4-ylmethyl]-amide;
5-Chloro-2-methyl-benzofuran-4-carboxylic acid [(R)-3-(2-methyl-5-m-tolyl-thiazole-4-carbonyl)-thiazolidin-4-ylmethyl]-amide;

7-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide;

7-Fluoro-2-methyl-benzofuran-4-carboxylic acid {(R)-3-[5-(4-fluoro-phenyl)-2-methyl-thiazole-4-carbonyl]-thiazolidin-4-ylmethyl}-amide;

2-Methyl-7-trifluoromethyl-benzofuran-4-carboxylic acid {(R)-3-[5-(4-fluoro-phenyl)-2-methyl-thiazole-4-carbonyl]-thiazolidin-4-ylmethyl}-amide;

6-Chloro-2-methyl-benzofuran-4-carboxylic acid {(R)-3-[5-(4-fluoro-phenyl)-2-methyl-thiazole-4-carbonyl]-thiazolidin-4-ylmethyl}-amide;

6-Fluoro-2-methyl-benzofuran-4-carboxylic acid {(R)-3-[5-(4-fluoro-phenyl)-2-methyl-thiazole-4-carbonyl]-thiazolidin-4-ylmethyl}-amide;

2-Methyl-6-trifluoromethyl-benzofuran-4-carboxylic acid {(R)-3-[5-(4-fluoro-phenyl)-2-methyl-thiazole-4-carbonyl]-thiazolidin-4-ylmethyl}-amide;

2-Trifluoromethyl-benzofuran-4-carboxylic acid [3-(2-methyl-5-m-tolyl-thiazole-4-carbonyl)-thiazolidin-4-ylmethyl]-amide;

6-Methyl-imidazo[2,1-b]thiazole-5-carboxylic acid {(R)-3-[(4-fluoro-phenyl)-2-methyl-thiazole-4-carbonyl]-thiazolidin-4-ylmethyl}-amide;

6-Methyl-imidazo[2,1-b]thiazole-5-carboxylic acid [(R)-3-(2-methyl-5-phenyl-thiazole-4-carbonyl)-thiazolidin-4-ylmethyl]-amide;

6-Methyl-imidazo[2,1-b]thiazole-5-carboxylic acid [(R)-3-(2-methyl-5-p-tolyl-thiazole-4-carbonyl)-thiazolidin-4-ylmethyl]-amide;

6-Methyl-imidazo[2,1-b]thiazole-5-carboxylic acid {(R)-3-[2-methyl-5-(4-trifluoromethyl-phenyl)-thiazole-4-carbonyl]-thiazolidin-4-ylmethyl}-amide;

6-Methyl-imidazo[2,1-b]thiazole-5-carboxylic acid {(R)-3-[5-(3-fluoro-phenyl)-2-methyl-thiazole-4-carbonyl]-thiazolidin-4-ylmethyl}-amide;

6-Methyl-imidazo[2,1-b]thiazole-5-carboxylic acid {(R)-3-[5-(3,4-dimethyl-phenyl)-2-methyl-thiazole-4-carbonyl]-thiazolidin-4-ylmethyl}-amide;

6-Methyl-imidazo[2,1-b]thiazole-5-carboxylic acid {(R)-3-[(2-fluoro-phenyl)-2-methyl-thiazole-4-carbonyl]-thiazolidin-4-ylmethyl}-amide;

6-Methyl-imidazo[2,1-b]thiazole-5-carboxylic acid {(R)-3-[5-(3-methoxy-phenyl)-2-methyl-thiazole-4-carbonyl]-thiazolidin-4-ylmethyl}-amide;

6-Methyl-imidazo[2,1-b]thiazole-5-carboxylic acid {(R)-3-[2-methyl-5-(3-trifluoromethyl-phenyl)-thiazole-4-carbonyl]-thiazolidin-4-ylmethyl}-amide;

6-Methyl-imidazo[2,1-b]thiazole-5-carboxylic acid {(R)-3-[5-(3,4-difluoro-phenyl)-2-methyl-thiazole-4-carbonyl]-thiazolidin-4-ylmethyl}-amide;

6-Methyl-imidazo[2,1-b]thiazole-5-carboxylic acid {(R)-3-[5-(2-methoxy-phenyl)-2-methyl-thiazole-4-carbonyl]-thiazolidin-4-ylmethyl}-amide;

6-Methyl-imidazo[2,1-b]thiazole-5-carboxylic acid {(R)-3-[2-methyl-5-(3-trifluoromethyl-phenyl)-oxazole-4-carbonyl]-thiazolidin-4-ylmethyl}-amide;

6-Methyl-imidazo[2,1-b]thiazole-5-carboxylic acid [(R)-3-(2-methyl-5-p-tolyl-oxazole-4-carbonyl)-thiazolidin-4-ylmethyl]-amide;

6-Methyl-imidazo[2,1-b]thiazole-5-carboxylic acid {(R)-3-[5-(4-fluoro-phenyl)-2-methyl-oxazole-4-carbonyl]-thiazolidin-4-ylmethyl}-amide;

6-Methyl-imidazo[2,1-b]thiazole-5-carboxylic acid [(R)-3-(2-methyl-4-p-tolyl-thiazole-5-carbonyl)-thiazolidin-4-ylmethyl]-amide;

6-Methyl-imidazo[2,1-b]thiazole-5-carboxylic acid [(R)-3-(2-methyl-5-m-tolyl-oxazole-4-carbonyl)-thiazolidin-4-ylmethyl]-amide;

6-Methyl-imidazo[2,1-b]thiazole-5-carboxylic acid {(R)-3-[5-(3,4-dichloro-phenyl)-2-methyl-thiazole-4-carbonyl]-thiazolidin-4-ylmethyl}-amide;

6-Methyl-imidazo[2,1-b]thiazole-5-carboxylic acid {(R)-3-[5-(4-methoxy-phenyl)-2-methyl-oxazole-4-carbonyl]-thiazolidin-4-ylmethyl}-amide;

6-Methyl-imidazo[2,1-b]thiazole-5-carboxylic acid [(R)-3-(4'-methyl-biphenyl-2-carbonyl)-thiazolidin-4-ylmethyl]-amide;

6-Methyl-imidazo[2,1-b]thiazole-5-carboxylic acid [(R)-3-(3',4'-dimethyl-biphenyl-2-carbonyl)-thiazolidin-4-ylmethyl]-amide;

6-Methyl-imidazo[2,1-b]thiazole-5-carboxylic acid [(R)-3-(3'-methyl-biphenyl-2-carbonyl)-thiazolidin-4-ylmethyl]-amide;

6-Methyl-imidazo[2,1-b]thiazole-5-carboxylic acid [(R)-3-(3'-methoxy-biphenyl-2-carbonyl)-thiazolidin-4-ylmethyl]-amide;

6-Methyl-imidazo[2,1-b]thiazole-5-carboxylic acid [(R)-3-(4'-fluoro-biphenyl-2-carbonyl)-thiazolidin-4-ylmethyl]-amide;

6-Methyl-imidazo[2,1-b]thiazole-5-carboxylic acid [(R)-3-(4'-methoxy-biphenyl-2-carbonyl)-thiazolidin-4-ylmethyl]-amide; and 6-Methyl-imidazo[2,1-b]thiazole-5-carboxylic acid [(R)-3-(biphenyl-2-carbonyl)-thiazolidin-4-ylmethyl]-amide;

in a free or a pharmaceutically acceptable salt form of such a compound.

11. A method for the treatment of a sleep disorder comprising administering to a subject in need thereof a pharmaceutically active amount of a compound according to claim 1, in a free or pharmaceutically acceptable salt form.

12. The method according to claim 11 for the treatment of insomnia.

13. A pharmaceutical composition comprising a compound according to claim 1 in a free or pharmaceutically acceptable salt form, and a pharmaceutically acceptable carrier.

14. The compound according to claim 6, wherein
R$^1$ represents aryl, wherein the aryl group is selected from the group consisting of a 2,3-dihydro-benzofuranyl-, a benzo[1,3]dioxolyl-, a 2,3-dihydro-benzo[1,4]dioxinyl-, a 4H-benzo[1,3]dioxinyl, a 2H-chromenyl-, a chromanyl-, and a 3,4-dihydro-2H-benzo[1,4]oxazinyl group, wherein said groups are unsubstituted, mono-, or di-substituted wherein the substituents are independently selected from the group consisting of (C$_{1-4}$)alkyl, (C$_{1-4}$)alkoxy and halogen; or R$^1$ represents heteroaryl, which is unsubstituted, mono-, di, or tri-substituted, wherein the substituents are independently selected from the group consisting of (C$_{1-4}$)alkyl, (C$_{1-4}$)alkoxy, halogen, hydroxy-(C$_{1-4}$)alkyl, and trifluoromethyl;
in a free or a pharmaceutically acceptable salt form.

15. A method for the treatment of a sleep disorder comprising administering to a subject in need thereof a pharmaceutically active amount of a compound according to claim 10, in a free or pharmaceutically acceptable salt form.

16. The method for treatment of insomnia comprising administering to a subject in need thereof a pharmaceutically active amount of a compound according to claim 10, in a free or pharmaceutically acceptable salt form.

17. A pharmaceutical composition comprising a compound according to claim 10 in a free or pharmaceutically acceptable salt form, and a pharmaceutically acceptable carrier.

* * * * *

UNITED STATES PATENT AND TRADEMARK OFFICE
CERTIFICATE OF CORRECTION

PATENT NO. : 8,236,964 B2
APPLICATION NO. : 12/593095
DATED : August 7, 2012
INVENTOR(S) : Aissaoui et al.

It is certified that error appears in the above-identified patent and that said Letters Patent is hereby corrected as shown below:

In the Claims:

Column 68, claim 9, lines 30-32, please replace "1-Methyl-1H-indazole-3-carboxylic acid {(R)-3-[(2-fluoro-phenyl)-2-methyl-thiazole-4-carbonyl]-thiazolidin-4-ylmethyl}-amide;" with "1-Methyl-1H-indazole-3-carboxylic acid {(R)-3-[5-(2-fluoro-phenyl)-2-methyl-thiazole-4-carbonyl]-thiazolidin-4-ylmethyl}-amide;"

Column 68, claim 9, lines 53-55, please replace "1-Methyl-1H-indazole-3-carboxylic acid {(R)-3-(4-fluoro-phenyl)-2-methyl-oxazole-4-carbonyl]-thiazolidin-4-ylmethyl}-amide;" with "1-Methyl-1H-indazole-3-carboxylic acid {(R)-3-[5-(4-fluoro-phenyl)-2-methyl-oxazole-4-carbonyl]-thiazolidin-4-ylmethyl}-amide;"

Column 73, claim 9, lines 38-40, please replace "6-Methyl-imidazo[2,1-b]thiazole-5-carboxylic acid {(R)-3-[(2-fluoro-phenyl)-2-methyl-thiazole-4-carbonyl]-thiazolidin-4-ylmethyl}-amide;" with "6-Methyl-imidazo[2,1-b]thiazole-5-carboxylic acid {(R)-3-[5-(2-fluoro-phenyl)-2-methyl-thiazole-4-carbonyl]-thiazolidin-4-ylmethyl}-amide;"

Signed and Sealed this
Twenty-seventh Day of November, 2012

David J. Kappos
*Director of the United States Patent and Trademark Office*